(12) United States Patent
Naruse et al.

(10) Patent No.: US 9,504,632 B2
(45) Date of Patent: Nov. 29, 2016

(54) COMPOUND, COMPOSITION COMPRISING THE COMPOUND AND CURED PRODUCT

(75) Inventors: Hiroshi Naruse, Chiba (JP);
Yoshimitsu Tanabe, Ichihara (JP);
Osamu Kohgo, Yokohama (JP);
Masataka Miyasato, Ichihara (JP);
Hideyuki Ueki, Kusatsu (JP);
Chidzuru Inami, Konan (JP);
Shunsuke Miyata, Kyoto (JP)

(73) Assignees: MITSUI CHEMICALS, INC., Tokyo (JP); SUN MEDICAL CO., LTD., Shiga (JP); SHOFU INC., Kyoto (JP)

( * ) Notice: Subject to any disclaimer, the term of this patent is extended or adjusted under 35 U.S.C. 154(b) by 876 days.

(21) Appl. No.: 13/471,765

(22) Filed: May 15, 2012

(65) Prior Publication Data

US 2012/0296061 A1 Nov. 22, 2012

Related U.S. Application Data

(60) Provisional application No. 61/508,337, filed on Jul. 15, 2011.

(30) Foreign Application Priority Data

May 16, 2011 (JP) .................. 2011-109602

(51) Int. Cl.
| | | |
|---|---|---|
| *A61K 6/09* | (2006.01) | |
| *C07C 271/10* | (2006.01) | |
| *C07C 271/24* | (2006.01) | |
| *C07C 271/28* | (2006.01) | |
| *C07C 271/34* | (2006.01) | |
| *C07C 271/38* | (2006.01) | |
| *C08L 33/08* | (2006.01) | |
| *C07C 271/36* | (2006.01) | |
| *C08G 18/67* | (2006.01) | |
| *C08G 18/75* | (2006.01) | |
| *C08G 18/76* | (2006.01) | |
| *C08G 18/00* | (2006.01) | |

(52) U.S. Cl.
CPC .............. *A61K 6/09* (2013.01); *C07C 271/10* (2013.01); *C07C 271/24* (2013.01); *C07C 271/28* (2013.01); *C07C 271/34* (2013.01); *C07C 271/36* (2013.01); *C07C 271/38* (2013.01); *C08G 18/003* (2013.01); *C08G 18/672* (2013.01); *C08G 18/755* (2013.01); *C08G 18/758* (2013.01); *C08G 18/7621* (2013.01); *C08G 18/7671* (2013.01); *C08L 33/08* (2013.01); *C07C 2101/14* (2013.01); *C07C 2103/66* (2013.01)

(58) Field of Classification Search
CPC .... C07C 271/24; C07C 271/10; C08L 33/08
See application file for complete search history.

(56) References Cited

U.S. PATENT DOCUMENTS

| | | | |
|---|---|---|---|
| 4,323,348 A | 4/1982 | Schmitz-Josten et al. | |
| 4,614,705 A | 9/1986 | Umehara | |
| 5,763,622 A * | 6/1998 | Podszun et al. | ............. 549/229 |
| 5,849,270 A | 12/1998 | Podszun et al. | |
| 2005/0118380 A1 | 6/2005 | Hirata et al. | |
| 2007/0142495 A1 | 6/2007 | Neffgen et al. | |
| 2010/0307378 A1* | 12/2010 | Trujillo-Lemon | ..... A61K 6/083 106/35 |
| 2012/0129973 A1* | 5/2012 | Sun | ....................... A61K 6/0088 523/115 |
| 2012/0296003 A1 | 11/2012 | Naruse et al. | |

FOREIGN PATENT DOCUMENTS

| | | |
|---|---|---|
| JP | 56-026809 | 3/1981 |
| JP | 60-171648 | 9/1985 |
| JP | 62-013307 | 1/1987 |
| JP | 63-063757 | 3/1988 |
| JP | 9-176151 | 7/1997 |
| JP | 9-216924 | 8/1997 |
| JP | 2003-263780 | 9/2003 |
| JP | 2005-89312 A | 4/2005 |
| JP | 2005-187385 A | 7/2005 |
| JP | 2007-15946 A | 1/2007 |
| JP | 2007-526270 A | 9/2007 |
| JP | 2007-277308 | 10/2007 |
| JP | 2008-24724 A | 2/2008 |
| JP | 2008-195754 | 8/2008 |
| JP | 2009-179596 A | 8/2009 |
| WO | WO 2012/157566 A1 | 11/2012 |

OTHER PUBLICATIONS

Watanabe, T., "Effect of Filler Particle Size on the Cure Depth of Light-Cured Composite Resins", Journal of Fukuoka Dental College, vol. 19, No. 1, pp. 11-24 (1992).
Kawaguchi, M., "Development of New Dental Resin Materials—Relationship Between the Structure and Physical Properties of Urethane Dimethacrylate Polymers-", The Journal of Japanese Society for Dental Materials and Devices, vol. 7, No. 2, pp. 143-158 (1988).
Office Action issued on Aug. 4, 2014, by the Chinese Patent Office in corresponding Chinese Patent Application No. 201280019842.0. (6 pages).

* cited by examiner

*Primary Examiner* — Paul A Zucker
(74) *Attorney, Agent, or Firm* — Buchanan, Ingersoll & Rooney PC

(57) ABSTRACT

The present invention provides a novel compound and a composition including the compound that exhibit small polymerization shrinkage particularly during curing and are producible at low cost on the industrial scale. The compound of the present invention is represented by Formula (1):

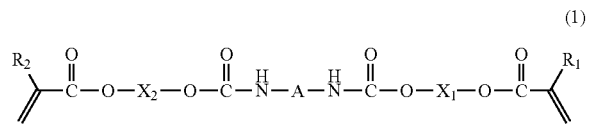

18 Claims, 16 Drawing Sheets

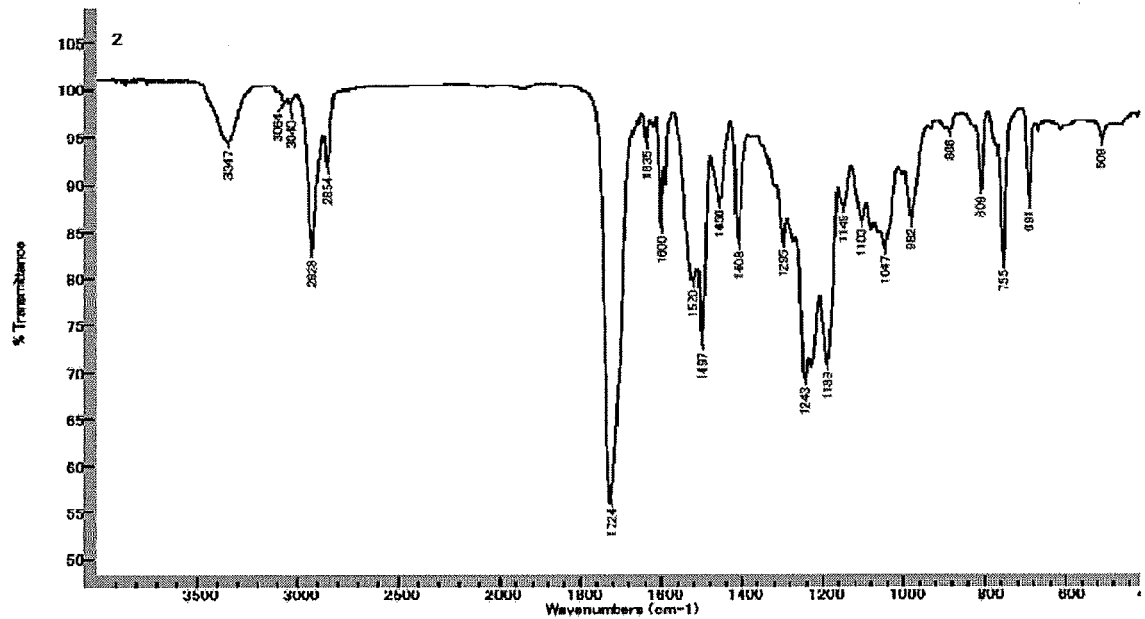
Fig. 1 FT-IR spectrum of product containing urethane (meth)acrylic compound obtained in Production Example 1
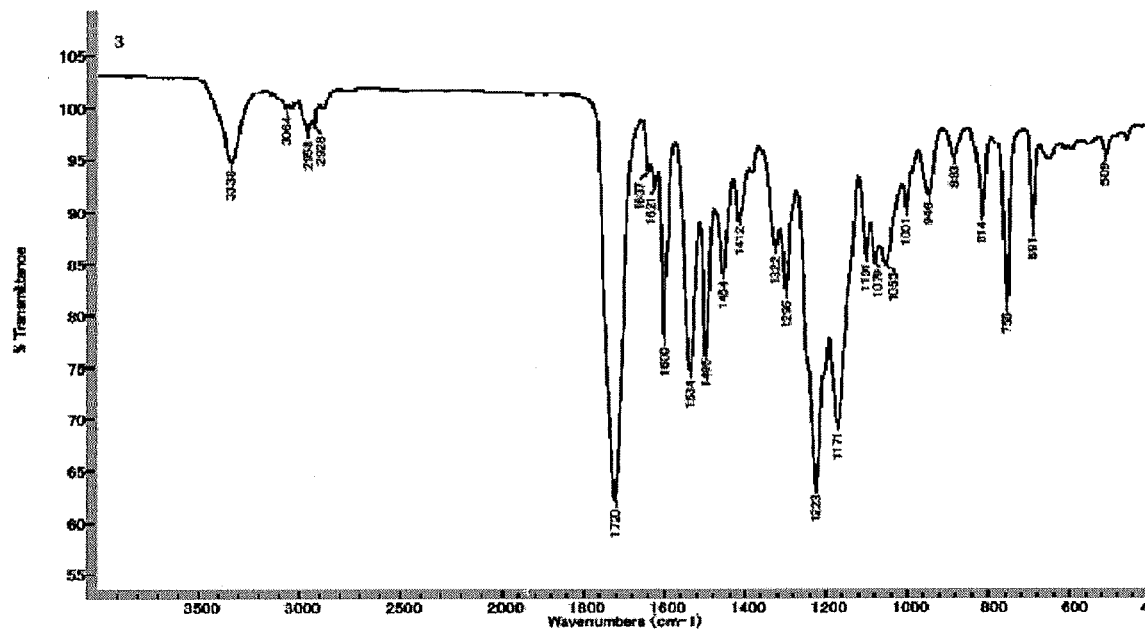
Fig. 2 FT-IR spectrum of product containing urethane (meth)acrylic compour obtained in Production Example 2

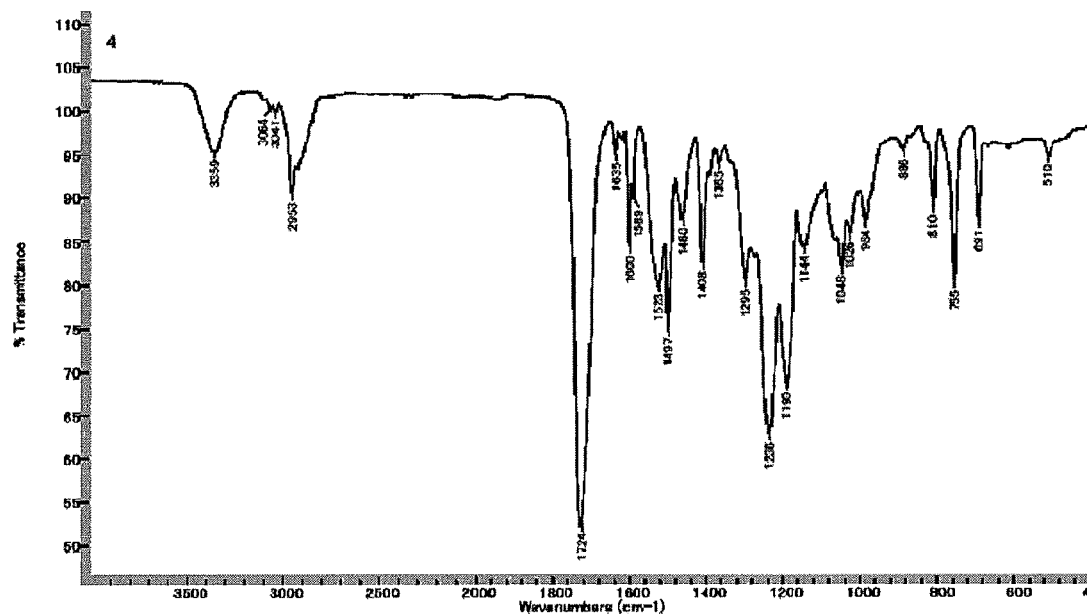
Fig. 3 FT-IR spectrum of product containing urethane (meth)acrylic compound obtained in Production Example 3
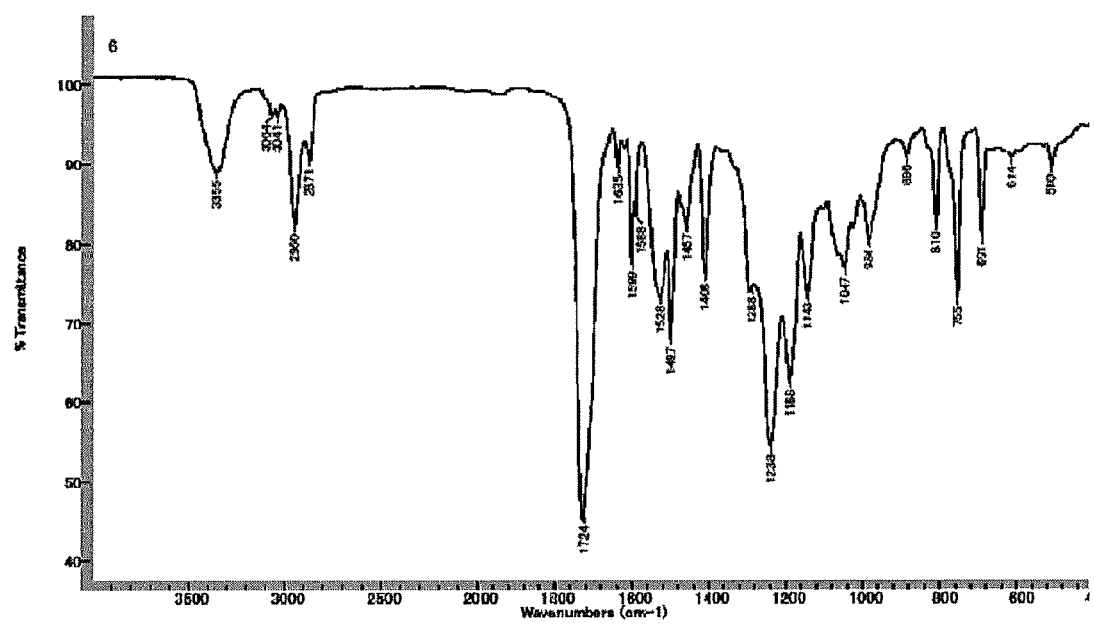
Fig. 4 FT-IR spectrum of product containing urethane (meth)acrylic compound obtained in Production Example 4

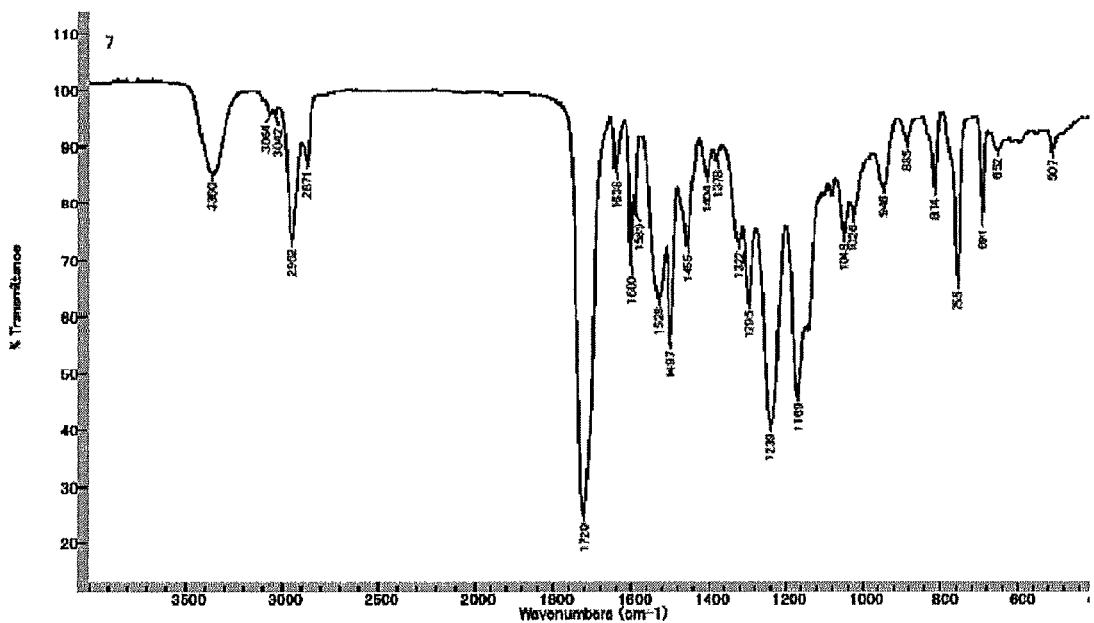
Fig. 5  FT-IR spectrum of product containing urethane (meth)acrylic compound obtained in Production Example 5
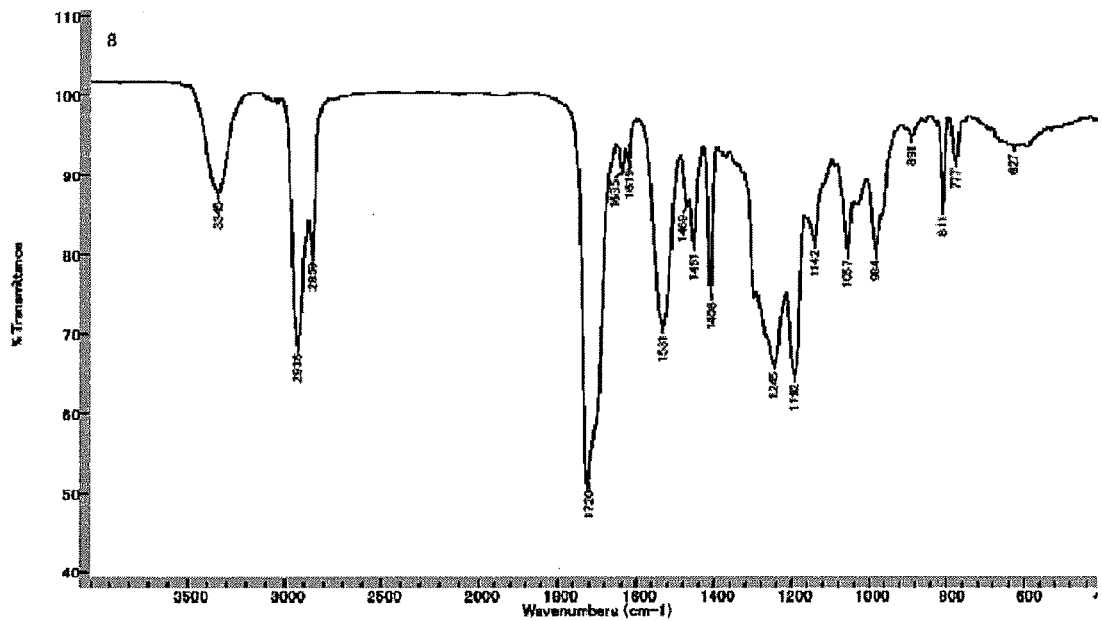
Fig. 6  FT-IR spectrum of product containing urethane (meth)acrylic compound obtained in Production Example 6

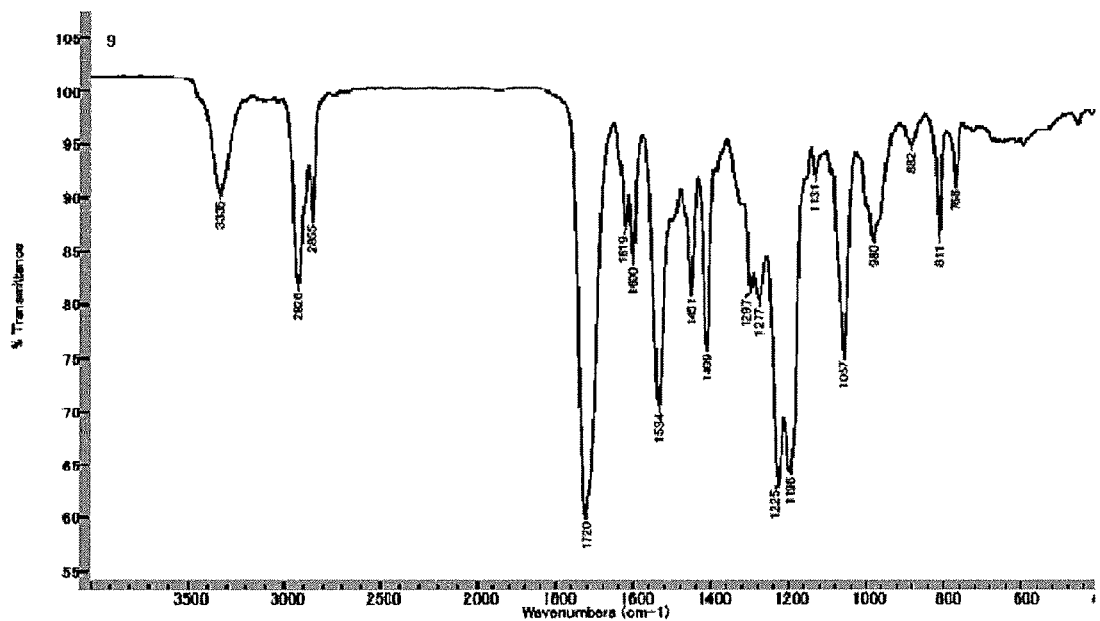
Fig. 7  FT-IR spectrum of product containing urethane (meth)acrylic compound obtained in Production Example 7
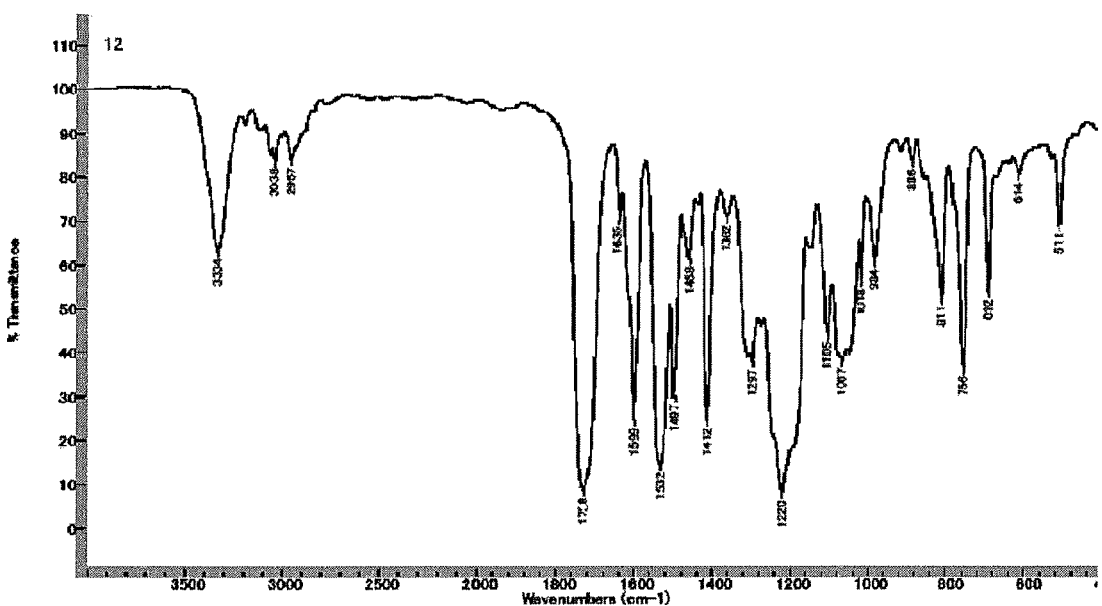
Fig. 8  FT-IR spectrum of product containing urethane (meth)acrylic compound obtained in Production Example 8

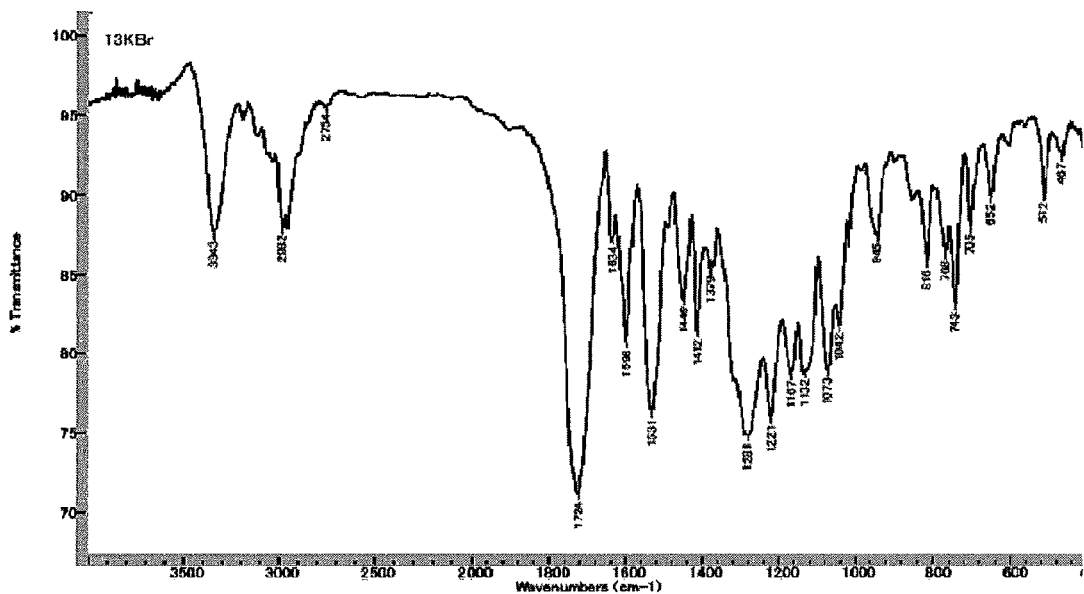
Fig. 9 FT-IR spectrum of product containing urethane (meth)acrylic compound obtained in Production Example 9
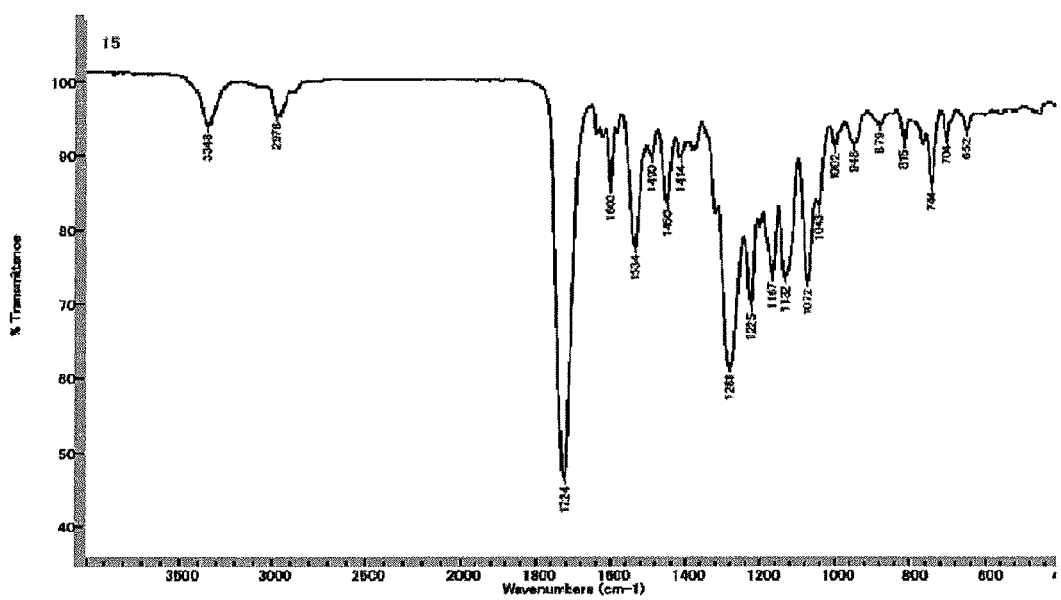
Fig. 10 FT-IR spectrum of product containing urethane (meth)acrylic compound obtained in Production Example 10

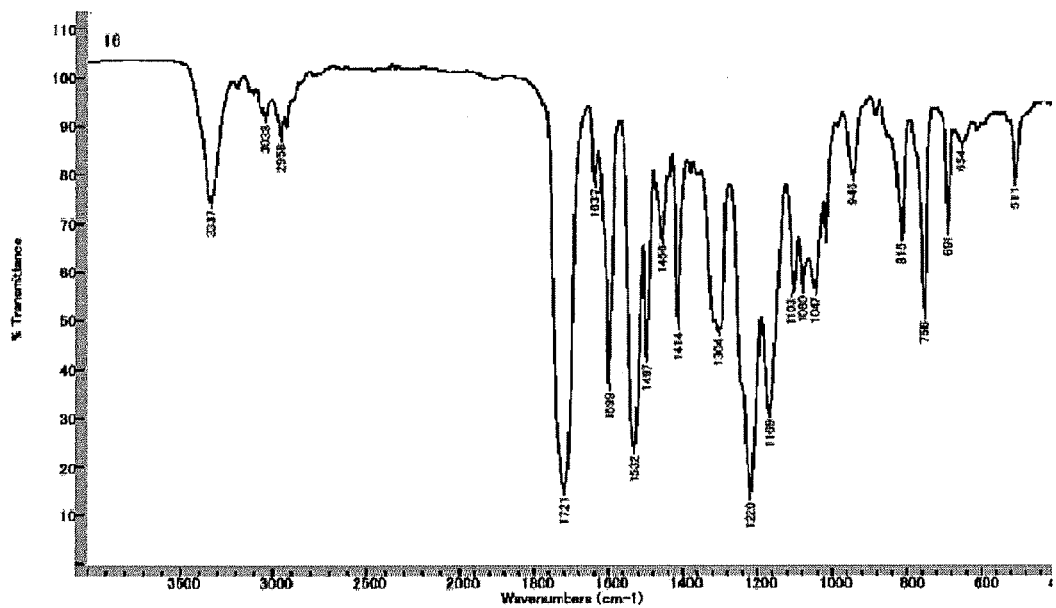
Fig. 11 FT-IR spectrum of product containing urethane (meth)acrylic compound obtained in Production Example 11
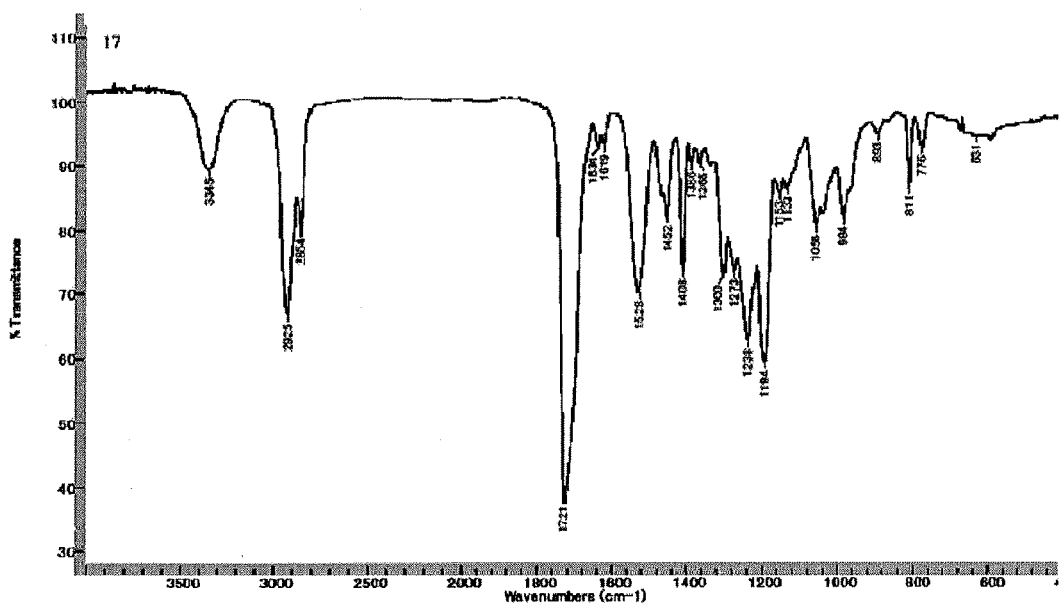
Fig. 12 FT-IR spectrum of product containing urethane (meth)acrylic compound obtained in Production Example 12

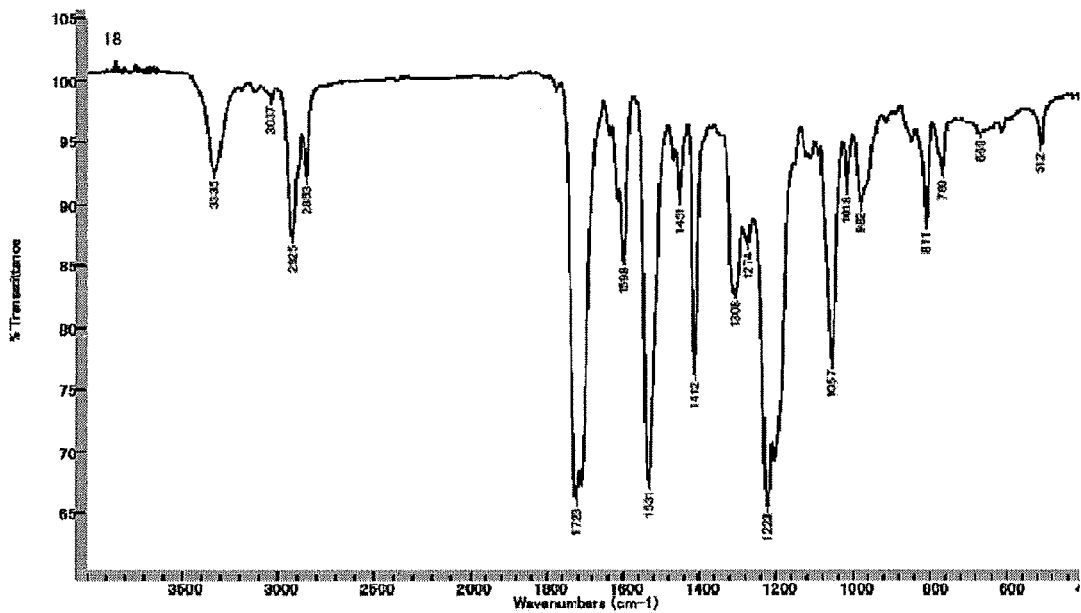
Fig. 13  FT-IR spectrum of product containing urethane (meth)acrylic compound obtained in Production Example 13
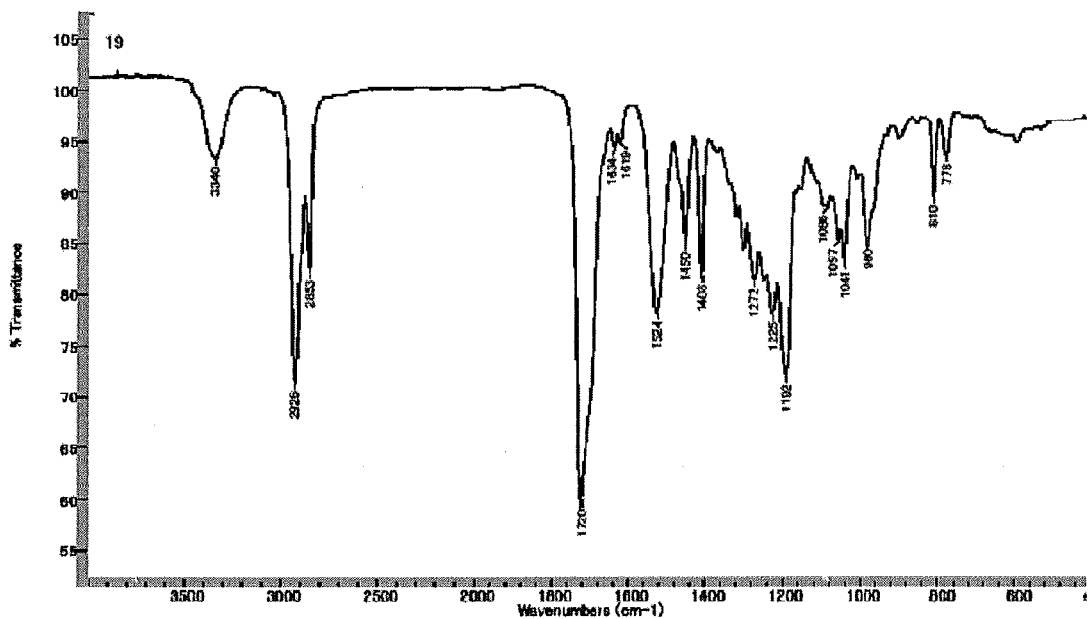
Fig. 14  FT-IR spectrum of product containing urethane (meth)acrylic compound obtained in Production Example 14

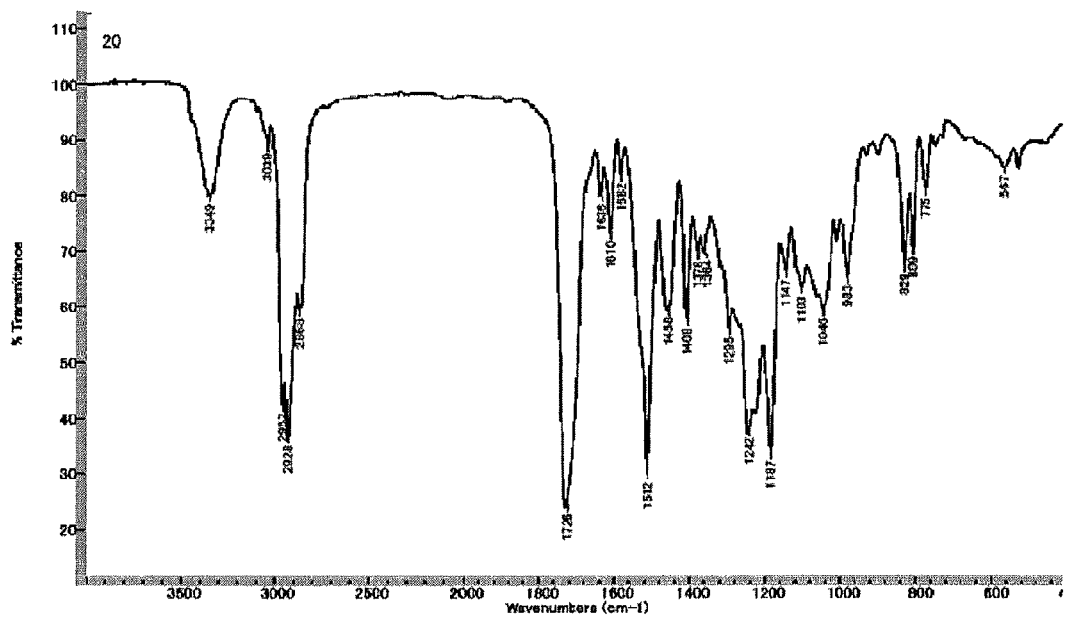
Fig. 15 FT-IR spectrum of product containing urethane (meth)acrylic compound obtained in Production Example 15
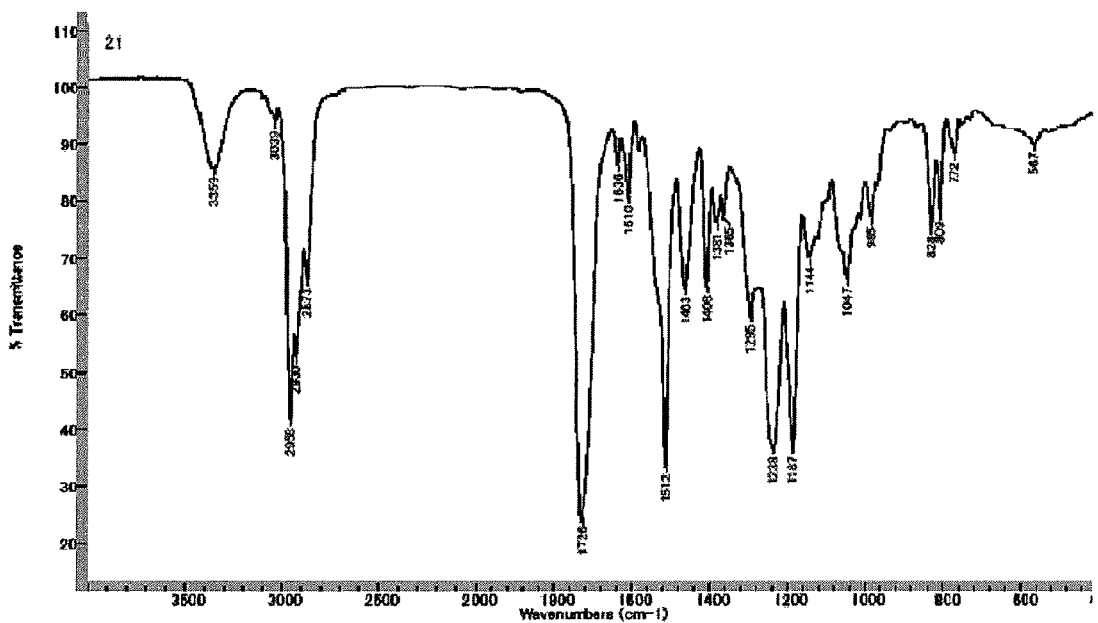
Fig. 16 FT-IR spectrum of product containing urethane (meth)acrylic compound obtained in Production Example 16

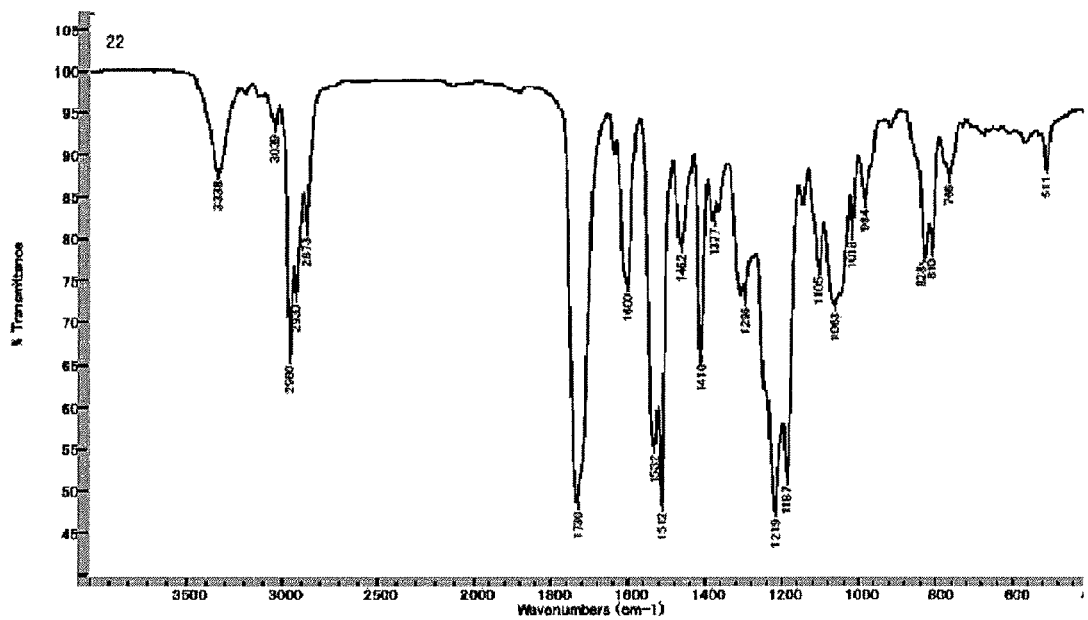
Fig. 17 FT-IR spectrum of product containing urethane (meth)acrylic compound obtained in Production Example 17
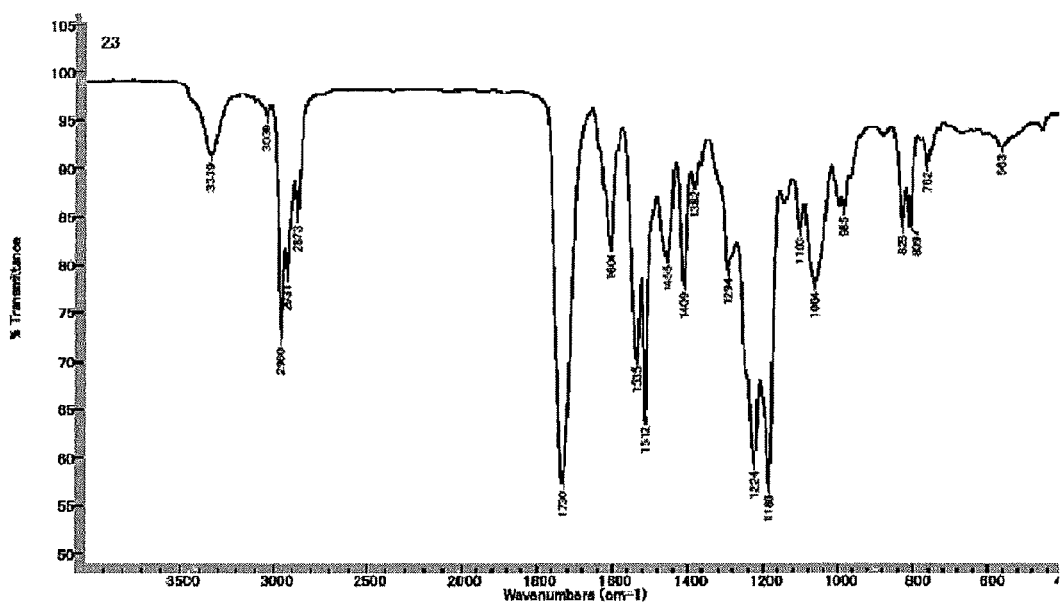
Fig. 18 FT-IR spectrum of product containing urethane (meth)acrylic compound obtained in Production Example 18

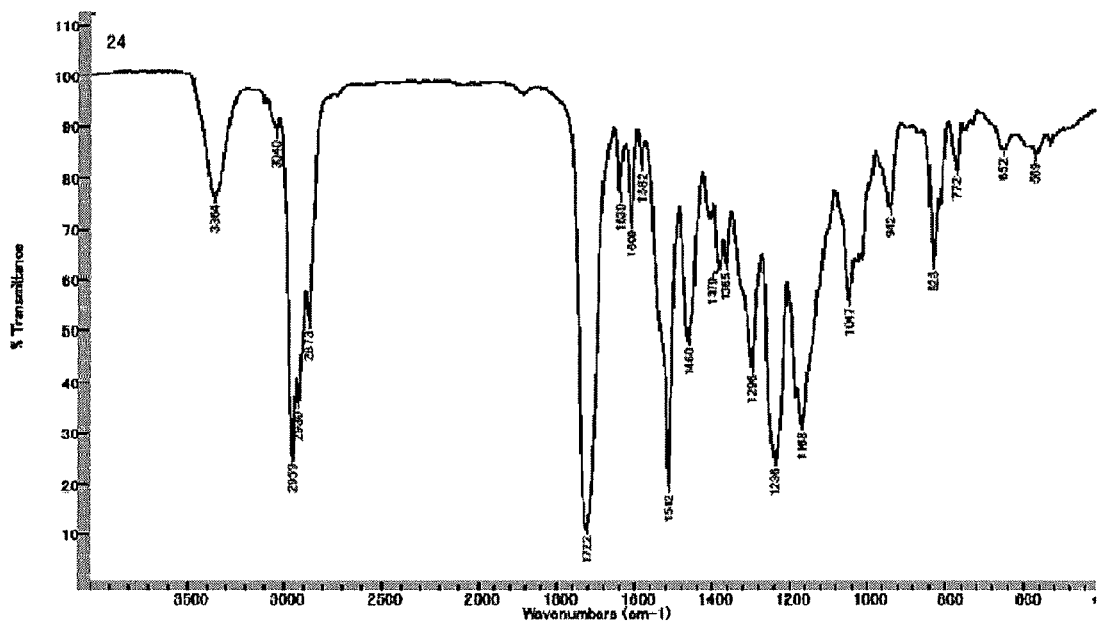
Fig. 19 FT-IR spectrum of product containing urethane (meth)acrylic compound obtained in Production Example 19
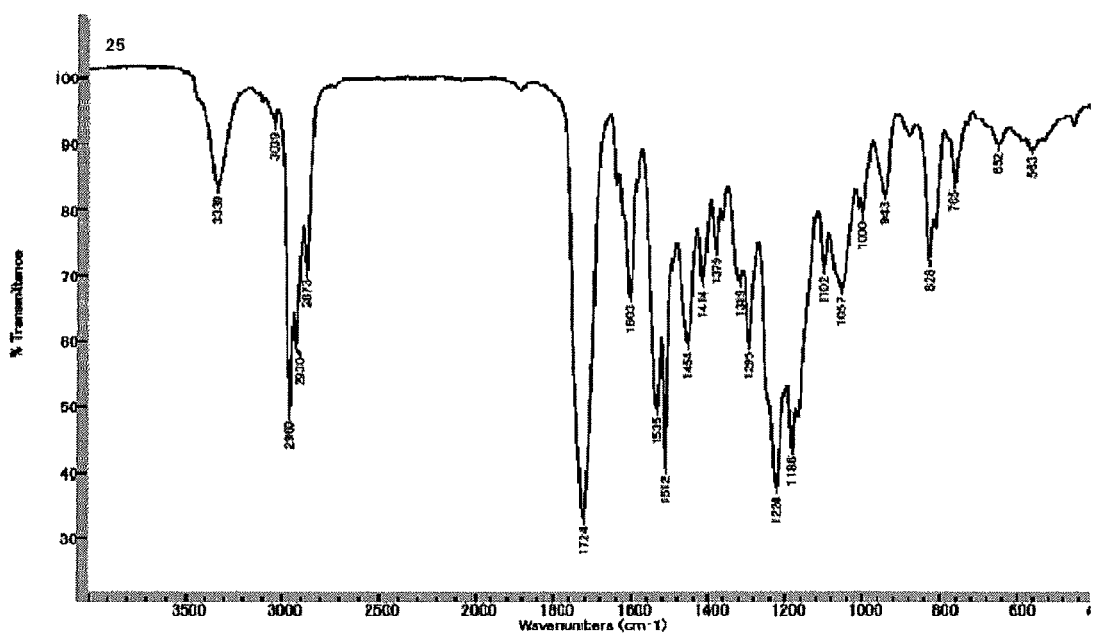
Fig. 20 FT-IR spectrum of product containing urethane (meth)acrylic compound obtained in Production Example 20

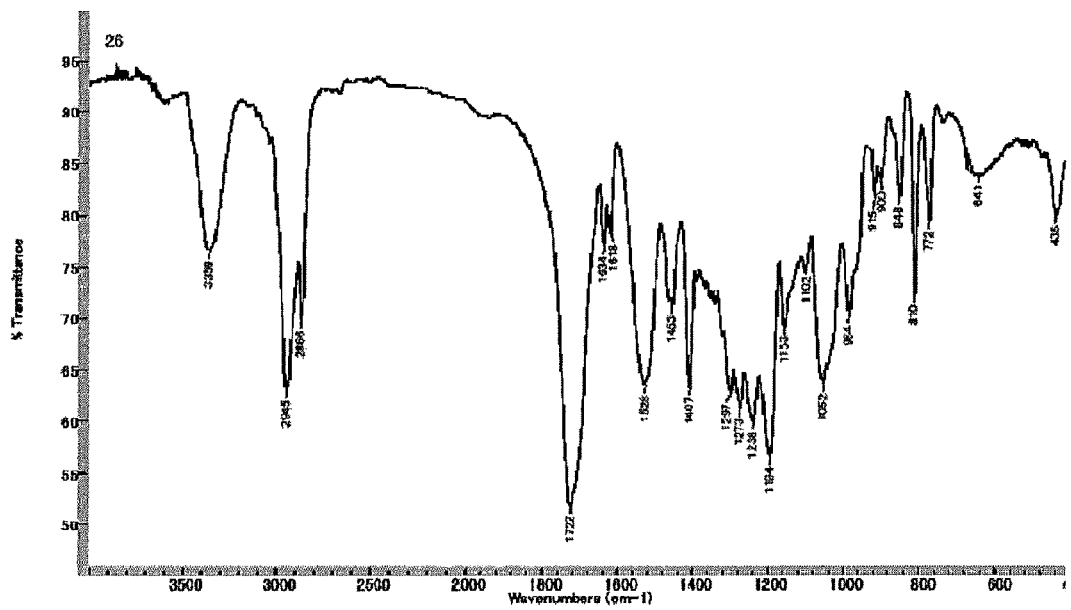
Fig. 21  FT-IR spectrum of product containing urethane (meth)acrylic compound obtained in Production Example 21
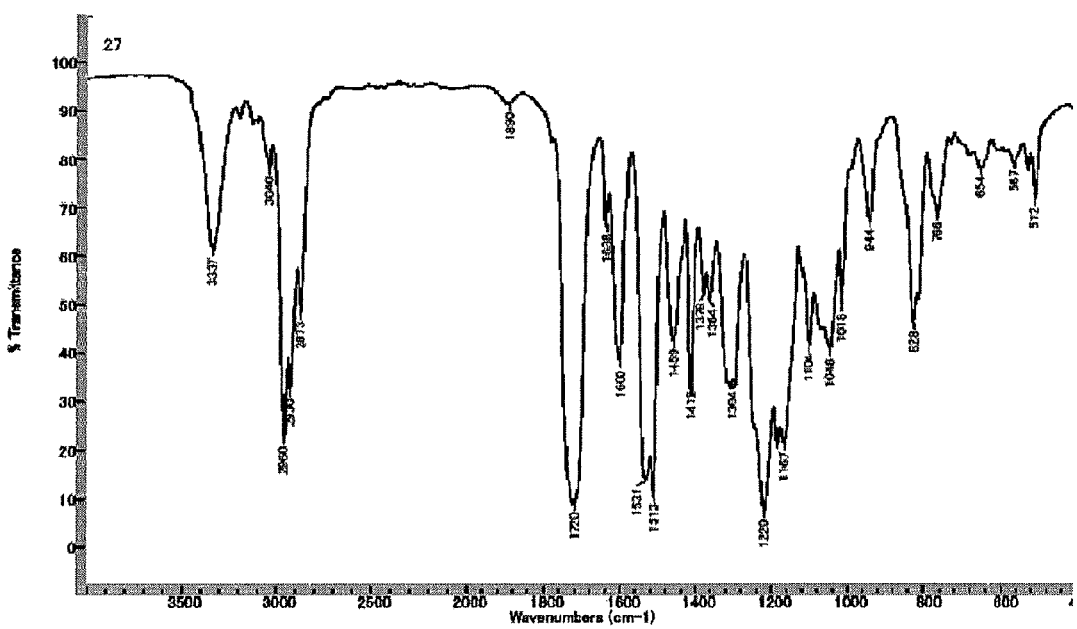
Fig. 22  FT-IR spectrum of product containing urethane (meth)acrylic compound obtained in Production Example 22

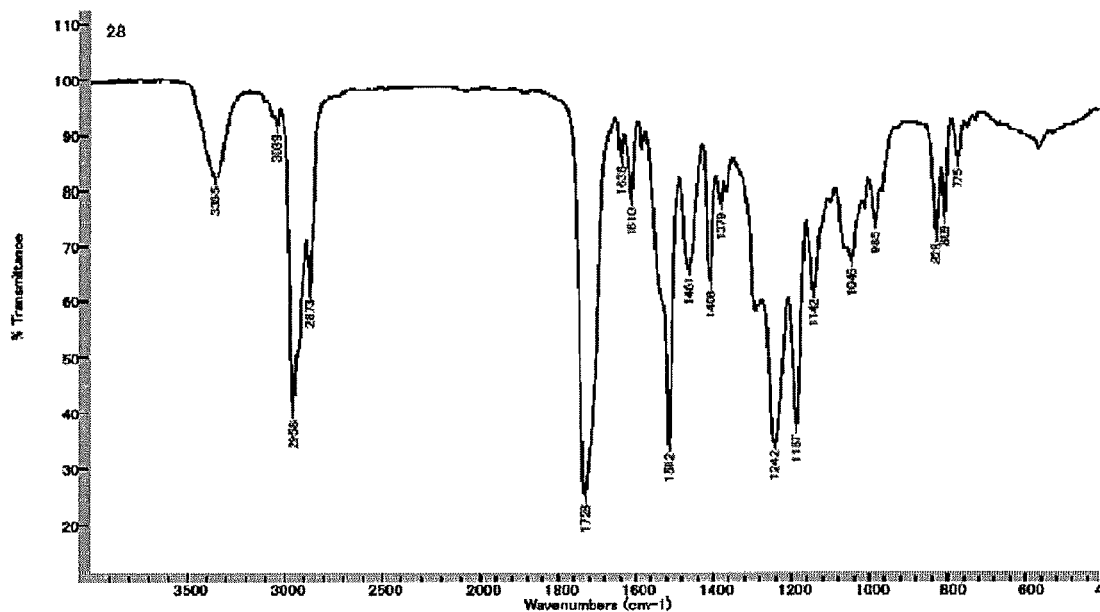
Fig. 23  FT-IR spectrum of product containing urethane (meth)acrylic compound obtained in Production Example 23
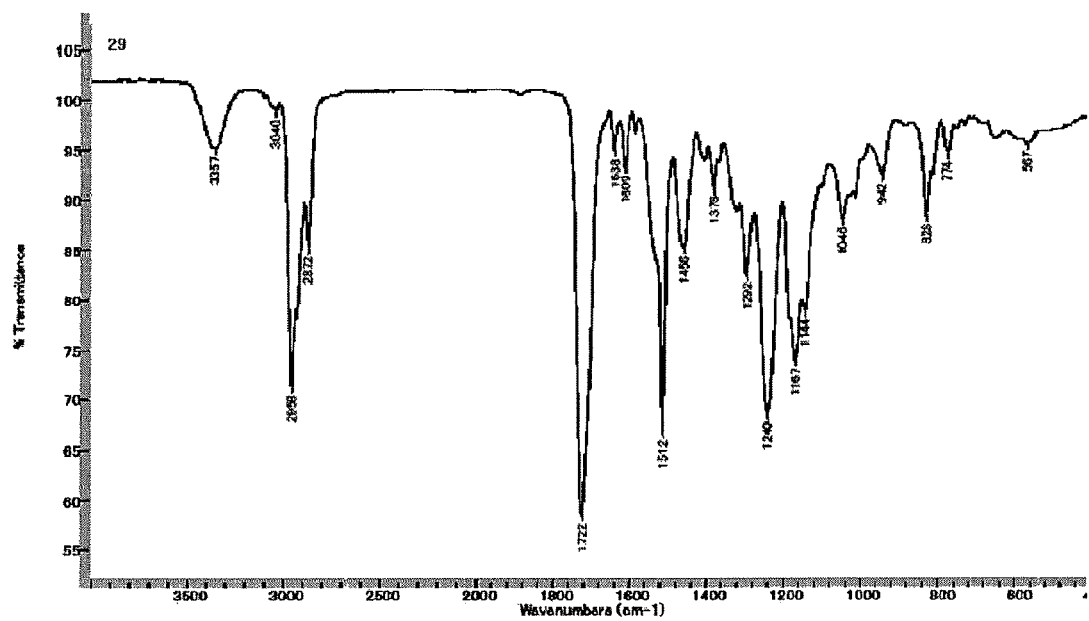
Fig. 24  FT-IR spectrum of product containing urethane (meth)acrylic compound obtained in Production Example 24

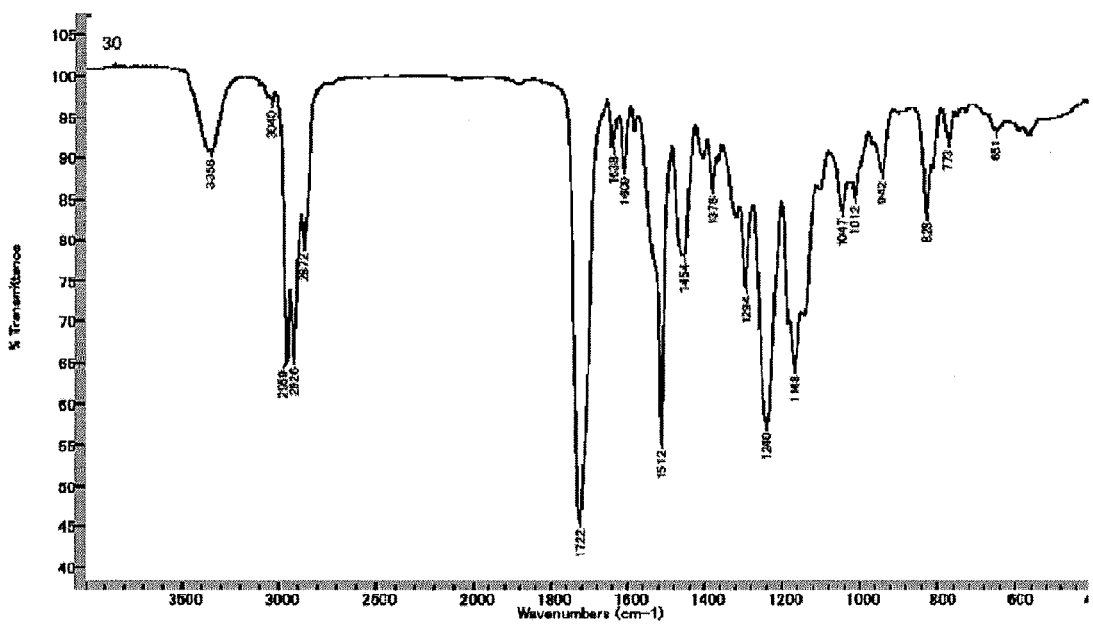
Fig. 25 FT-IR spectrum of product containing urethane (meth)acrylic compound obtained in Production Example 25
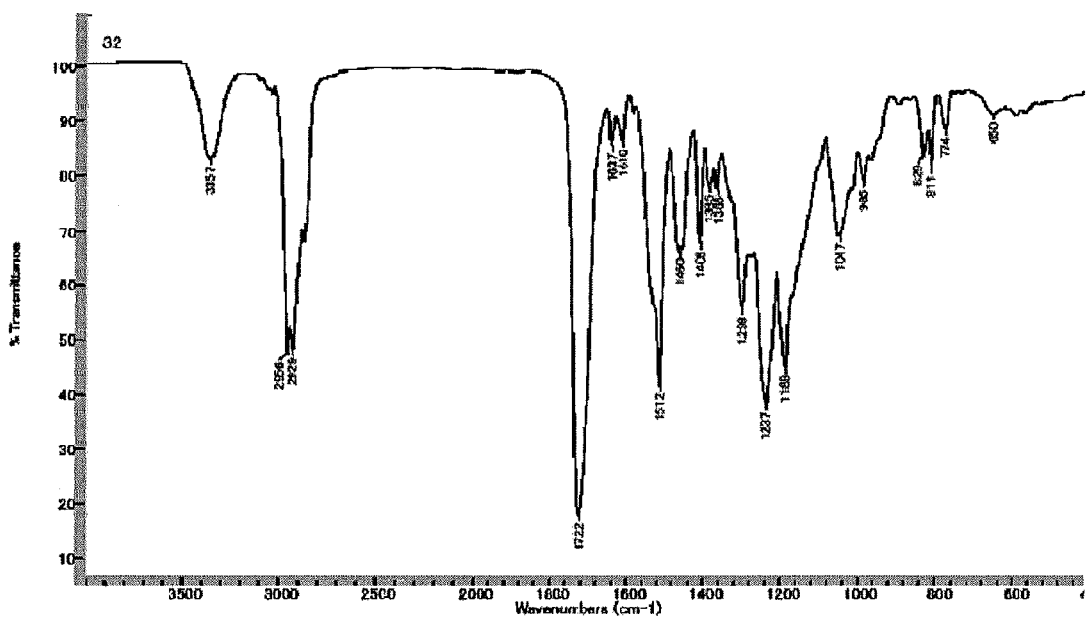
Fig. 26 FT-IR spectrum of product containing urethane (meth)acrylic compound obtained in Production Example 26

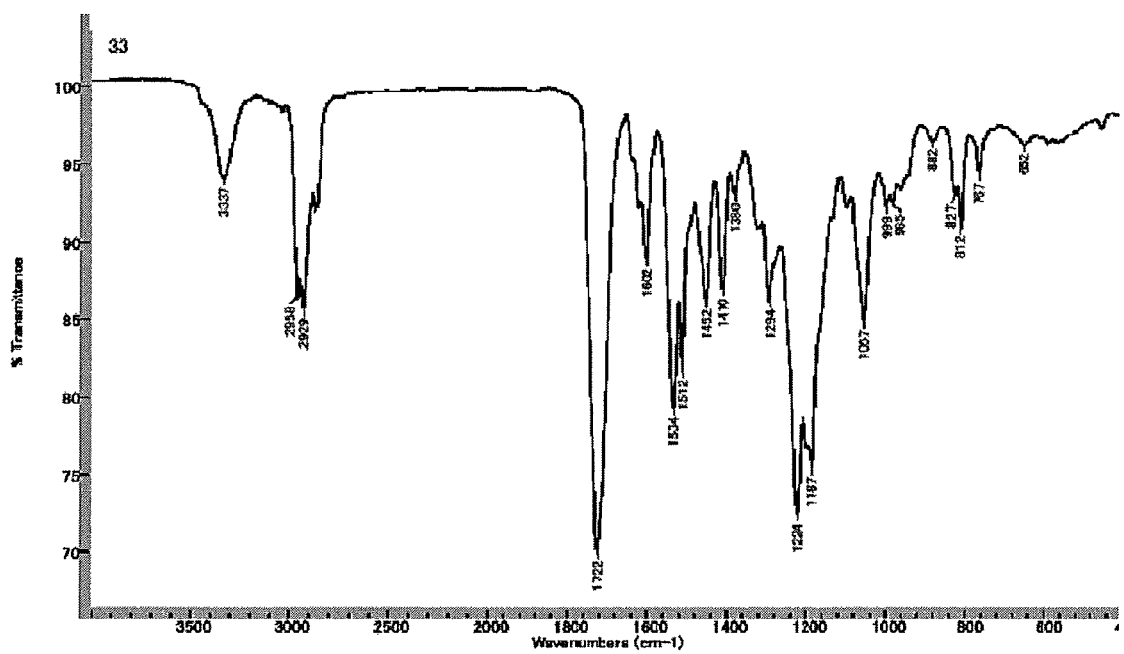
Fig. 27 FT-IR spectrum of product containing urethane (meth)acrylic compound obtained in Production Example 27
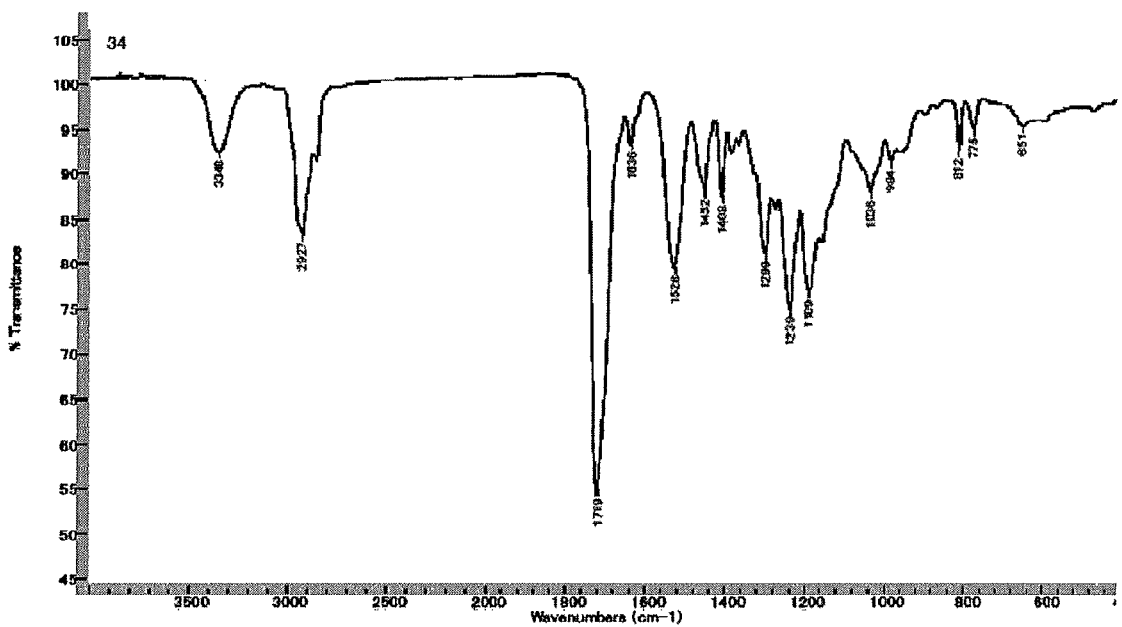
Fig. 28 FT-IR spectrum of product containing urethane (meth)acrylic compound obtained in Production Example 28

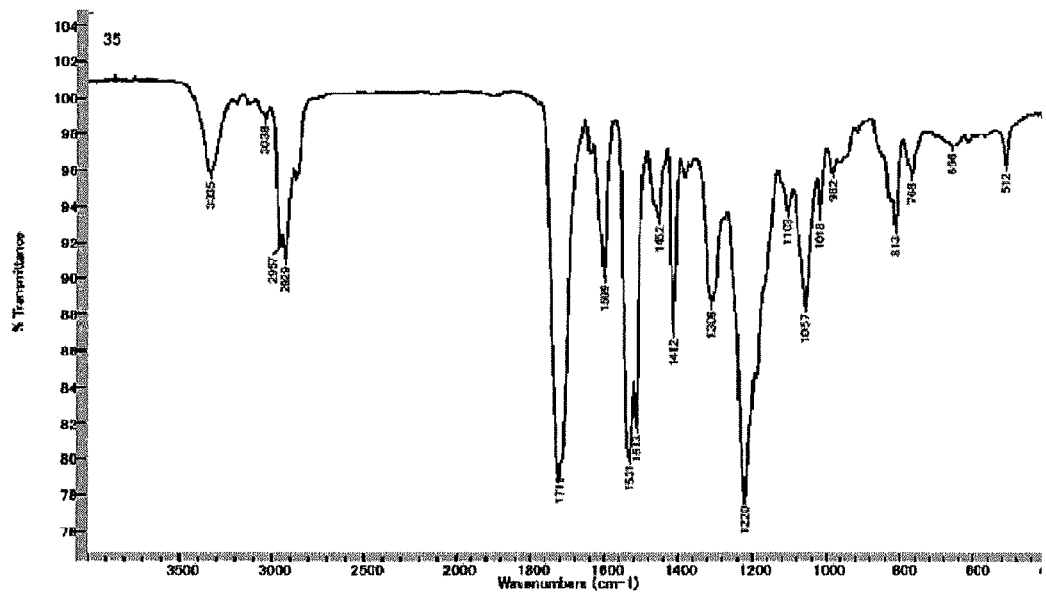
Fig. 29 FT-IR spectrum of product containing urethane (meth)acrylic compound obtained in Production Example 29
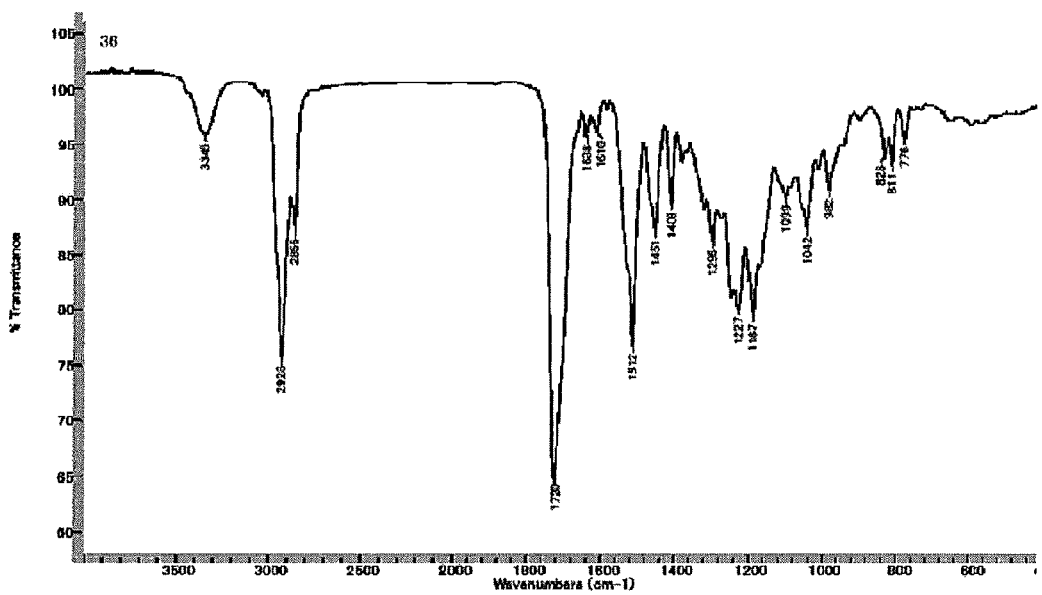
Fig. 30 FT-IR spectrum of product containing urethane (meth)acrylic compound obtained in Production Example 30

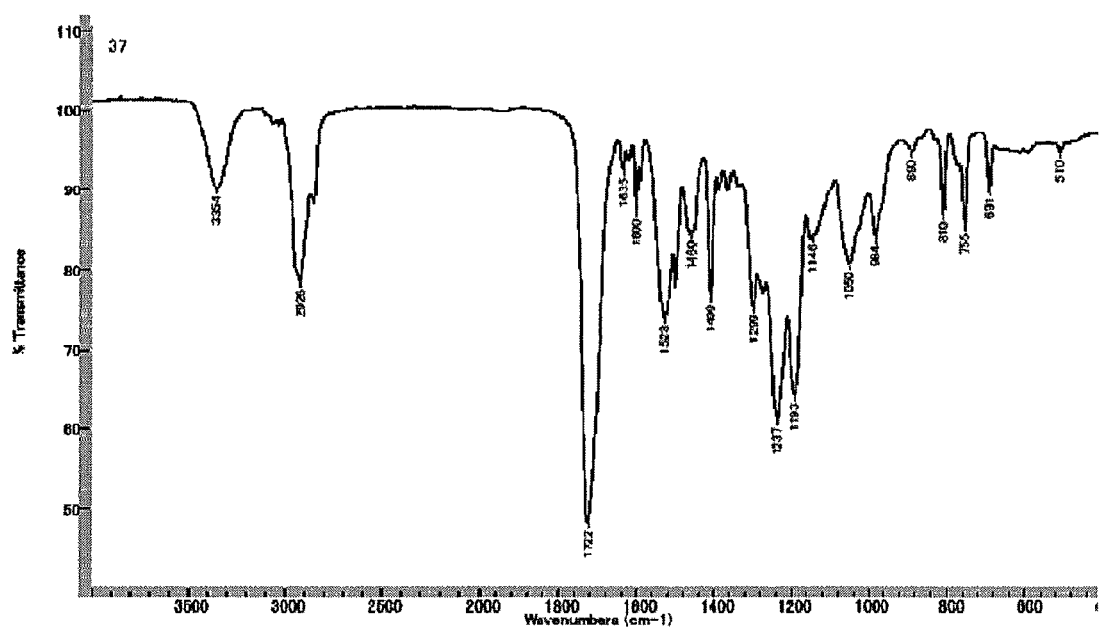
Fig. 31 FT-IR spectrum of product containing urethane (meth)acrylic compound obtained in Production Example 31

COMPOUND, COMPOSITION COMPRISING THE COMPOUND AND CURED PRODUCT

FIELD OF THE INVENTION

The present invention relates to a novel compound, a composition comprising the compound, and a cured product obtained by curing the compound or the composition.

DESCRIPTION OF THE RELATED ART

Radically polymerizable monomers represented by (meth)acrylates exhibit good properties such as high curing properties and transparency and are thus used widely in various fields including coating materials, plate making materials, optical materials and dental materials.

In the field of dental materials in particular, these monomers are widely used as dental restorative materials such as dental composite resins in order to restore natural teeth which have been damaged by caries or been fractured, as well as dental adhesives in order to bond a dental composite resin to a tooth, and artificial teeth and denture base materials.

In general, the dental composite resin is composed of a polymerizable monomer, a polymerization initiator and a filler. From the viewpoints of in-vivo safety as well as properties of cured products such as mechanical strength, abrasion resistance and aesthetic properties, a frequently used polymerizable monomer is a radically polymerizable polyfunctional (meth)acrylate. Examples of such polyfunctional (meth)acrylates include 2,2-bis[4-(3-methacryloyloxy-2-hydroxypropoxy)phenyl]propane (generally referred to as Bis-GMA) and 2,2,4-trimethylhexamethylene bis(2-carbamoyloxyethyl)dimethacrylate (generally referred to as UDMA).

However, in general, the radically polymerizable monomers, due to its curing mechanism, has a large polymerization shrinkage and a high viscosity, and thus has a problem in terms of operation properties particularly during curing.

Furthermore, clinical professionals have pointed out that dental composite resins should be improved in terms of properties of cured products such as flexural strength, elastic modulus and abrasion resistance as well as reduced in terms of water absorption, discoloration and polymerization shrinkage during curing, and transparency and aesthetic properties as good as natural teeth.

In order to reduce polymerization shrinkage, it has been proposed to use a ring-opening polymerizable epoxy or oxetane compound which generally has smaller polymerization shrinkage than acrylic compounds (Patent Literature 1 and Patent Literature 2). Although polymerization shrinkage tends to be reduced by the use of such compounds, problems remain such as the need of special primers due to different types of curing systems. Further, these compounds are unsatisfactory in terms of transparency and operation properties. Moreover, in the application to a dental field, for example, these compounds are unsatisfactory in terms of e.g., aesthetic properties.

It is also proposed to reduce polymerization shrinkage by increasing the amount of filler (Patent Literature 3 and Patent Literature 4). However, effects obtained by this approach are limited because the monomers that are used have such a high volumetric shrinkage.

Further, low-shrinkage materials that use a silicon-containing (meth)acrylate are proposed (Patent Literature 5). However, the synthesis of these materials is complicated and is to be improved in order to realize industrial production.

Further, these materials are unsatisfactory in terms of mechanical strength of cured products.

In the application to the optical materials, if the radically polymerizable monomer having a large polymerization shrinkage is used for a transparent cover layer of an optical disk, a warpage easily occurs; in view of this problem, a (meth)acrylate having an alicyclic structure large in its steric hindrance has been proposed (Patent Literature 6). However, this material involves a complicated synthesis and is unsatisfactory in terms of operation properties and production on the industrial scale.

Thus, there has been a need for polymerizable monomers that have small polymerization shrinkage during curing, and for such polymerizable monomers and cured products that are producible at low cost on the industrial scale.

CITATION LIST

Patent Literatures

Patent Literature 1: JP-A-2007-15946
Patent Literature 2: JP-A-2005-187385
Patent Literature 3: JP-A-2007-526270
Patent Literature 4: JP-A-2005-89312
Patent Literature 5: JP-A-2009-179596
Patent Literature 6: JP-A-2008-24724

SUMMARY OF THE INVENTION

Problems to be Solved by the Invention

It is an object of the present invention to provide a novel compound and a composition comprising the compound that exhibit small polymerization shrinkage particularly during curing and an appropriate viscosity and are producible at low cost on the industrial scale, as well as to provide a cured product obtained by curing the compound or the composition.

In the present invention, the novel compound and the novel composition are also referred to as a "urethane(meth) acrylic compound" and a "urethane(meth)acrylic)acrylic compound composition", respectively.

Means for Solution

The present inventor carried out studies in order to achieve the above object and has found that the object is achieved with a novel urethane(meth)acrylic compound having at least one alicyclic structure or aromatic ring structure in the molecule. The present invention has been completed based on this finding.

A compound of the present invention is represented by Formula (1) described later.

A composition of the present invention includes the inventive compound.

A cured product of the present invention is obtained by curing the inventive compound or the inventive composition.

Advantageous Effects of the Invention

The urethane(meth)acrylic compound of the invention can give a cured product showing excellent mechanical strength, abrasion resistance, transparency, operation properties and safety, has a low polymerization shrinkage particularly at the time of polymerization curing, and exhibits a favorable and appropriate viscosity at the time of preparation of the composition. Thus, the urethane(meth)acrylic compound is suited for use in optical materials and dental materials requiring transparency, in particular dental restorative materials such as dental restorative composite resins used to fill cavities. The dental restorative materials which include the inventive urethane(meth)acrylic compound exhibit small polymerization shrinkage during curing and are unlikely to cause a contraction gap between the restoration and the bonding surface of a tooth, thereby reducing the probability of secondary caries, tooth pulp stimulation and the detachment of restorations.

The urethane(meth)acrylic compound of the present invention is relatively high in refractive index and has excellent transparency. Thus, the cured product comprising the urethane(meth)acrylic compound of the present invention is also relatively high in refractive index and has excellent transparency. Furthermore, in a dental application, the cured product is excellent in aesthetic properties.

BRIEF DESCRIPTION OF THE DRAWINGS

FIG. 1 is a FT-IR spectrum of a product that contains a urethane(meth)acrylic compound produced in Production Example 1;
FIG. 2 is a FT-IR spectrum of a product that contains a urethane(meth)acrylic compound produced in Production Example 2;
FIG. 3 is a FT-IR spectrum of a product that contains a urethane(meth)acrylic compound produced in Production Example 3;
FIG. 4 is a FT-IR spectrum of a product that contains a urethane(meth)acrylic compound produced in Production Example 4;
FIG. 5 is a FT-IR spectrum of a product that contains a urethane(meth)acrylic compound produced in Production Example 5;
FIG. 6 is a FT-IR spectrum of a product that contains a urethane(meth)acrylic compound produced in Production Example 6;
FIG. 7 is a FT-IR spectrum of a product that contains a urethane(meth)acrylic compound produced in Production Example 7;
FIG. 8 is a FT-IR spectrum of a product that contains a urethane(meth)acrylic compound produced in Production Example 8;
FIG. 9 is a FT-IR spectrum of a product that contains a urethane(meth)acrylic compound produced in Production Example 9;
FIG. 10 is a FT-IR spectrum of a product that contains a urethane(meth)acrylic compound produced in Production Example 10;
FIG. 11 is a FT-IR spectrum of a product that contains a urethane(meth)acrylic compound produced in Production Example 11;
FIG. 12 is a FT-IR spectrum of a product that contains a urethane(meth)acrylic compound produced in Production Example 12;
FIG. 13 is a FT-IR spectrum of a product that contains a urethane(meth)acrylic compound produced in Production Example 13;
FIG. 14 is a FT-IR spectrum of a product that contains a urethane(meth)acrylic compound produced in Production Example 14;
FIG. 15 is a FT-IR spectrum of a product that contains a urethane(meth)acrylic compound produced in Production Example 15;
FIG. 16 is a FT-IR spectrum of a product that contains a urethane(meth)acrylic compound produced in Production Example 16;
FIG. 17 is a FT-IR spectrum of a product that contains a urethane(meth)acrylic compound produced in Production Example 17;
FIG. 18 is a FT-IR spectrum of a product that contains a urethane(meth)acrylic compound produced in Production Example 18;
FIG. 19 is a FT-IR spectrum of a product that contains a urethane(meth)acrylic compound produced in Production Example 19;
FIG. 20 is a FT-IR spectrum of a product that contains a urethane(meth)acrylic compound produced in Production Example 20;
FIG. 21 is a FT-IR spectrum of a product that contains a urethane(meth)acrylic compound produced in Production Example 21;
FIG. 22 is a FT-IR spectrum of a product that contains a urethane(meth)acrylic compound produced in Production Example 22;
FIG. 23 is a FT-IR spectrum of a product that contains a urethane(meth)acrylic compound produced in Production Example 23;
FIG. 24 is a FT-IR spectrum of a product that contains a urethane(meth)acrylic compound produced in Production Example 24;
FIG. 25 is a FT-IR spectrum of a product that contains a urethane(meth)acrylic compound produced in Production Example 25;
FIG. 26 is a FT-IR spectrum of a product that contains a urethane(meth)acrylic compound produced in Production Example 26;
FIG. 27 is a FT-IR spectrum of a product that contains a urethane(meth)acrylic compound produced in Production Example 27;
FIG. 28 is a FT-IR spectrum of a product that contains a urethane(meth)acrylic compound produced in Production Example 28;
FIG. 29 is a FT-IR spectrum of a product that contains a urethane(meth)acrylic compound produced in Production Example 29;
FIG. 30 is a FT-IR spectrum of a product that contains a urethane(meth)acrylic compound produced in Production Example 30; and
FIG. 31 is a FT-IR spectrum of a product that contains a urethane(meth)acrylic compound produced in Production Example 31.

DESCRIPTION OF THE PREFERRED EMBODIMENTS

Novel Compounds (Urethane(Meth)Acrylic Compounds)

A novel urethane(meth)acrylic compound according to the present invention has at least one alicyclic or aromatic ring structure in the molecule and is represented by Formula (1). This specific urethane(meth)acrylic compound has a small polymerization shrinkage and excellent transparency and exhibits a favorable and appropriate viscosity at the time of preparation of the composition. Furthermore, this specific urethane(meth)acrylic compound has excellent operation properties, and is suited for use in dental restorative materials such as a composite resin. In the present invention, one, or two or more kinds of such urethane(meth)acrylic compounds may be contained as long as achieving the object of the invention.

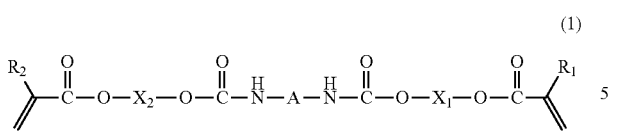

(1)

In Formula (1), $R_1$ and $R_2$ each independently indicate a hydrogen atom or a methyl group, A is a divalent organic group selected from the group consisting of structures (a) to (h) described below, $X_1$ and $X_2$ each indicate a divalent organic group, at least one of $X_1$ and $X_2$ is a divalent organic group selected from the group consisting of structures (i) to (m) described below, and the bonding sites in the structures (a) to (m) are indicated by the symbol "*":

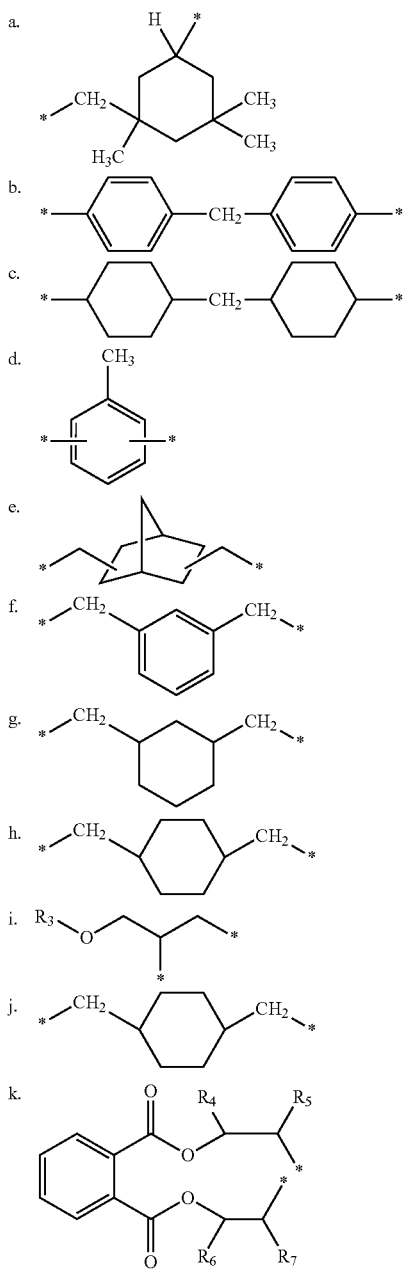

-continued

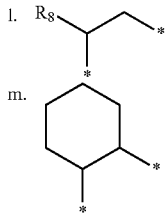

With respect to the organic groups (a) to (m), $R_3$ is an aryl group or a cycloalkyl group which may have a substituent, $R_4$, $R_5$, $R_6$ and $R_7$ each independently indicate a hydrogen atom or a methyl group, and $R_8$ is an alkyl group having 4 to 20 carbon atoms.

The compounds represented by Formula (1) exclude a compound in which A is the structure (c) or (d) and $X_1$ and $X_2$ are both the structures (i) in which $R_3$ is a phenyl group, and a compound in which A is the structure (a), $R_1$ and $R_2$ are both methyl groups and $X_1$ and $X_2$ are both the structures (i) in which $R_3$ is a phenyl group.

From the viewpoint of the reduction of polymerization shrinkage, it is preferable that the groups A, $X_1$ and $X_2$ in Formula (1) have two or more ring structures, and more preferably three or more ring structures.

In order to achieve a smaller polymerization shrinkage, it is preferable that the group A in Formula (1) be a divalent organic group selected from the group consisting of the structures (a), (b), (c), (d), (e) and (h).

It is preferable that the group A in Formula (1) be a divalent organic group selected from the group consisting of the structures (a), (c), (e), (f), (g) and (h). There is a tendency for such a compound to be unlikely to be colored when being formed into a cured product.

It is preferable that the group A in Formula (1) be a divalent organic group selected from the group consisting of the structures (a), (d), (e), (f), (g) and (h). Such a compound exhibits a favorable and more appropriate viscosity at the time of preparation of the composition and excellent operation properties.

It is more preferable that the group A in Formula (1) be a divalent organic group selected from the group consisting of the structures (a), (d), (e) and (h). Such a compound shows a smaller polymerization shrinkage and exhibits a favorable and appropriate viscosity at the time of preparation of the composition and excellent operation properties.

It is more preferable that the group A in Formula (1) be a divalent organic group selected from the group consisting of the structures (a), (c), (e) and (h). There is a tendency for such a compound to show a smaller polymerization shrinkage and to be unlikely to be colored when being formed into a cured product. It is also preferable that the group A be a divalent organic group selected from the group consisting of the structures (a), (e) and (h). In addition to the advantages described above, such a compound exhibits a favorable and appropriate viscosity at the time of preparation of the composition and excellent operation properties.

It is most preferable that the group A in Formula (1) be the structure (a). In addition to the advantageous effects described above, such a compound allows for exhibiting excellent transparency, thus being suited for e.g., optical materials, and is excellent in aesthetic properties in a dental use.

It is also preferable that at least one of $X_1$ and $X_2$ in Formula (1) be a divalent organic group selected from the group consisting of the structures (i), (j), (l) and (m). Such a compound exhibits a favorable and appropriate viscosity at the time of preparation of the composition and excellent operation properties.

It is preferable that one of $X_1$ and $X_2$ in Formula (1) be a divalent organic group selected from the group consisting of the structures (i), (j), (k) and (m). Such a compound is relatively high in refractive index. For example, such a compound tends to ensure that a urethane(meth)acrylic compound composition containing the urethane(meth)acrylic compound and a filler component is cured to give a transparent cured product having excellent aesthetic properties, and thus is preferred for optical materials use and dental use. It is preferable that one of $X_1$ and $X_2$ be a divalent organic group selected from the group consisting of the structures (i), (j) and (m). In addition to the advantageous effects described above, such a compound exhibits a favorable and appropriate viscosity at the time of preparation of the composition and excellent operation properties.

Further, it is preferable that $R_1$ and $R_2$ in Formula (1) be both hydrogen atoms. There is a tendency for such a compound to show a still smaller polymerization shrinkage.

It is preferable that in Formula (1), the group A be any of the structures (a), (b), (c) and (e), $X_1$ and $X_2$ be both the structures (i), and $R_1$ and $R_2$ be both hydrogen atoms. Such a compound shows a still smaller polymerization shrinkage.

It is preferable that in Formula (1), the group A be the structure (d), $X_1$ and $X_2$ be both the structures (i), and $R_1$ and $R_2$ be both methyl groups. Such a compound shows a still smaller polymerization shrinkage.

In the case where one of $X_1$ and $X_2$ in Formula (1) is an alkylene group of 1 to 4 carbon atoms such as methylene group or ethylene group, the polymerization shrinkage during curing tends to be relatively large. Thus, the use of such a compound is not preferable.

The urethane(meth)acrylic compounds of the present invention are not particularly limited as long as the compounds are represented by Formula (1). Examples of such compounds include compounds Nos. 1-1 to 9-6 illustrated in Tables 1 to 9. Any isomers of the illustrated compounds are within the scope of the invention. In the illustrations, $C_9$ indicates a nonyl group selected from all kinds of nonyl isomers.

TABLE 1

| Compound No. | Structural formula |
|---|---|
| 1-1 | |
| 1-2 | |
| 1-3 | |

TABLE 1-continued
| Compound No. | Structural formula |
|---|---|
| 1-4 | 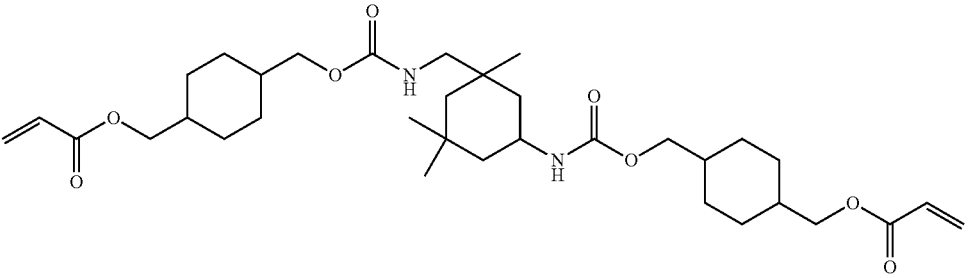 [SMILES: C=CC(=O)OCC1CCC(COC(=O)NCC2(C)CC(NC(=O)OCC3CCC(COC(=O)C=C)CC3)CC(C)(C)C2)CC1] |
| 1-5 | 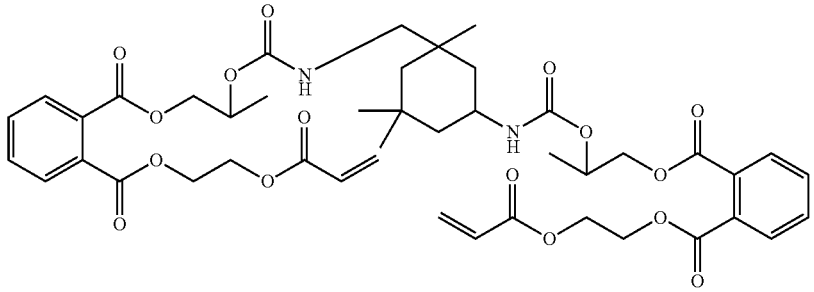 [SMILES: C=CC(=O)OCCOC(=O)c1ccccc1C(=O)OCC(C)OC(=O)NCC1(C)CC(NC(=O)OC(C)COC(=O)c2ccccc2C(=O)OCCOC(=O)C=C)CC(C)(C)C1] |
| 1-6 | 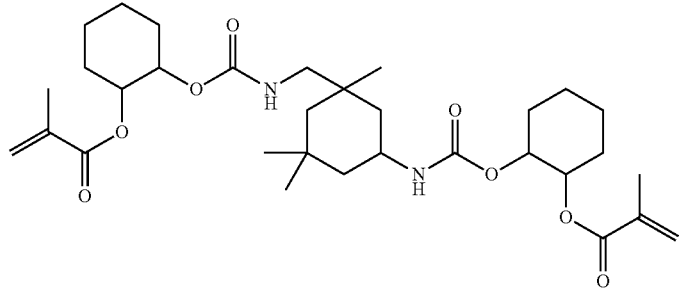 [SMILES: C=C(C)C(=O)OC1CCCCC1OC(=O)NCC1(C)CC(NC(=O)OC2CCCCC2OC(=O)C(=C)C)CC(C)(C)C1] |
| 1-7 | 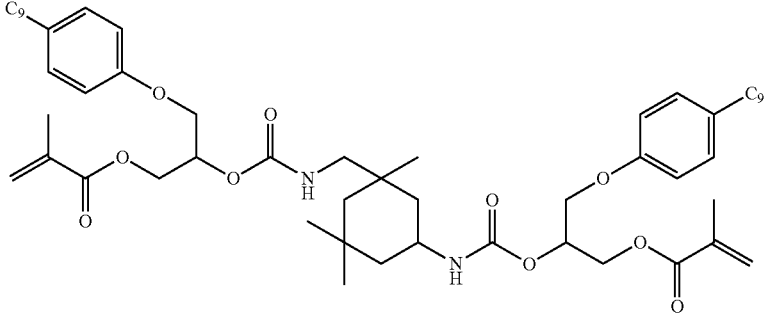 |
| 1-8 | 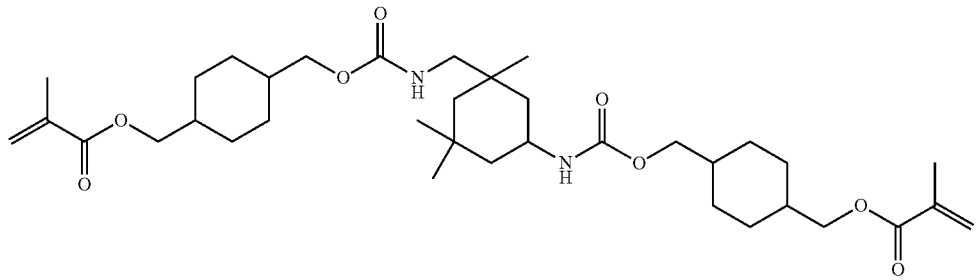 [SMILES: C=C(C)C(=O)OCC1CCC(COC(=O)NCC2(C)CC(NC(=O)OCC3CCC(COC(=O)C(=C)C)CC3)CC(C)(C)C2)CC1] |

TABLE 1-continued

| Compound No. | Structural formula |
|---|---|
| 1-9 | (structure) |

TABLE 2

| Compound No. | Structural formula |
|---|---|
| 2-1 | (structure) |
| 2-2 | (structure) |
| 2-3 | (structure) |
| 2-4 | (structure) |

TABLE 2-continued
| Compound No. | Structural formula |
|---|---|
| 2-5 | 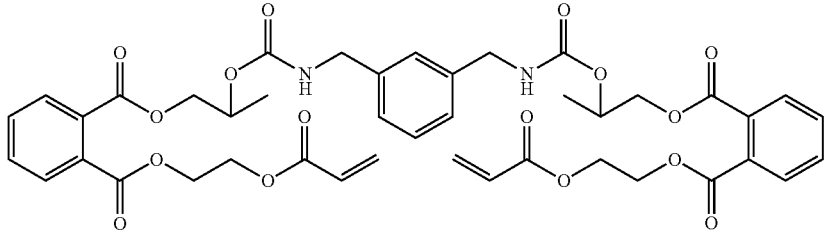 [SMILES: C=CC(=O)OCCOC(=O)c1ccccc1C(=O)OCC(C)OC(=O)NCc1cccc(CNC(=O)OC(C)COC(=O)c2ccccc2C(=O)OCCOC(=O)C=C)c1] |
| 2-6 | 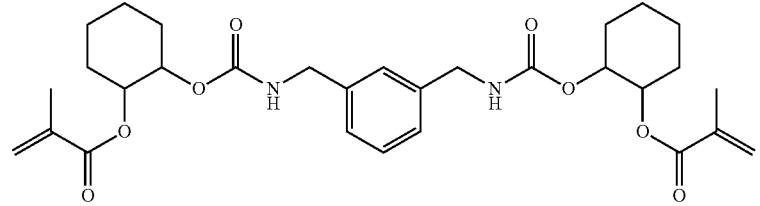 [SMILES: C=C(C)C(=O)OC1CCCCC1OC(=O)NCc1cccc(CNC(=O)OC2CCCCC2OC(=O)C(=C)C)c1] |
| 2-7 | 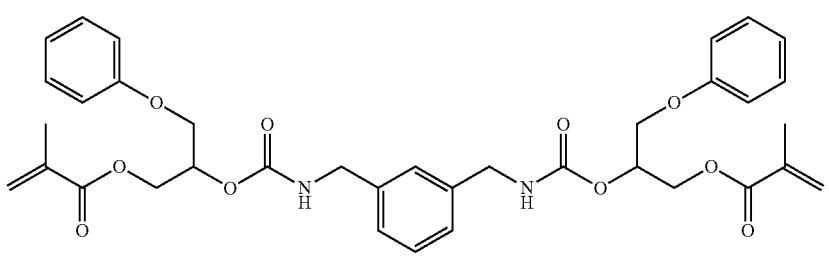 [SMILES: C=C(C)C(=O)OCC(COc1ccccc1)OC(=O)NCc1cccc(CNC(=O)OC(COC(=O)C(=C)C)COc2ccccc2)c1] |
| 2-8 | 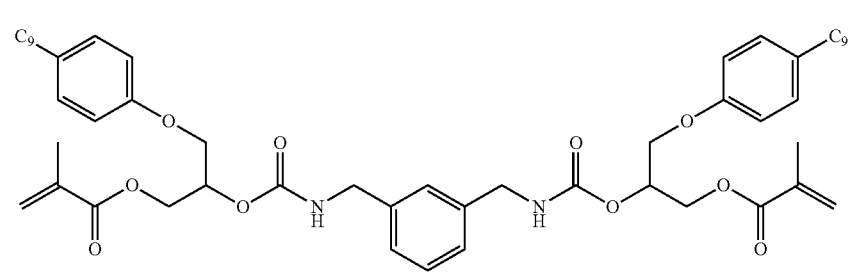 |
| 2-9 | 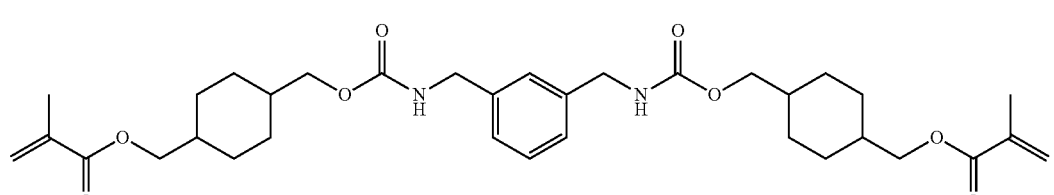 |
| 2-10 | 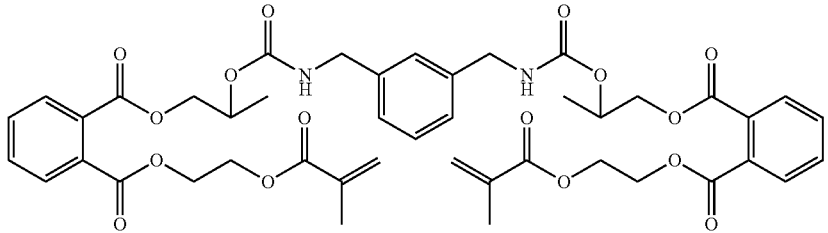 [SMILES: C=C(C)C(=O)OCCOC(=O)c1ccccc1C(=O)OCC(C)OC(=O)NCc1cccc(CNC(=O)OC(C)COC(=O)c2ccccc2C(=O)OCCOC(=O)C(=C)C)c1] |

TABLE 3

| Compound No. | Structural formula |
|---|---|
| 3-1 | |
| 3-2 | |
| 3-3 | |
| 3-4 | |
| 3-5 | |
| 3-6 | |

TABLE 3-continued

| Compound No. | Structural formula |
|---|---|
| 3-7 | |
| 3-8 | |
| 3-9 | |
| 3-10 | |

TABLE 4

| Compound No. | Structural formula |
|---|---|
| 4-1 | |
| 4-2 | |

TABLE 4-continued

| Compound No. | Structural formula |
|---|---|
| 4-3 | |
| 4-4 | |
| 4-5 | |
| 4-6 | |
| 4-7 | |
| 4-8 | |
| 4-9 | |

TABLE 4-continued
| Compound No. | Structural formula |
|---|---|
| 4-10 | 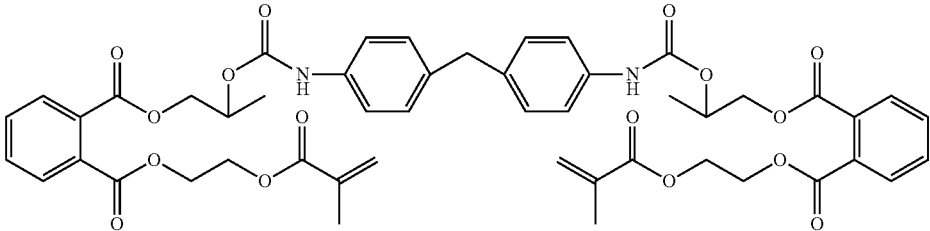 [SMILES: C=C(C)C(=O)OCCOC(=O)c1ccccc1C(=O)OCC(C)OC(=O)Nc1ccc(Cc2ccc(NC(=O)OC(C)COC(=O)c3ccccc3C(=O)OCCOC(=O)C(=C)C)cc2)cc1] |
TABLE 5
| Compound No. | Structural formula |
|---|---|
| 5-1 | 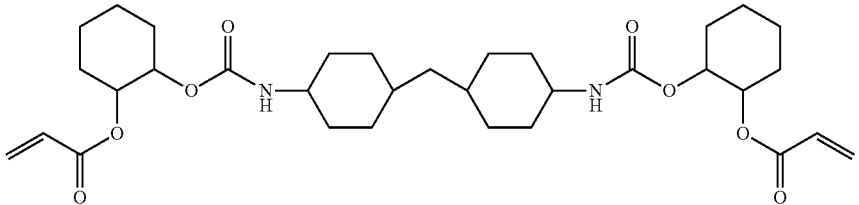 [SMILES: C=CC(=O)OC1CCCCC1OC(=O)NC1CCC(CC2CCC(NC(=O)OC3CCCCC3OC(=O)C=C)CC2)CC1] |
| 5-2 | 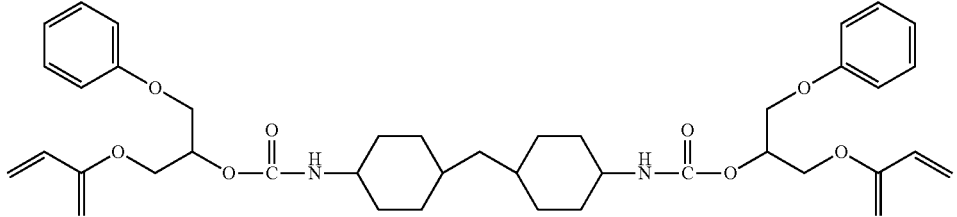 [SMILES: C=CC(=C)OCC(COc1ccccc1)OC(=O)NC1CCC(CC2CCC(NC(=O)OC(COC(=C)C=C)COc3ccccc3)CC2)CC1] |
| 5-3 | 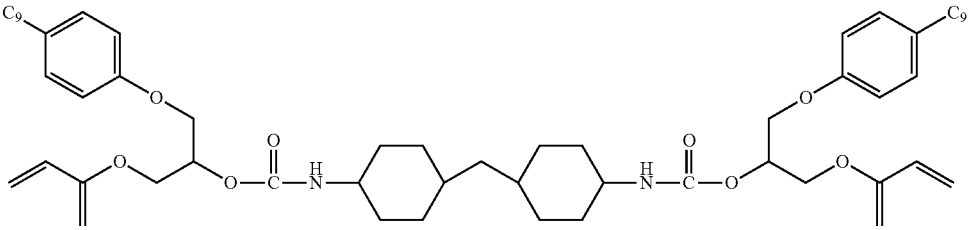 |
| 5-4 | 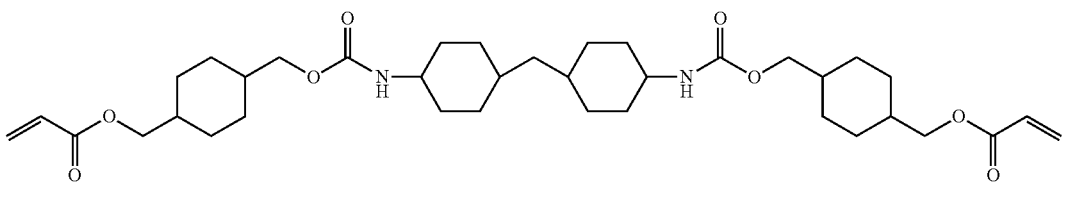 [SMILES: C=CC(=O)OCC1CCC(COC(=O)NC2CCC(CC3CCC(NC(=O)OCC4CCC(COC(=O)C=C)CC4)CC3)CC2)CC1] |
| 5-5 | 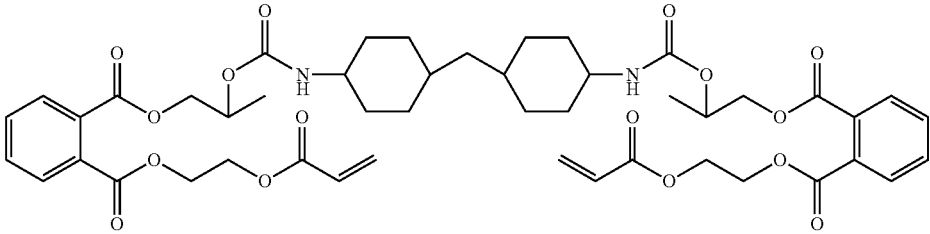 [SMILES: C=CC(=O)OCCOC(=O)c1ccccc1C(=O)OCC(C)OC(=O)NC1CCC(CC2CCC(NC(=O)OC(C)COC(=O)c3ccccc3C(=O)OCCOC(=O)C=C)CC2)CC1] |

TABLE 5-continued

| Compound No. | Structural formula |
|---|---|
| 5-6 | |
| 5-7 | |
| 5-8 | |
| 5-9 | |

TABLE 6

| Compound No. | Structural formula |
|---|---|
| 6-1 | |
| 6-2 | |

TABLE 6-continued

| Compound No. | Structural formula |
|---|---|
| 6-3 | |
| 6-4 | |
| 6-5 | |
| 6-6 | |
| 6-7 | |
| 6-8 | |

TABLE 6-continued

| Compound No. | Structural formula |
|---|---|
| 6-9 | |

TABLE 7

| Compound No. | Structural formula |
|---|---|
| 7-1 | |
| 7-2 | |
| 7-3 | |

TABLE 7-continued

| Compound No. | Structural formula |
|---|---|
| 7-4 | |
| 7-5 | |
| 7-6 | |
| 7-7 | |
| 7-8 | |

TABLE 7-continued

| Compound No. | Structural formula |
|---|---|
| 7-9 | (structure) |
| 7-10 | (structure) |

TABLE 8

| Compound No. | Structural formula |
|---|---|
| 8-1 | (structure) |
| 8-2 | (structure) |
| 8-3 | (structure) |
| 8-4 | (structure) |

TABLE 8-continued

| Compound No. | Structural formula |
|---|---|
| 8-5 | |
| 8-6 | |
| 8-7 | |
| 8-8 | |
| 8-9 | |
| 8-10 | |

TABLE 9

| Compound No. | Structural formula |
|---|---|
| 9-1 | |
| 9-2 | |
| 9-3 | |
| 9-4 | |
| 9-5 | |

| Compound No. | Structural formula |
|---|---|
| 9-6 | 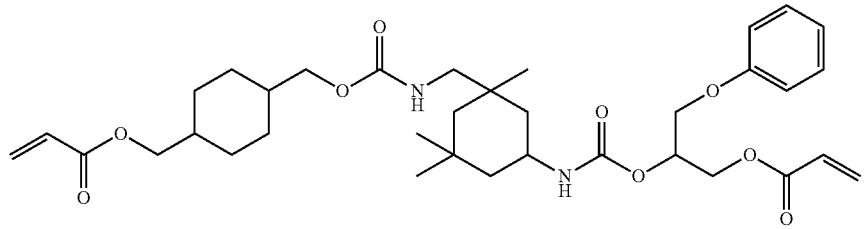 [SMILES: C=CC(=O)OCC1CCC(COC(=O)NCC2(C)CC(NC(=O)OC(COC(=O)C=C)COc3ccccc3)CC(C)(C)C2)CC1] |

It is most preferable that the urethane(meth)acrylic compound of the present invention be selected from compounds represented by Formulae (2) to (5) below. Such a urethane (meth)acrylic compound has a smaller polymerization shrinkage, excellent transparency, a favorable and appropriate viscosity at the time of preparation of the composition and operation properties, and tends to be unlikely to be colored when being formed into a cured product. Further, such a urethane(meth)acrylic compound is relatively high in refractive index and ensures that a cured product thereof exhibits transparency. The cured product is excellent in aesthetic properties in a dental use, and thus is preferred. The cured product is suited for optical material use, dental material use and the like that require transparency.

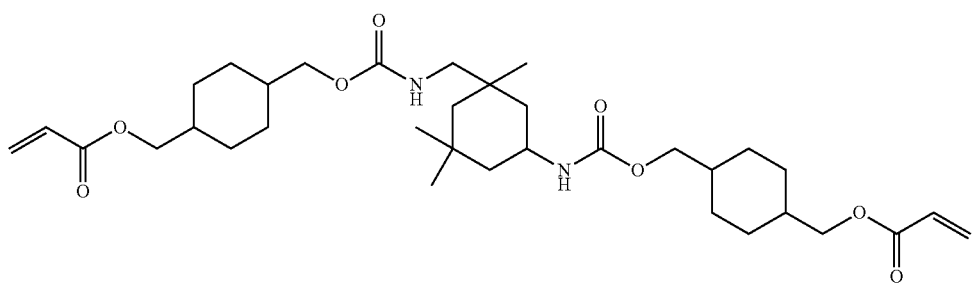

(2)

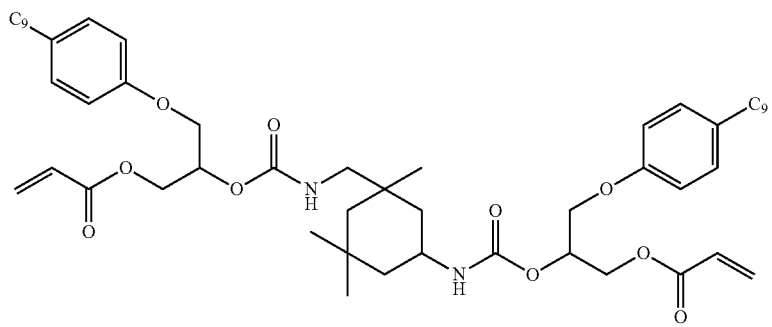

(3)

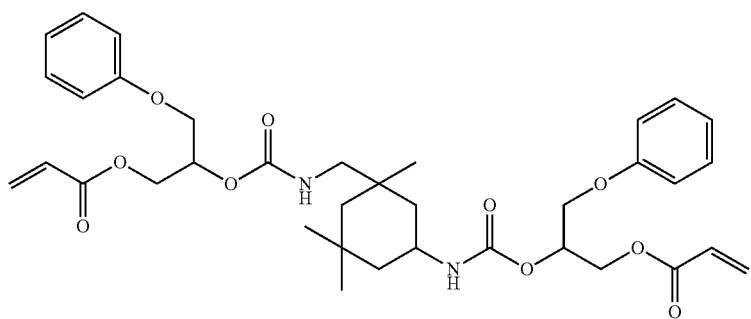

(4)

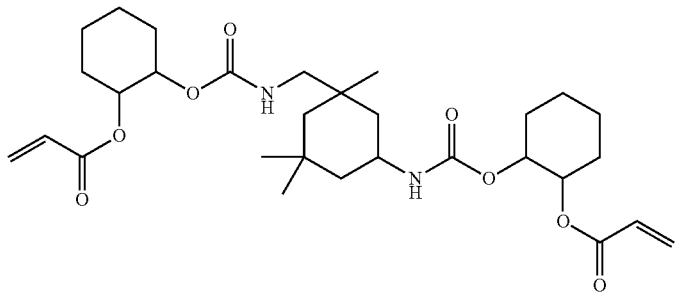 [SMILES: C=CC(=O)OC1CCCCC1OC(=O)NCC1(C)CC(NC(=O)OC2CCCCC2OC(=O)C=C)CC(C)(C)C1]

(5)

Processes for Producing Urethane(Meth)Acrylic Compounds

The urethane(meth)acrylic compound of the invention may be produced by any process without limitation. However, the compound may be generally produced by an addition reaction of a diisocyanate compound and a hydroxyl group-containing (meth)acrylic compound illustrated in Scheme 1 below.

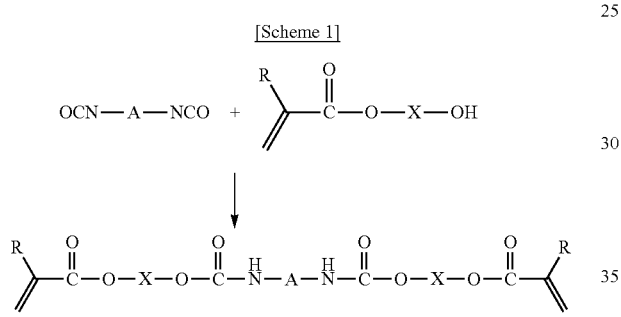

[Scheme 1]

In Scheme 1, A, R and X correspond to A, $R_1$ or $R_2$, and $X_1$ or $X_2$, respectively, in Formula (1).

In Scheme 1, hydroxyl group-containing (meth)acrylic compounds having different structures may be used in order to produce a compound of Formula (1) in which $X_1$ and $X_2$ are different from each other. However, it is generally difficult to produce a compound with differing $X_1$ and $X_2$ alone. That is, the product is a mixture of a compound of Formula (1) in which the organic groups are both $X_1$, a compound in which the organic groups are both $X_2$, and a compound in which the organic groups are $X_1$ and $X_2$. The mixture includes isomers. According to necessity, the urethane(meth)acrylic compound of the invention can be produced also by purifying such mixtures.

For example, Table 10 illustrates a diisocyanate compound and hydroxyl group-containing acrylic compounds that are used as raw materials for the production of a compound of Formula (1) in which $R_1$ and $R_2$ are hydrogen atoms, A is represented by:

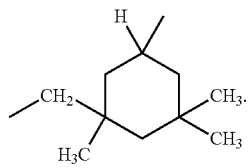

a $X_1$ is represented by:

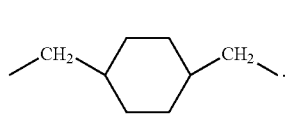

j and $X_2$ is represented by:

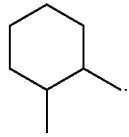

m (Some) of the compounds that are obtained as a mixture are also illustrated.

TABLE 10

| Diisocyanate compound | Hydroxyl group-containing acryl compounds | |
|---|---|---|
| ![OCN...NCO] | ![acrylate-cyclohexyl-OH] | ![cyclohexyl-diol acrylate] |

TABLE 10-continued

Product

[chemical structures]

Hydroxyl Group-Containing (Meth)Acrylic Compounds

Many kinds of hydroxyl group-containing (meth)acrylic compounds that are available from the industry may be used in the invention. Alternatively, a hydroxyl group-containing (meth)acrylic compound may be obtained by ring-opening esterification of an epoxy compound and (meth)acrylic acid.

The ring-opening esterification may be carried out with or without a solvent. Known solvents that are inert in the reaction may be used. Examples of such solvents include hydrocarbon solvents such as n-hexane, benzene, toluene and xylene;

ketone solvents such as acetone, methyl ethyl ketone and methyl isobutyl ketone;

ester solvents such as ethyl acetate and butyl acetate;

ether solvents such as diethyl ether, tetrahydrofuran and dioxane;

halogen solvents such as dichloromethane, chloroform, carbon tetrachloride, 1,2-dichloroethane and perchlene; and polar solvents such as N,N-dimethylformamide, N,N-dimethylacetamide, N,N-dimethylimidazolidinone, dimethylsulfoxide and sulfolane. These solvents may be used singly, or two or more kinds may be used in combination.

The reaction may involve a catalyst as required. Known catalysts may be used. Examples of the catalysts include organophosphine compounds such as triphenylphosphine;

tertiary amines such as triethylamine and triethanolamine;

quaternary ammonium salts such as trimethylammonium chloride and triethylbenzylammonium chloride;

organophosphonium salts such as tetrabutylphosphonium bromide and tetraphenylphosphonium bromide; imidazoles such as 2-methylimidazole; and organometallic compounds such as cobalt octenoate.

The catalyst is generally added in an amount of 0.01 to 10.0% by weight, and preferably 0.01 to 5.0% by weight with respect to 100% by weight of the total weight of the reactants. This addition amount of catalyst is preferable because the reaction takes place at a sufficiently high reaction rate.

The reaction temperature is not particularly limited. However, it is generally in the range of 0 to 200° C., and preferably 0 to 150° C.

The reaction time is variable in accordance with conditions such as reaction temperature, and is not particularly limited. However, the reaction time is usually from several minutes to several tens of hours. The reaction may be carried out while checking the reaction ratio by known analytical means (for example, liquid chromatography, thin layer chromatography or infrared spectroscopy) and may be terminated when a desired reaction ratio is obtained.

Diisocyanate Compounds

Many kinds of diisocyanate compounds are available from the industry, and such compounds may be directly used in the invention. Alternatively, a diisocyanate compound for use in the invention may be synthesized by a reaction of a corresponding diamine compound and phosgene.

Steps

The urethane(meth)acrylic compound of the present invention may be produced by a process including the following step (B), and preferably by a process including the following steps (A), (B) and (C). The obtained urethane (meth)acrylic compound often contains a trace amount of contaminants. Thus, it is preferable that the process include a step of removing such contaminants by filtration.

The steps performed in the invention include:

(A) a step of dehydrating a hydroxyl group-containing (meth)acrylic compound at 20 to 90° C.;

(B) a step of performing a urethane-forming reaction by adding dropwise a diisocyanate compound to the hydroxyl group-containing (meth)acrylic compound which has been subjected to the dehydration step, or to a hydroxyl group-containing (meth)acrylic compound which has not been dehydrated; and (C) a step of deodorizing the product at 20 to 90° C.

Step A

In the step (A), a hydroxyl group-containing (meth) acrylic compound is dehydrated in the presence of oxygen at a temperature of 20 to 90° C. In this step, a polymerization inhibitor and a urethane-forming catalyst may be mixed to the hydroxyl group-containing (meth)acrylic compound as required. Performing the step (A) is preferable because if the hydroxyl group-containing (meth))acrylic compound contains water, such water can decompose the diisocyanate compound during the urethane-forming reaction in the subsequent step (B).

In the step (A), a polymerization inhibitor is preferably added. In the invention, a known polymerization inhibitor may be used without limitation. Examples thereof include hydroquinone (HQ), hydroquinone monomethyl ether (MQ), 2,6-di-tert-butylhydroxytoluene (BHT) and phenothiazine (PTZ). BHT is preferable in that it is more unlikely for BHT to be consumed by being reacted with isocyanate groups compared to other phenolic polymerization inhibitors, as well as in that a coloration is reduced compared to amine polymerization inhibitors. The usage amount of polymerization inhibitor is preferably 0.001 to 0.5% by weight with respect to 100% by weight of the total weight of the hydroxyl group-containing (meth)acrylic compound and the diisocyanate compound. The polymerization inhibitor may be added at any time before the diisocyanate compound is added dropwise. For example, the polymerization inhibitor may be mixed to the hydroxyl group-containing (meth)acrylic compound beforehand. However, it is preferable to add the polymerization inhibitor prior to the dehydration because the loss of polymerizable groups due to thermal history is reduced.

In the step (A), a urethane-forming catalyst is preferably added. In the invention, a known urethane-forming catalyst may be used without limitation. Examples thereof include:

organotin compounds such as dibutyl tin dilaurate, dibutyl tin dioctoate and tin octanoate;

organometallic compounds of metals other than tin, such as copper naphthenate, cobalt naphthenate, zinc naphthenate, zirconium acetylacetonate, iron acetylacetonate and germanium acetylacetonate;

amine compounds such as triethylamine, 1,4-diazabicyclo [2.2.2]octane, 2,6,7-trimethyl-1-diazabicyclo[2.2.2]octane, 1,8-diazabicyclo[5.4.0]undecene, N,N-dimethylcyclohexylamine, pyridine, N-methylmorpholine, N,N,N',N'-tetramethylethylenediamine, N,N,N',N'-tetramethyl-1,3-butanediamine, N,N,N',N'-pentamethyldiethylenetriamine, N,N,N',N'-tetra(3-dimethylaminopropyl)-methanediamine, N,N'-dimethylpiperadine, 1,2-dimethylimidazole, and salts of these compounds; and trialkylphosphine compounds such as tri-n-butylphosphine, tri-n-hexylphosphine, tricyclohexylphosphine and tri-n-octylphosphine.

Of these, dibutyl tin dilaurate and tin octanoate are suitably used because they can catalyze the reaction in a small amount and have high selectivity with respect to diisocyanate compounds. When the urethane-forming catalyst is used, the catalyst is preferably added at 0.001 to 0.1% by weight with respect to 100% by weight of the total weight of the hydroxyl group-containing (meth)acrylic compound and the diisocyanate compound. If the amount is less than 0.001% by weight, catalytic effects are small and the reaction takes a long time. If the amount is in excess of 0.1% by weight, catalytic effects are so increased that a large amount of reaction heat is generated, possibly resulting in difficult temperature control. The urethane-forming catalyst may be added at any time before the diisocyanate compound is added dropwise. For example, the catalyst may be mixed to the hydroxyl group-containing (meth)acrylic compound beforehand.

Oxygen is an effective polymerization inhibitor for hydroxyl group-containing (meth)acrylic compounds and the inventive urethane(meth))acrylic compounds. Dry air or oxygen gas, preferably dry air, may be used as oxygen by being supplied in the form of bubbles from the bottom of the reaction container. The dry air used herein is preferably air that has been dried with a condensing air dryer or the like. Insufficient drying allows water to find its way into the reaction system so as to induce a reaction of water with the diisocyanate compound, possibly resulting in an increase in the viscosity of the obtained urethane(meth)acrylic compound. The supply amount of dry air is variable in accordance with the size of the reaction container, and is thus not particularly limited. In the case of a 1-L volume reaction container as an example, the supply amount is 1 to 500 ml/min, and preferably 1 to 300 ml/min. At less than 1 ml/min, oxygen cannot be supplied in a sufficient amount and can fail to serve effectively as a polymerization inhibitor. Adding oxygen in excess of 500 ml/min increases the volatilization of the diisocyanate compound during the reaction, possibly resulting in a decrease in properties of a cured product of the urethane(meth)acrylic compound.

The dehydration is performed at a temperature which does not induce thermal polymerization of polymerizable groups. The temperature is generally in the range of 20 to 90° C., and preferably 30 to 80° C. If the temperature is less than 20° C., the dehydration results are insufficient so as to induce a reaction of water with the diisocyanate compound, possibly resulting in an increase in the viscosity of the urethane (meth)acrylic compound. If the temperature is in excess of 90° C., a polymerization reaction can be induced and the urethane(meth)acrylic compound may be colored.

The pressure during the dehydration is not particularly limited. However, the pressure is usually in the range of 0.133 to 13.3 kPa (1 to 100 mmHg), and preferably 0.133 to 6.67 kPa (1 to 50 mmHg). Any pressure that is lower than 0.133 kPa is not preferable because energy consumption is raised and environmental loads are increased. If the pressure is higher than 13.3 kPa, the dehydration results are insufficient so as to induce a reaction of water with the diisocyanate compound, possibly resulting in an increase in the viscosity of the urethane(meth)acrylic compound.

The dehydration time is not particularly limited. The water content in the system may be measured at appropriate times, and the dehydration may be terminated when the water content is decreased to not more than 0.15% by weight, and preferably not more than 0.10% by weight with respect to 100% by weight of the total weight of the hydroxyl group-containing (meth)acrylic compound, the polymerization inhibitor and the urethane-forming catalyst. The water content may be measured with a water content measuring apparatus in accordance with JIS K 0068. For example, a volumetric drop method may be performed using a Karl Fischer's reagent and an automatic titrator. In detail, after dehydration is carried out under vacuum, the pressure may be returned to atmospheric pressure and the mixture of the hydroxyl group-containing (meth)acrylic compound, the polymerization inhibitor and the urethane-forming catalyst may be collected and analyzed to determine the water content.

Step (B)

In the step (B), a urethane-forming reaction is performed by adding dropwise a diisocyanate compound to the hydroxyl group-containing (meth)acrylic compound which has been subjected to the dehydration step, or to a hydroxyl group-containing (meth)acrylic compound which has not been dehydrated.

In the invention, the hydroxyl group-containing (meth) acrylic compound and the diisocyanate compound are used at such a ratio that the equivalent weight of the hydroxyl groups in the hydroxyl group-containing (meth)acrylic compound is preferably 1.0 to 1.3, and more preferably 1.0 to 1.1 with respect to 1.0 equivalent weight of the isocyanate groups in the diisocyanate compound. If the equivalent weight of the hydroxyl groups in the hydroxyl group-containing (meth)acrylic compound is less than 1.0, some of the isocyanate groups remain unreacted so as to possibly cause precipitation of solids or an increase in viscosity after the production. If the equivalent weight is in excess of 1.3, the amount of unreacted hydroxyl group-containing (meth) acrylic compound is increased so as to possibly cause deteriorations in properties after curing.

In the drop method, an appropriate diisocyanate compound is placed into a drop container connected to the reaction container and is added to the reaction container in a constant amount in a certain time while controlling the flow rate. In contrast, there is a batch addition method in which a predetermined diisocyanate compound is added at one time in a short time. According to such a batch addition method, the temperature can be greatly increased and the temperature control can become difficult depending on the structures and the molecular weights of the hydroxyl group-containing (meth)acrylic compound and the diisocyanate compound, the structure of the reaction container, the shape of the stirring blade, and the stirring speed. As a result, the crosslinking reaction of the diisocyanate compound is accelerated so as to cause an increase in the viscosity of the obtained urethane(meth)acrylic compound. In some cases, such a drastic increase in temperature induces polymerization of polymerizable groups resulting in gelation.

It is also possible to drop the hydroxyl group-containing (meth)acrylic compound to the diisocyanate compound. Because a larger amount of the hydroxyl group-containing (meth)acrylic compound than the diisocyanate compound is necessary, such a manner of drop takes a longer time than required when the diisocyanate compound is dropped. Further, such a manner of drop causes the urethane(meth)acrylic compound to have an undesired thermal history and can induce polymerization of polymerizable groups, possibly resulting in a decrease in production efficiency.

The temperature in the reaction system is variable depending on the configuration, for example the size and the structure, of the reaction container and is thus not particularly limited. However, the temperature is usually 20 to 120° C., and preferably 30 to 100° C. If the temperature exceeds 120° C., a polymerization reaction can take place and the obtained urethane(meth)acrylic compound may not exhibit desired functions. The reaction at a temperature of less than 20° C. requires a longer reaction time, and the production efficiency may be deteriorated.

The drop may be initiated at any temperature without limitation. However, the drop initiation temperature is usually 20 to 90° C., and preferably 30 to 80° C. If the temperature is less than 20° C., the reaction requires a longer time and the production efficiency may be deteriorated. Temperatures in excess of 90° C. increase the probability that a polymerization reaction will take place or the reaction (drop) temperature will be so increased that the reaction cannot be controlled.

The drop rate is not limited as long as the above temperature of the reaction system is maintained.

The drop time is not limited as long as the above temperature is satisfied. However, the drop time is usually 0.1 to 30 hours, and preferably 0.1 to 5 hours. If the drop time is less than 0.1 hour, the temperature can be drastically increased and become out of control. Drop for more than 5 hours tends to deteriorate the production efficiency of the urethane(meth)acrylic compound.

In the case where the reaction does not complete in the above drop time in the step (B), the reaction may be continuously carried out after the completion of the drop as required. This reaction time is variable depending on the reaction temperature, the size and the structure of the reaction container, the drop time and other factors, and is not particularly limited. However, the total of the drop time and this reaction time is usually 1 to 30 hours, and preferably 1 to 20 hours. There is a probability that the reaction will not complete in less than 1 hour. Any total time that is in excess of 30 hours causes the urethane(meth)acrylic compound to have an undesired thermal history and can induce polymerization of polymerizable groups, possibly resulting in a decrease in production efficiency and an increase in product cost.

The reaction temperature after the completion of the drop is not particularly limited as long as thermal polymerization of polymerizable groups is not induced. However, the reaction temperature is usually in the range of 20 to 120° C., and preferably 30 to 100° C. If the temperature is less than 20° C., the reaction may take a long time so as to possibly deteriorate the production efficiency. If the temperature is in excess of 120° C., a polymerization reaction can be induced and the urethane(meth)acrylic compound may be colored.

The end point of the reaction may be confirmed by a measurement method in accordance with JIS K 1556 5.5, for example by measuring the content of the diisocyanate compound in the reaction product or by analyzing the reaction system by HPLC (high performance liquid chromatography). In detail, a portion of the reaction product is withdrawn from the reaction container and is reacted with di-n-butylamine, and unreacted amine is titrated with hydrochloric acid so as to determine the content of the diisocyanate compound in the reaction product. The end point is reached when the content of the diisocyanate compound determined by the above method becomes not more than 0.5% by weight, and preferably not more than 0.1% by weight with respect to 100% by weight of the weight of the reaction product.

Step (C)

After the completion of the step (B), the deodorizing step (C) may be preferably performed as required. Deodorization increases the quality of the urethane(meth)acrylic compound.

The temperature in the step (C) is preferably a temperature which does not cause thermal polymerization of polymerizable groups. The temperature is usually in the range of 20 to 120° C., and preferably 30 to 100° C. If the temperature is less than 20° C., the deodorization results are insufficient and the urethane(meth)acrylic compound may exhibit a strong odor and poor storage stability. If the temperature is in excess of 120° C., a polymerization reaction can be induced and the urethane(meth)acrylic compound may be colored.

The pressure in the step (C) is not particularly limited. However, the pressure is usually in the range of 0.133 to 13.3 kPa (1 to 100 mmHg), and preferably 0.133 to 6.67 kPa (1 to 50 mmHg). Any pressure that is lower than 0.133 kPa is not preferable because industrial production at such a pressure is difficult and costs will be increased. If the pressure is higher than 13.3 kPa, the deodorization results are insufficient and the urethane(meth)acrylic compound may exhibit a strong odor and poor storage stability.

The deodorization time is variable depending on the size and the structure of the reaction container, and is not particularly limited. However, the deodorization time is usually 1 to 10 hours, and preferably 1 to 5 hours. Sufficient deodorization results cannot be obtained in less than 1 hour, and the obtained urethane(meth)acrylic compound may exhibit a strong odor and poor storage stability. Any deodorization time that is in excess of 10 hours causes the urethane (meth)acrylic compound to have an undesired thermal history and can induce polymerization of polymerizable groups and cause a decrease in production efficiency and an increase in product cost.

Novel Compositions (Urethane(Meth)Acrylic Compound Compositions)

The urethane(meth)acrylic compound composition of the present invention includes one kind or two or more kinds of the urethane(meth)acrylic compound of the present invention.

Although not particularly limited, examples of preferred use of the urethane(meth)acrylic compound composition include optical materials, adhesive materials and coating materials. Of these, a preferred use is a dental material, with examples thereof including dental restorative materials, dental composite resins (composite resins for core build-up, polymer-based crown and bridge materials, dental restorative composite resins), denture base resins, denture base liners, dental impression materials, dental luting materials (dental resin cements, resin modified glass-ionomer cements), dental adhesives, dental adhesives for orthodontic treatment, pit and fissure sealants, CAD/CAM resin blocks, temporary crowns and artificial tooth materials.

In particular, the urethane(meth)acrylic compound composition containing the inventive urethane(meth)acrylic compound as well as a polymerization initiator (B) and a filler (C) described later is one of the preferred embodiments of the invention from the viewpoint of improving the strength and elastic modulus of the resultant cured product.

Further, the urethane(meth)acrylic compound composition containing the inventive urethane(meth)acrylic compound as well as the photopolymerization initiator (B) and the filler (C) has photocuring properties, and thus is preferred from the viewpoint of shortening effect time.

The urethane(meth)acrylic compound composition may contain a known polymerizable monomer (D) other than the inventive urethane(meth)acrylic compounds as required. Such a combined use of the polymerizable monomer (D) is preferred because of allowing for controlling of the viscosity or the refractive index of the composition in accordance with a purpose.

When the inventive compound is used in the dental restorative material and the like, the inventive composition is usually in the form of a paste including the filler (C). Such a paste is usually obtained by mixing at least the inventive urethane(meth)acrylic compound, the polymerizable monomer (D), the photopolymerization initiator (B) and the filler (C). If the viscosity of a composition (I) containing the urethane(meth)acrylic compound and the polymerizable monomer (D) is too high, it is difficult to mix the composition (I) with the filler (C), leading to the difficulty in incorporating an increased amount of the filler (C). If the viscosity is too low, in mixing the composition (I) with the filler (C), it is difficult for the inventive composition to be in the form of a paste. The composition (I) usually has a viscosity of 50 to 50000 (mPa·s, 30° C.), preferably 100 to 20000 (mPa·s, 30° C.), more preferably 100 to 10000 (mPa·s, 30° C.). The inventive urethane(meth)acrylic compound, for example, provides a favorable viscosity at the time of preparation of the composition while providing extremely low polymerization shrinkage at the time of polymerization curing of the composition; the inventive urethane(meth)acrylic compound simultaneously achieves these two conflicting effects.

Polymerization Initiators or Photopolymerization Initiators (B)

The (photo)polymerization initiator may be a known (photo)polymerization initiator, and is generally selected in consideration of the polymerizability of the polymerizable monomer(s) and the polymerization conditions.

When the polymerization is carried out at normal temperature, a suitable polymerization initiator is a redox system containing an oxidant and a reductant in combination. A redox polymerization initiator has a form in which an oxidant and a reductant are separately packed. It is therefore necessary to mix them immediately before use.

The oxidants are not particularly limited. Examples thereof include organic peroxides such as diacyl peroxides, peroxyesters, dialkyl peroxides, peroxyketals, ketone peroxides and hydroperoxides. Specific examples include diacyl peroxides such as benzoyl peroxide, 2,4-dichlorobenzoyl peroxide and m-toluoyl peroxide;

peroxyesters such as t-butyl peroxybenzoate, bis-t-butyl peroxyisophthalate, 2,5-dimethyl-2,5-bis(benzoylperoxy)hexane, t-butyl peroxy-2-ethylhexanoate and t-butyl peroxyisopropylcarbonate;

dialkyl peroxides such as dicumyl peroxide, di-t-butyl peroxide and lauroyl peroxide;

peroxyketals such as 1,1-bis(t-butylperoxy)-3,3,5-trimethylcyclohexane;

ketone peroxides such as methyl ethyl ketone peroxide; and hydroperoxides such as t-butyl hydroperoxide.

The reductants are not particularly limited. Tertiary amines are generally used, with examples including N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2- hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-1-propylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine and tris(methacryloyloxyethyl)amine.

Examples other than the above organic peroxide/amine systems include such redox polymerization initiators as cumene hydroperoxide/thiourea systems, ascorbic acid/$Cu^{2+}$ salt systems and organic peroxide/amine/sulfinic acid (or sulfinate salt) systems.

Further, tributylborane and organic sulfinic acids may be also suitably used as polymerization initiators.

When photopolymerization is carried out by the irradiation with visible light, preferred initiators are redox initiators such as α-diketone/tertiary amine systems, α-diketone/aldehyde systems and α-diketone/mercaptan systems.

The photopolymerization initiators are not particularly limited. Examples thereof include α-diketone/reductant systems, ketal/reductant systems and thioxanthone/reductant systems. Examples of the α-diketones include camphorquinone, benzyl and 2,3-pentanedione. Examples of the ketals include benzyl dimethyl ketal and benzyl diethyl ketal. Examples of the thioxanthones include 2-chlorothioxanthone and 2,4-diethylthioxanthone. Examples of the reductants include Michler's ketone;

tertiary amines such as 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine and dimethylaminophenanthol;

aldehydes such as citronellal, lauryl aldehyde, phthaldialdehyde, dimethylaminobenzaldehyde and terephthalaldehyde; and compounds having a thiol group such as 2-mercaptobenzoxazol, decanethiol, 3-mercaptopropyltrimethoxysilane, 4-mercaptoacetophenone, thiosalicylic acid and thiobenzoic acid.

Further, organic peroxides may be used in combination with these redox initiators. That is, α-diketone/organic peroxide/reductant systems may be also suitably used.

When photopolymerization is performed by the irradiation with UV ray, preferred photopolymerization initiators are benzoin alkyl ethers and benzyl dimethyl ketals. (Bis)acylphosphine oxides are also suitable as photopolymerization initiators.

Of the (bis)acylphosphine oxides, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide and benzoyl-di(2,6-dimethylphenyl)phosphonate.

Examples of the bis-acylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phonylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide and (2,5,6-trimethylbenzoyl)-2,4,4-trimethylpentylphosphine oxide.

These (bis)acylphosphine oxide photopolymerization initiators may be used singly or in combination with various reductants such as amines, aldehydes, mercaptans and sulfinate salts.

Further, these photopolymerization initiators may be suitably used in combination with the aforementioned visible light photopolymerization initiators.

The aforementioned polymerization initiators and photopolymerization initiators may be used singly, or two or more kinds may be used in combination appropriately. The amount of initiator is usually in the range of 0.01 to 20% by weight, and preferably 0.1 to 5% by weight with respect to 100% by weight of the urethane(meth)acrylic compound composition.

Fillers (C)

The fillers may be known fillers. Fillers are largely categorized into organic fillers and inorganic fillers.

Examples of the organic fillers include polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer and styrene-butadiene copolymer.

Examples of the inorganic fillers include various kinds of glass (the main component is silicon dioxide, and oxides of, for example, heavy metals, boron and aluminum are contained as required), ceramics, diatomaceous earths, kaolins, clay minerals (such as montmorillonite), activated white earths, synthetic zeolites, micas, calcium fluoride, ytterbium fluoride, calcium phosphate, barium sulfate, zirconium dioxide, titanium dioxide and hydroxyapatite.

A polymerizable monomer may be added beforehand to the inorganic filler to give a paste, and the paste may be cured by polymerization and thereafter crushed. Such an organic inorganic composite filler may be used in the invention.

The fillers may be used singly, or two or more kinds may be used in combination appropriately.

The amount of filler may be determined appropriately in accordance with operation properties (viscosity) of the paste and mechanical strength. The amount is usually 10 to 2000 parts by weight, preferably 50 to 1000 parts by weight, and more preferably 100 to 600 parts by weight with respect to 100 parts by weight of all the components contained in the urethane(meth)acrylic compound composition except the filler.

These fillers may have been surface treated with agents such as silane coupling agents in accordance with a purpose. Examples of such surface treating agents include known silane coupling agents, for example organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The surface treating agent is usually used at a concentration of 0.1 to 20% by weight, and preferably 1 to 5% by weight with respect to 100% by weight of the filler.

Polymerizable Monomers (D)

The polymerizable monomers are not particularly limited as long as they are known monomers other than the inventive urethane(meth)acrylic compounds. Examples thereof include esters of acids such as α-cyanoacrylic acid, (meth)acrylic acid, α-halogenated acrylic acid, crotonic acid, cinnamic acid, sorbic acid, maleic acid and itaconic acid, (meth)acrylamides, (meth)acrylamide derivatives, vinyl esters, vinyl ethers, mono-N-vinyl derivatives and styrene derivatives. Of these, (meth)acrylates are favorably used. Examples of these polymerizable monomers are described below. In the invention, monomers having one olefinic double bond are referred to as monofunctional monomers. Similarly, monomers having two olefinic double bonds or three olefinic double bonds are referred to as bifunctional monomers or trifunctional monomers, respectively.

The polymerizable monomers may be used singly, or two or more kinds may be used in combination.

(i) Examples of the monofunctional monomers include methyl(meth)acrylate, iso-butyl(meth)acrylate, benzyl (meth)acrylate, lauryl(meth)acrylate, 2-(N,N-dimethylamino)ethyl(meth)acrylate, 2,3-dibromopropyl(meth)acrylate, 3-methacryloyloxypropyl trimethoxysilane, 2-hydroxyethyl(meth)acrylate, 6-hydroxyhexyl(meth)acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, N,N-(dihydroxyethyl)(meth)acrylamide, (meth)acryloyloxydodecylpyridinium bromide, (meth)acryloyloxydodecylpyridinium chloride and (meth)acryloyloxyhexadecylpyridinium chloride.

(ii) Examples of the bifunctional monomers include ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl methacrylate (2,2-bis[4-(3-methacryloyloxy-2-hydroxypropoxy)phenyl]propane; generally referred to as Bis-GMA), 2,2-bis[4-(meth)acryloyloxyethoxyphenyl]propane, 2,2-bis[4-(meth)acryloyloxypolyethoxyphenyl]propane, 2,2-bis[4-(3-acryloyloxy-2-hydroxypropoxy)phenyl]propane, 1,2-bis[3-(meth)acryloyloxy-2-hydroxypropoxy]ethane, pentaerythritol di(meth)acrylate, 2,2,4-trimethylhexamethylene bis(2-carbamoyloxyethyl)dimethacrylate (generally referred to as UDMA) and a compound represented by Formula (6) described below.

produced by performing an addition reaction of a diol compound and an ethylene oxide and allowing the reaction product to react with (meth)acrylic acid.

[Scheme 2]

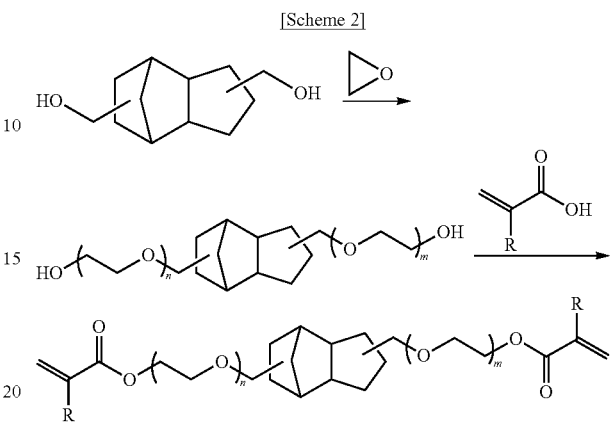

(iii) Examples of the trifunctional and polyfunctional monomers include trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene)bis[2-(aminocarboxy)propane-1,3-diol]tetramethacrylate and 1,7-diacryloyloxy-2,2,6,6-tetraacryloyloxymethyl-4-oxyheptane.

In the invention, because of relatively low shrinkage and viscosity, the polymerizable monomer (D) is preferably the compound represented by Formula (6). More preferred is a compound represented by Formula (6) wherein R is a hydrogen atom, m and n each indicate an integer from 0 to 6, and m+n=2 to 6.

As a monomer to be copolymerized, it is possible to use various kinds of adhesive monomers, in particular a monomer having an acidic group in the molecule. The monomer having an acidic group is a compound which has an acidic group and a polymerizable group in the molecule. Examples of the acidic groups include phosphoric acid residue, pyrophosphoric acid residue, thiophosphoric acid residue, carboxylic acid residue and sulfonic acid residue. Examples of the polymerizable groups include acryloyl group, methacryloyl group, vinyl group and styrene group.

Examples of polymerizable monomers having a phosphoric acid residue include 2-(meth)acryloyloxyethyldihydrogen phosphate, 9-(meth)acryloyloxynonyldihydrogen

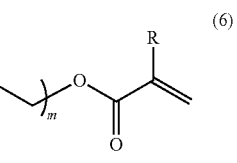

(6)

In Formula (6), R each independently indicate a hydrogen atom or a methyl group, m and n each indicate an integer of 0 to 10, and m+n=0 to 10.

With regard to the compound represented by Formula (6), JP-A-56-26809 may be referred to, and a production method thereof is not particularly limited. For example, unless m+n=0, the compound represented by Formula (6) may be phosphate, 10-(meth)acryloyloxydecyldihydrogen phosphate, 11-(meth)acryloyloxyundecyldihydrogen phosphate, 20-(meth)acryloyloxyeicosyldihydrogen phosphate, 1,3-di(meth)acryloyloxypropyl-2-dihydrogen phosphate, 2-(meth)acryloyloxyethylphenylphosphoric acid, 2-(meth)acryloyloxyethyl 2'-bromoethylphosphoric acid, (meth)acryloyloxyethylphenyl phosphonate and acid chlorides of these compounds.

Examples of polymerizable monomers having a pyrophosphoric acid residue include di(2-(meth)acryloyloxyethyl)pyrophosphate and acid chloride thereof.

Examples of polymerizable monomers having a thiophosphoric acid residue include 2-(meth)acryloyloxyethyldihydrogen dithiophosphate, 10-(meth)acryloyloxydecyldihydrogen thiophosphate and acid chlorides of these compounds.

Examples of polymerizable monomers having a carboxylic acid residue include 4-(meth)acryloyloxyethoxycarbonylphthalic acid, 5-(meth)acryloylaminopentylcarboxylic acid, 11-(meth)acryloyloxy-1,1-undecanedicarboxylic acid, and acid chlorides and acid anhydrides of these compounds.

Examples of polymerizable monomers having a sulfonic acid residue include 2-(meth)acrylamido-2-methylpropanesulfonic acid, styrenesulfonic acid and 2-sulfoethyl(meth)acrylate.

These polymerizable monomers having an acidic group may be used singly, or two or more kinds may be used in combination.

The amount of these polymerizable monomers is not particularly limited. However, they are usually used in an amount of not more than 100 parts by weight with respect to 100 parts by weight of the total amount of the urethane (meth)acrylic compound of the invention.

Others

The urethane(meth)acrylic compound composition of the invention may contain various kinds of additives as required as long as achieving the object of the invention. Examples of such additives include polymerization inhibitors, ultraviolet absorbents, fluorescent agents, pigments, heat stabilizers, anti-slip agents, crystallization auxiliaries, nucleating agents, pigments, dyes, plasticizers, anti-aging agents, antioxidants, impact resistance improvers, crosslinking agents, co-crosslinking agents, crosslinking auxiliaries, tackifiers, softeners, processing aids, blowing agents and curing agents.

Examples of the polymerization inhibitors include 2,6-dibutylhydroxytoluene, hydroquinone, dibutylhydroquinone, dibutylhydroquinone monomethyl ether, hydroquinone monomethyl ether and 2,6-di-t-butylphenol. These compounds may be used singly, or two or more kinds may be used in combination.

Examples of the curing agents include polythiol compounds and polyamino compounds. These compounds may be used singly, or two or more kinds may be used in combination.

Cured Products

The cured product of the present invention is obtained by curing the urethane(meth)acrylic compound or the urethane (meth)acrylic compound composition. The cured product is excellent in terms of mechanical strength, abrasion resistance, transparency, operation properties and safety, and has a small polymerization shrinkage in particular at the time of polymerization curing. Accordingly, the cured product is suitably used in optical materials, adhesive materials, coating materials and dental treatment. Furthermore, the cured product is excellent in aesthetic properties for dental treatment, and is suitably used in a dental field.

The curing methods are not particularly limited. Exemplary methods include self curing, thermal curing, and light curing by the irradiation with visible light or UV ray.

EXAMPLES

The present invention will be described in greater detail based on examples without limiting the scope of the invention.

Production Example 1

A 300 ml-volume, four-necked flask equipped with a stirring blade, a thermometer and a reflux condenser was charged with 111.1 g (0.5 mol) of 3-phenoxy-2-hydroxy acrylate and 0.11 g of dibutyl tin dilaurate (1000 ppm with respect to the weight of the hydroxyl group-containing (meth)acrylic compound). The temperature was raised to 60° C. Subsequently, 65.6 g (0.25 mol) of bis-isocyanatocyclohexyl methane (hydrogenated MDI) was added dropwise over a period of 0.5 hour, resulting in an increase in reaction temperature to 80° C. After the completion of the dropwise addition, the reaction was carried out for 10 hours while controlling the reaction temperature in the range of 80 to 90° C. The percent by weight of the hydrogenated MDI in the reaction product was determined to be 0.00% by weight.

The product was discharged from the reactor. Thus, 170 g of a product which contained a urethane(meth)acrylic compound represented by the following formula was obtained.

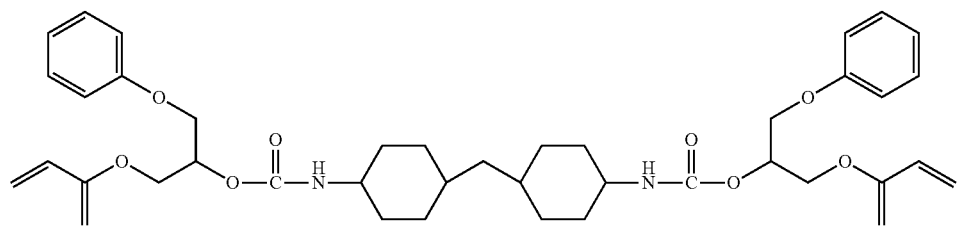 [SMILES: C=CC(=C)OCC(COc1ccccc1)OC(=O)NC1CCC(CC2CCC(NC(=O)OC(COC(=C)C=C)COc3ccccc3)CC2)CC1]

Production Examples 2 to 14

Products containing various urethane(meth)acrylic compounds were obtained by the same synthetic procedures as those in Production Example 1, except that the 3-phenoxy-2-hydroxy acrylate and the hydrogenated MDI described in Production Example 1 were replaced by a hydroxyl group-containing (meth)acrylic compound and a diisocyanate illustrated in Table 11.

TABLE 11

| Prod. Ex. | OH-containing (meth) acryl compound | Diisocyanate |
|---|---|---|
| 2 | Phenyl-O-CH2-CH(OH)-CH2-O-C(=O)-C(CH3)=CH2 | 2,4-tolylene diisocyanate (OCN, NCO on methylbenzene) |
| 3 | Phenyl-O-CH2-CH(OH)-CH2-O-C(=O)-CH=CH2 | isophorone diisocyanate |
| 4 | Phenyl-O-CH2-CH(OH)-CH2-O-C(=O)-CH=CH2 | norbornane dimethylene diisocyanate |
| 5 | Phenyl-O-CH2-CH(OH)-CH2-O-C(=O)-C(CH3)=CH2 | norbornane dimethylene diisocyanate |
| 6 | CH2=CH-C(=O)-O-CH2-(cyclohexyl)-CH2-OH | norbornane dimethylene diisocyanate |
| 7 | CH2=CH-C(=O)-O-CH2-(cyclohexyl)-CH2-OH | 2,4-tolylene diisocyanate |
| 8 | Phenyl-O-CH2-CH(OH)-CH2-O-C(=O)-CH=CH2 | 4,4'-methylenediphenyl diisocyanate |
| 9 | phthalate di(2-hydroxyethyl/2-methacryloyloxyethyl) ester | 4,4'-methylenediphenyl diisocyanate |
| 10 | phthalate di(2-hydroxyethyl/2-methacryloyloxyethyl) ester | 2,4-tolylene diisocyanate |

TABLE 11-continued
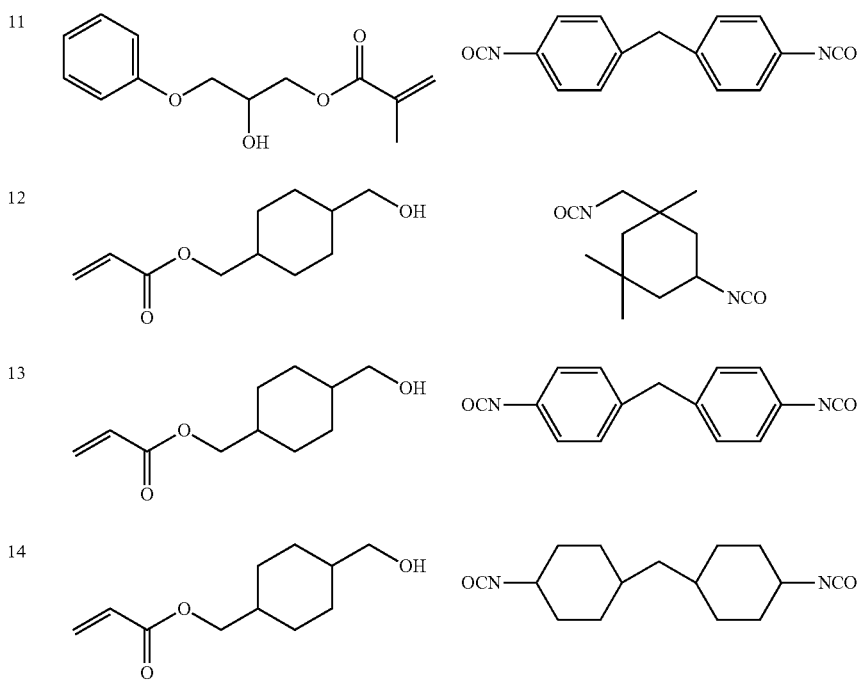
| Prod. Ex. | Structural formula |
|---|---|
| 2 | |
| 3 | |
| 4 | |
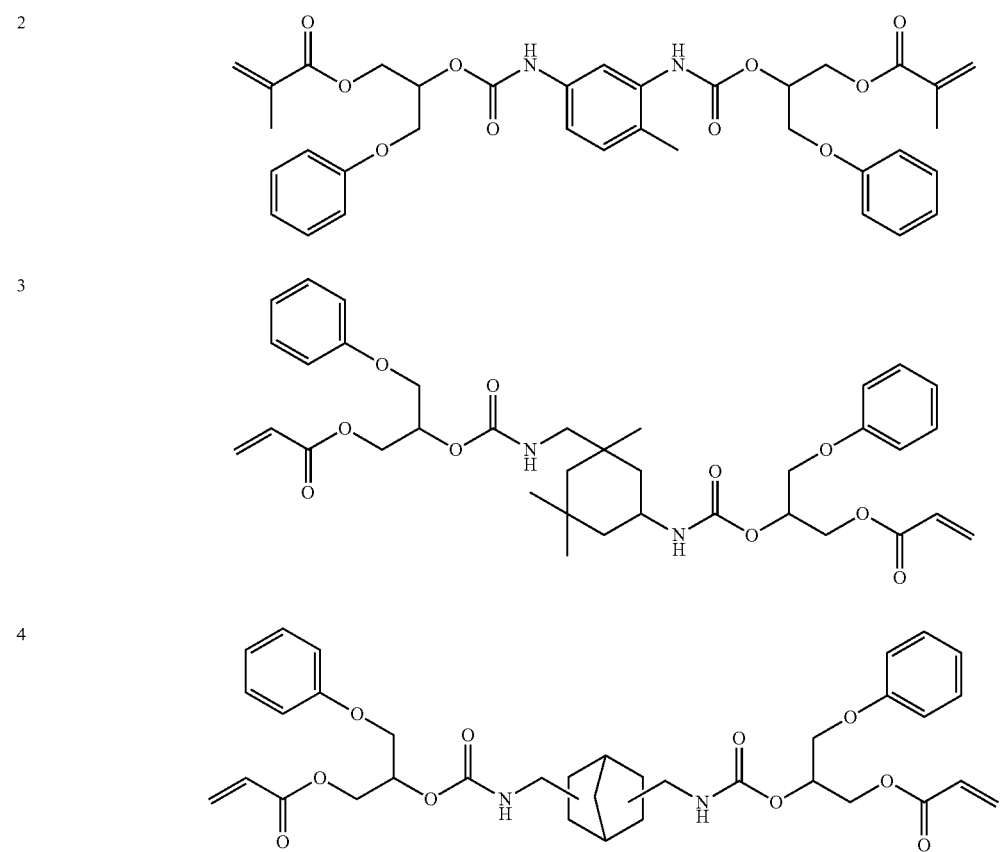

TABLE 11-continued
5
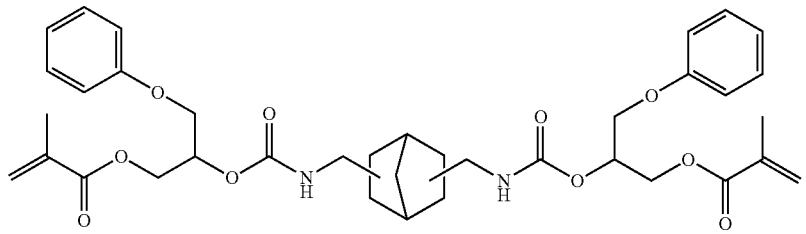
6
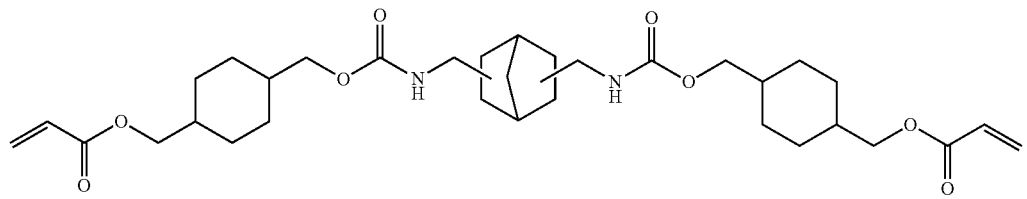
7
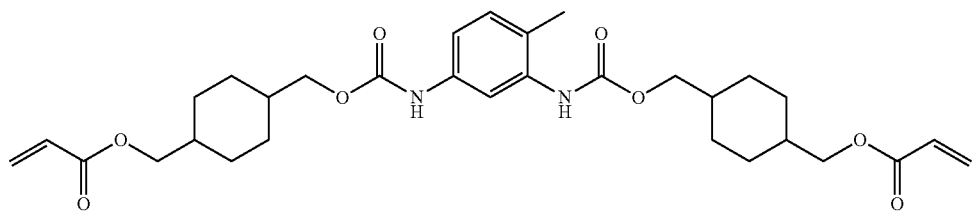 [SMILES: C=CC(=O)OCC1CCC(COC(=O)Nc2ccc(C)c(NC(=O)OCC3CCC(COC(=O)C=C)CC3)c2)CC1]
8
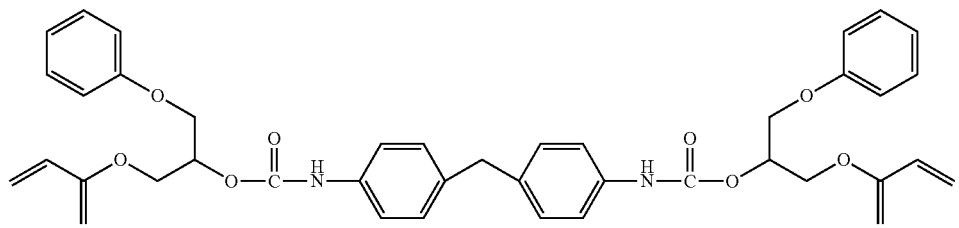 [SMILES: C=CC(=C)OCC(COc1ccccc1)OC(=O)Nc1ccc(Cc2ccc(NC(=O)OC(COC(=C)C=C)COc3ccccc3)cc2)cc1]
9
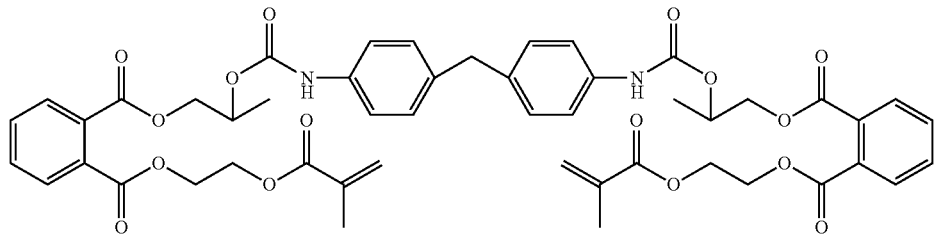 [SMILES: C=C(C)C(=O)OCCOC(=O)c1ccccc1C(=O)OCC(C)OC(=O)Nc1ccc(Cc2ccc(NC(=O)OC(C)COC(=O)c3ccccc3C(=O)OCCOC(=O)C(=C)C)cc2)cc1]
10
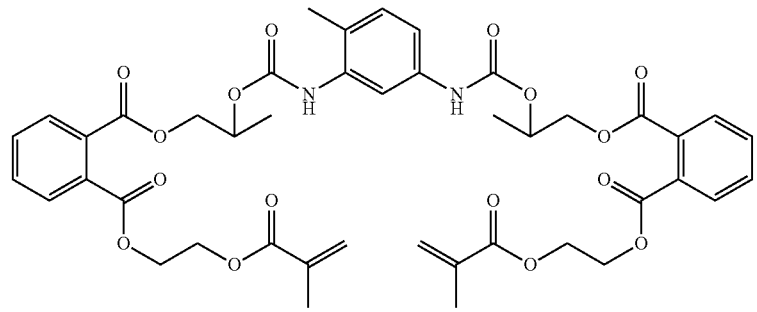 [SMILES: C=C(C)C(=O)OCCOC(=O)c1ccccc1C(=O)OCC(C)OC(=O)Nc1ccc(C)c(NC(=O)OC(C)COC(=O)c2ccccc2C(=O)OCCOC(=O)C(=C)C)c1]

TABLE 11-continued

11
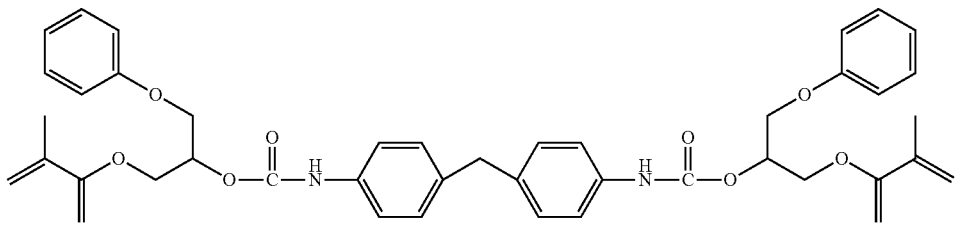 [SMILES: C=C(C)C(=C)OCC(COc1ccccc1)OC(=O)Nc1ccc(Cc2ccc(NC(=O)OC(COC(=C)C(=C)C)COc3ccccc3)cc2)cc1]

12
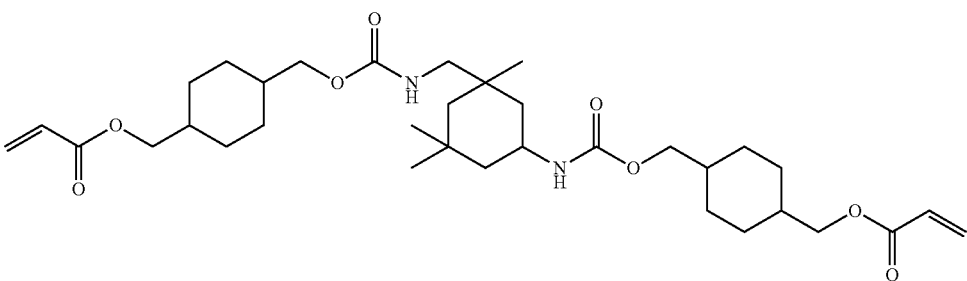 [SMILES: C=CC(=O)OCC1CCC(COC(=O)NCC2(C)CC(NC(=O)OCC3CCC(COC(=O)C=C)CC3)CC(C)(C)C2)CC1]

13
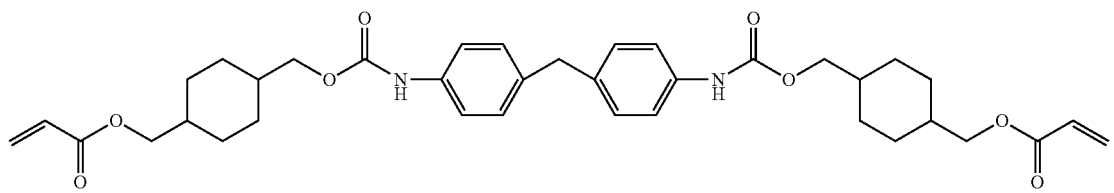 [SMILES: C=CC(=O)OCC1CCC(COC(=O)Nc2ccc(Cc3ccc(NC(=O)OCC4CCC(COC(=O)C=C)CC4)cc3)cc2)CC1]

14
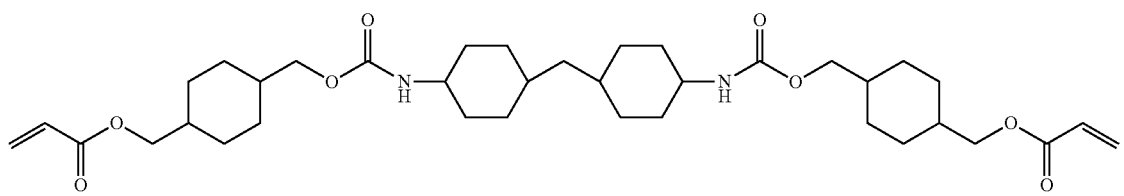 [SMILES: C=CC(=O)OCC1CCC(COC(=O)NC2CCC(CC3CCC(NC(=O)OCC4CCC(COC(=O)C=C)CC4)CC3)CC2)CC1]

Production Example 15

A 300 ml-volume, four-necked flask equipped with a stirring blade, a thermometer and a reflux condenser was charged with 14.4 g (0.2 mol) of acrylic acid and 0.5 g (1.7 mmol) of tetrabutylammonium bromide serving as a catalyst. The temperature was then raised to 60° C. Subsequently, 55.3 g (0.2 mol) of 4-nonylphenyl glycidyl ether was added dropwise over a period of 0.7 hour, resulting in an increase in reaction temperature to 65° C. After the completion of the dropwise addition, the reaction was carried out for 12 hours while controlling the reaction temperature in the range of 90 to 100° C. After the completion of the reaction, the reaction liquid was cooled to room temperature, and 200 ml of toluene was added thereto. The resultant toluene solution was poured into a 500 ml-volume separatory funnel and was washed with distilled water until the pH of the aqueous layer became neutral. After the washing with water, the toluene phase was distilled using an evaporator in order to remove toluene. Thus, 60.6 g of 2-hydroxy-4-(4-nonylphenoxy)propyl acrylate was obtained (yield: 87%).

A 300 ml-volume, four-necked flask equipped with a stirring blade, a thermometer and a reflux condenser was charged with 52.3 g (0.15 mol) of the 2-hydroxy-9-(4-nonylphenoxy)propyl acrylate obtained above and 0.05 g of dibutyl tin dilaurate (1000 ppm with respect to the weight of the hydroxyl group-containing (meth)acrylic compound). The temperature was raised to 60° C. Subsequently, 32.8 g (0.125 mol) of bis-isocyanatocyclohexyl methane (hydrogenated MDI) was added dropwise over a period of 0.5 hour, resulting in an increase in reaction temperature to 80° C. After the completion of the dropwise addition, the reaction was carried out for 12 hours while controlling the reaction temperature in the range of 80 to 85° C. The percent by weight of the hydrogenated MDI in the reaction product was determined to be 0.00% by weight.

The product was discharged from the reactor. Thus, 81 g of a product which contained a urethane(meth)acrylic compound represented by the following formula was obtained.

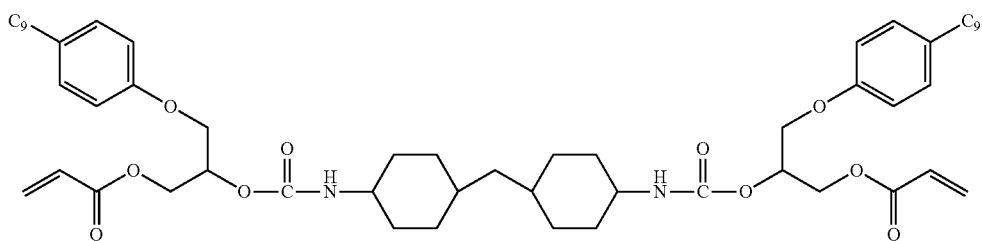

Production Examples 16 to 25

Products containing various urethane(meth)acrylic compounds were obtained by the same synthetic procedures as those in Production Example 15, except that a hydroxyl group-containing (meth)acrylic compound was produced by using an epoxy compound and an acrylic acid or a methacrylic acid illustrated in Table 12 instead of the 4-nonylphenyl glycidyl ether and the acrylic acid described in Production Example 15, and that the HMDI was replaced by a diisocyanate illustrated in Table 12.

TABLE 12

| Prod. Ex. | Epoxy compound | OH-containing (meth) acryl compound | Diisocyanate |
|---|---|---|---|
| 16 | | | |
| 17 | | | |
| 18 | | | |
| 19 | | | |
| 20 | | | |
| 21 | | | |

TABLE 12-continued

| | | | |
|---|---|---|---|
| 22 | C₉-C₆H₄-O-CH₂-epoxide | C₉-phenoxy-CH₂-CH(OH)-CH₂-O-C(=O)-C(CH₃)=CH₂ | OCN-C₆H₄-CH₂-C₆H₄-NCO |
| 23 | C₉-C₆H₄-O-CH₂-epoxide | C₉-phenoxy-CH₂-CH(OH)-CH₂-O-C(=O)-CH=CH₂ | OCN-CH₂-(norbornane)-CH₂-NCO |
| 24 | C₉-C₆H₄-O-CH₂-epoxide | C₉-phenoxy-CH₂-CH(OH)-CH₂-O-C(=O)-C(CH₃)=CH₂ | OCN-CH₂-(norbornane)-CH₂-NCO |
| 25 | C₉-C₆H₄-O-CH₂-epoxide | C₉-phenoxy-CH₂-CH(OH)-CH₂-O-C(=O)-C(CH₃)=CH₂ | OCN-CH₂-(cyclohexane)-CH₂-NCO |

| Prod. Ex. | Structural formula |
|---|---|
| 16 | Acrylate-O-CH₂-CH(O-C(=O)-NH-CH₂-(trimethylcyclohexane)-NH-C(=O)-O-CH(CH₂-O-C₆H₄-C₉)-CH₂-O-acrylate), with C₉-C₆H₄-CH₂- substituent |
| 17 | Acrylate-O-CH₂-CH(O-C(=O)-NH-C₆H₄-CH₂-C₆H₄-NH-C(=O)-O-)-CH₂-O-C₆H₄-C₉ (symmetric bis-acrylate) |
| 18 | Acrylate-O-CH₂-CH(O-C(=O)-NH-)-CH₂-O-C₆H₄-C₉ linked via methylbenzene-diyl (symmetric bis-acrylate) |

TABLE 12-continued
19 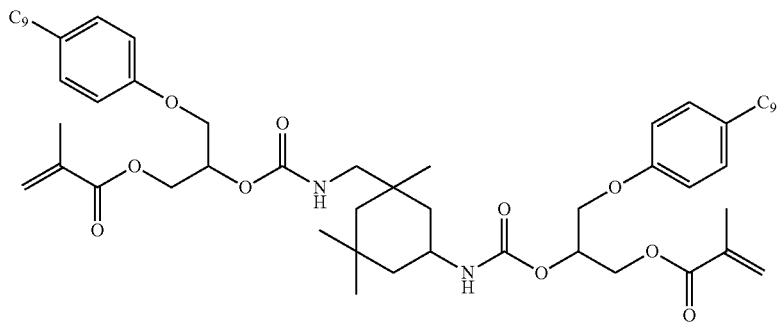
20 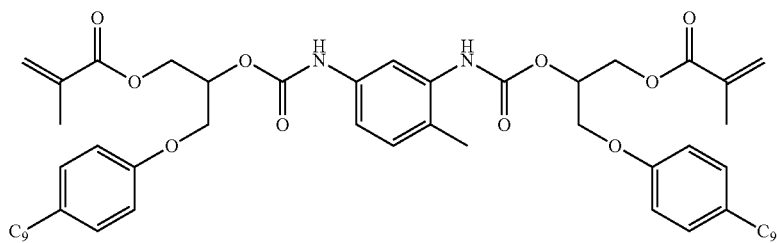
21 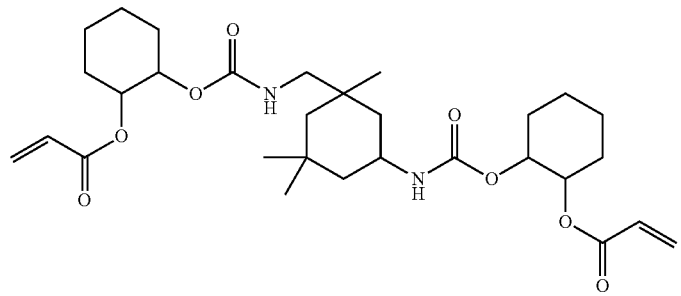 [SMILES: C=CC(=O)OC1CCCCC1OC(=O)NCC1(C)CC(NC(=O)OC2CCCCC2OC(=O)C=C)CC(C)(C)C1]
22 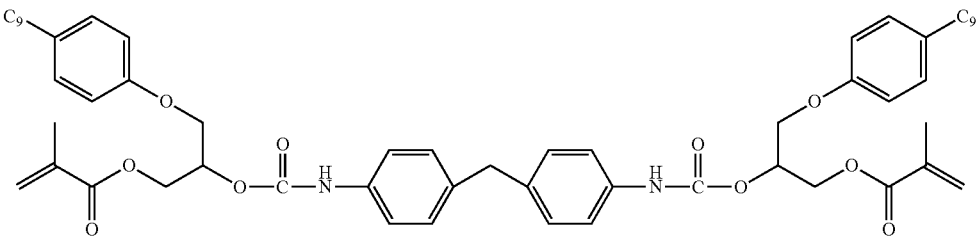
23 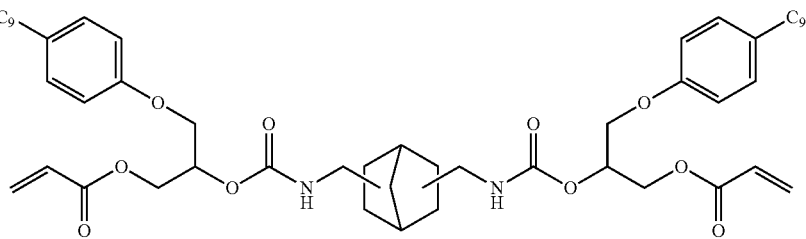
24 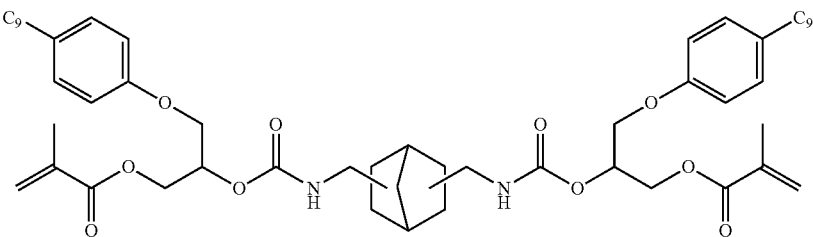

| | |
|---|---|
| 25 | 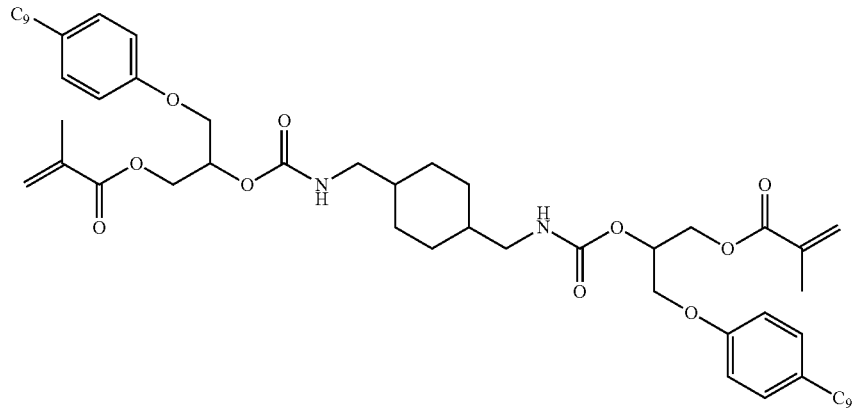 |

Production Example 26

A 300 ml-volume, four-necked flask equipped with a stirring blade, a thermometer and a reflux condenser was charged with 14.4 g (0.2 mol) of acrylic acid and 0.5 g (1.7 mmol) of tetrabutylammonium bromide serving as a catalyst. The temperature was then raised to 60° C. Subsequently, 55.3 g (0.2 mol) of 4-nonylphenyl glycidyl ether was added dropwise over a period of 0.7 hour, resulting in an increase in reaction temperature to 65° C. After the completion of the dropwise addition, the reaction was carried out for 12 hours while controlling the reaction temperature in the range of 90 to 100° C. After the completion of the reaction, the reaction liquid was cooled to room temperature, and 200 ml of toluene was added thereto. The resultant toluene solution was poured into a 500 ml-volume separatory funnel and was washed with distilled water until the pH of the aqueous layer became neutral. After the washing with water, the toluene phase was distilled using an evaporator in order to remove toluene. Thus, 60.6 g of 2-hydroxy-4-(4-nonylphenoxy)propyl acrylate was obtained (yield: 87%).

A 300 ml-volume, four-necked flask equipped with a stirring blade, a thermometer and a reflux condenser was charged with 34.8 g (0.1 mol) of the 2-hydroxy-4-(4-nonylphenoxy)propyl acrylate obtained above, 19.8 g (0.1 mol) of 1,4-cyclohexanedimethanol monoacrylate and 0.05 g of dibutyl tin dilaurate (1000 ppm with respect to the weight of the hydroxyl group-containing (meth)acrylic compounds). The temperature was raised to 60° C. Subsequently, 22.2 g (0.1 mol) of isophorone diisocyanate (IPDI) was added dropwise over a period of 0.5 hour, resulting in an increase in reaction temperature to 75° C. After the completion of the dropwise addition, the reaction was carried out for 12 hours while controlling the reaction temperature in the range of 80 to 90° C. The percent by weight of the IPDI in the reaction product was determined to be 0.00% by weight.

The product was discharged from the reactor. Thus, 72 g of a product which contained urethane(meth)acrylic compounds represented by the following formulae was obtained.

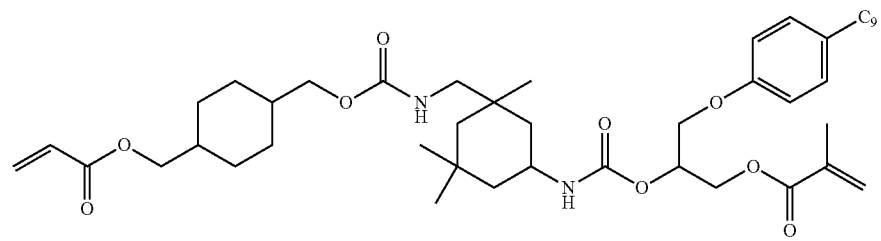

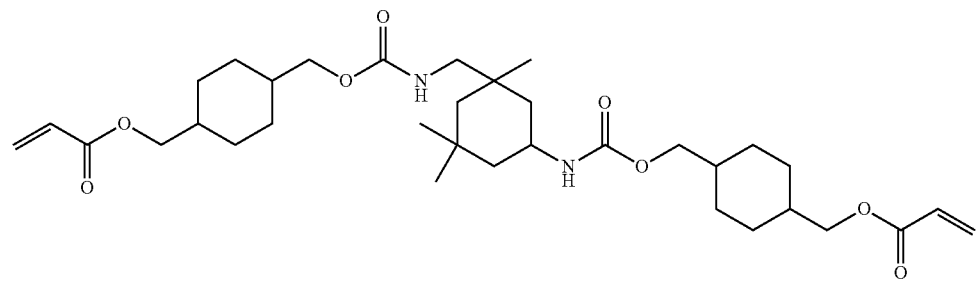

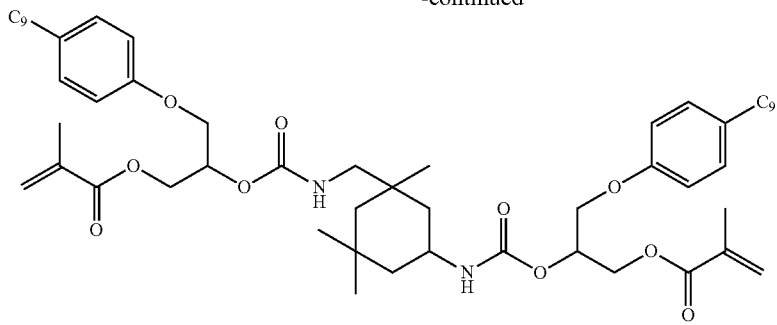

15

Production Examples 27 to 31

Products containing various urethane(meth)acrylic compounds were obtained by the same synthetic procedures as those in Production Example 26, except that the 2-hydroxy-4-(4-nonylphenoxy)propyl acrylate, the 1,4-cyclohexanedimethanol monoacrylate and the IPDI described in Production Example 26 were replaced by two kinds of hydroxyl group-containing (meth)acrylic compounds and a diisocyanate illustrated in Table 13.

TABLE 13

| Prod. Ex. | OH-containing (meth) acryl compound | Diisocyanate |
|---|---|---|
| 27 | | |
| 28 | | |
| 29 | | |

TABLE 13-continued
| | | |
|---|---|---|
| 30 | 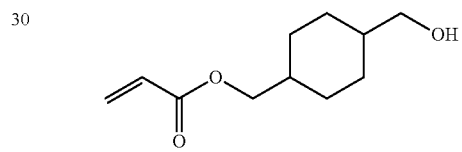 | 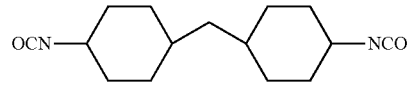 |
| | 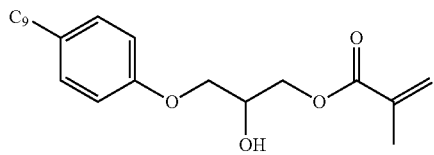 | |
| 31 | 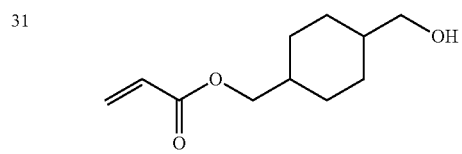 | 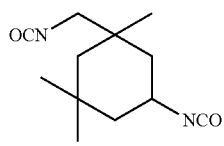 |
| | 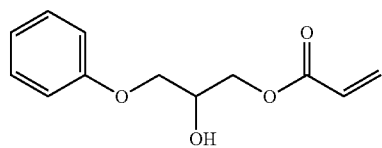 [SMILES: C=CC(=O)OCC(O)COc1ccccc1] | |
| Prod. Ex. | Structural formula |
|---|---|
| 27 | 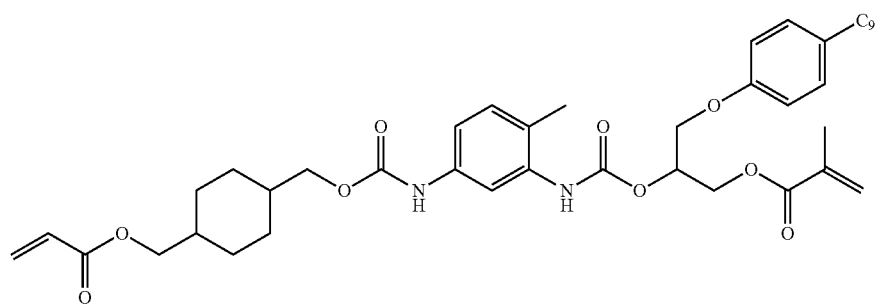 |
| | 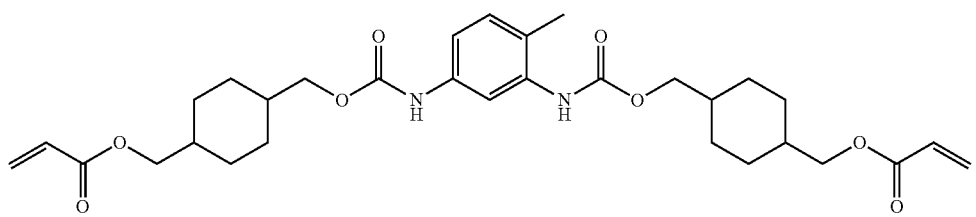 [SMILES: C=CC(=O)OCC1CCC(COC(=O)Nc2ccc(C)c(NC(=O)OCC3CCC(COC(=O)C=C)CC3)c2)CC1] |
| | 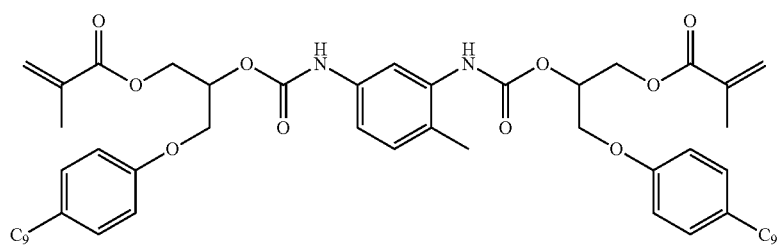 |

TABLE 13-continued
28
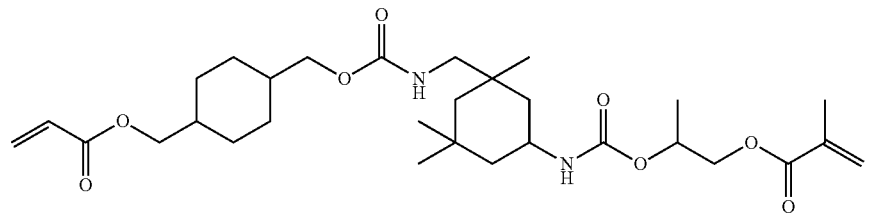 [SMILES: C=CC(=O)OCC1CCC(COC(=O)NCC2(C)CC(NC(=O)OC(C)COC(=O)C(=C)C)CC(C)(C)C2)CC1]
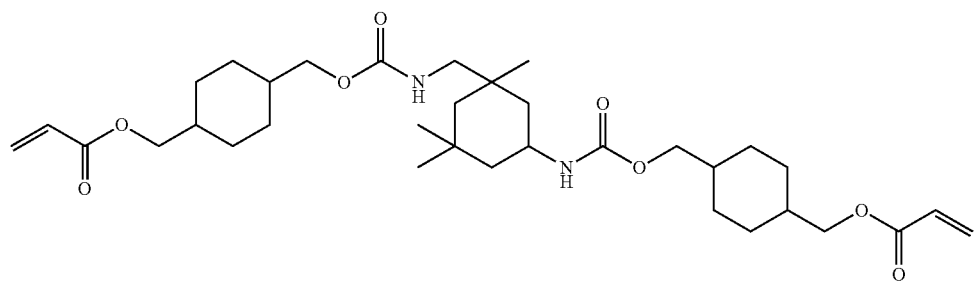 [SMILES: C=CC(=O)OCC1CCC(COC(=O)NCC2(C)CC(NC(=O)OCC3CCC(COC(=O)C=C)CC3)CC(C)(C)C2)CC1]
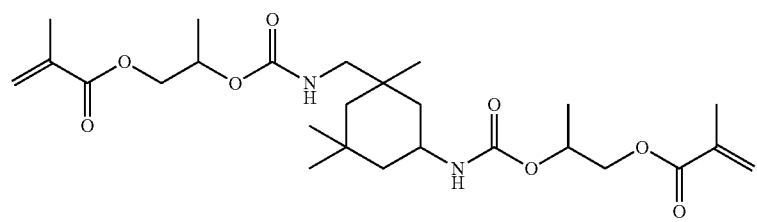 [SMILES: C=C(C)C(=O)OCC(C)OC(=O)NCC1(C)CC(NC(=O)OC(C)COC(=O)C(=C)C)CC(C)(C)C1]
29
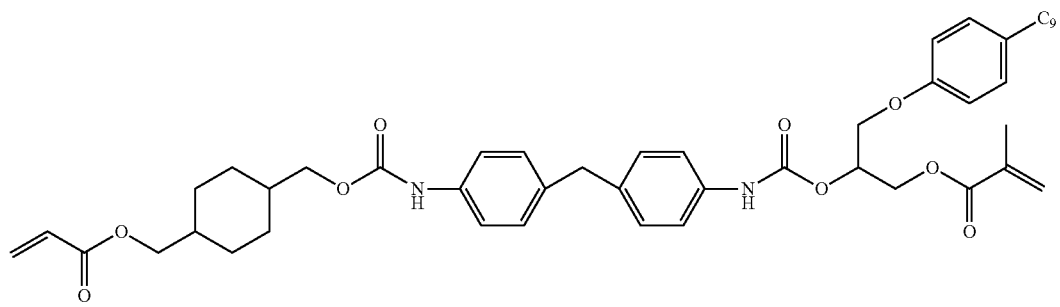
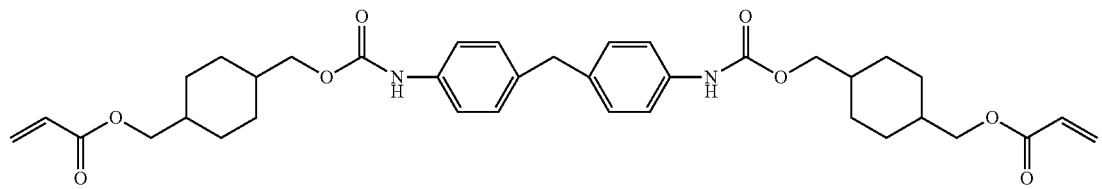 [SMILES: C=CC(=O)OCC1CCC(COC(=O)Nc2ccc(Cc3ccc(NC(=O)OCC4CCC(COC(=O)C=C)CC4)cc3)cc2)CC1]
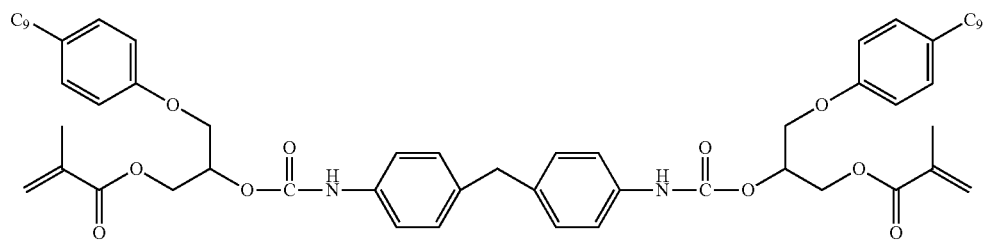

TABLE 13-continued
30
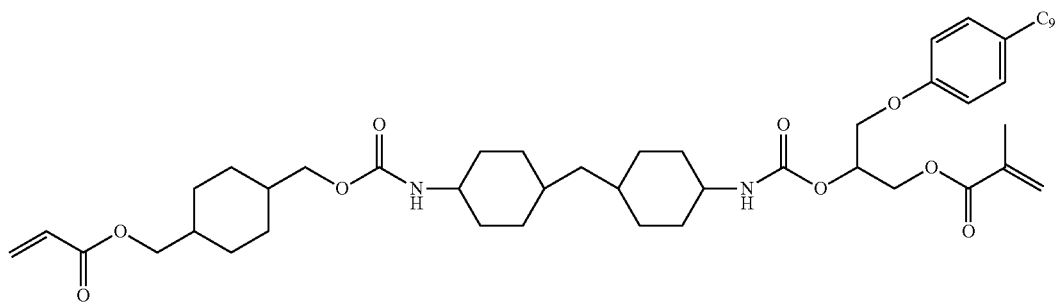
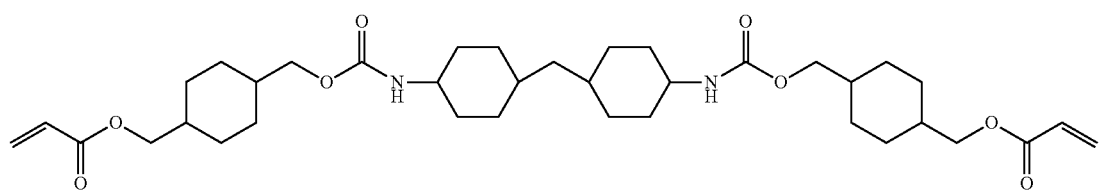 [SMILES: C=CC(=O)OCC1CCC(COC(=O)NC2CCC(CC3CCC(NC(=O)OCC4CCC(COC(=O)C=C)CC4)CC3)CC2)CC1]
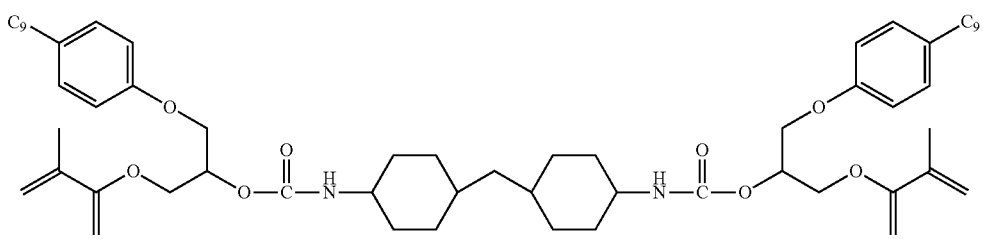
31
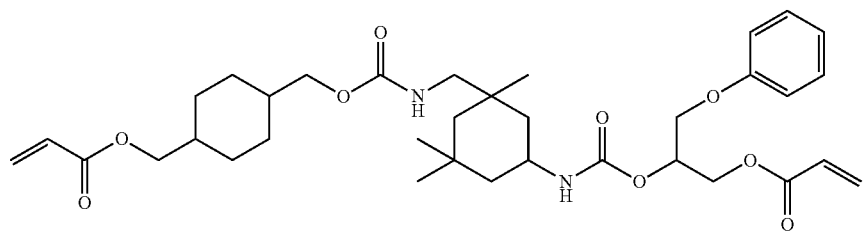 [SMILES: C=CC(=O)OCC1CCC(COC(=O)NCC2(C)CC(NC(=O)OC(COC(=O)C=C)COc3ccccc3)CC(C)(C)C2)CC1]
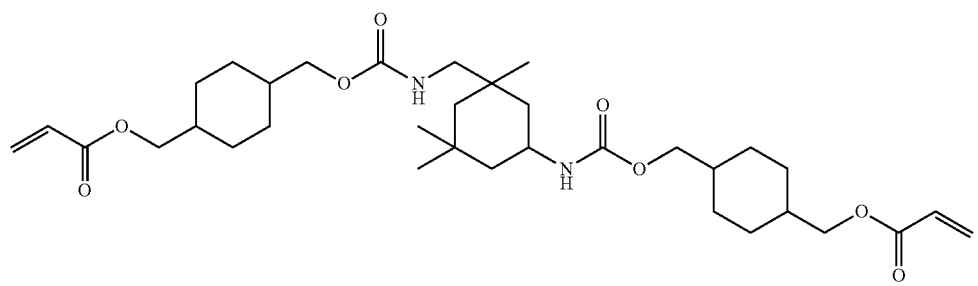 [SMILES: C=CC(=O)OCC1CCC(COC(=O)NCC2(C)CC(NC(=O)OCC3CCC(COC(=O)C=C)CC3)CC(C)(C)C2)CC1]

TABLE 13-continued

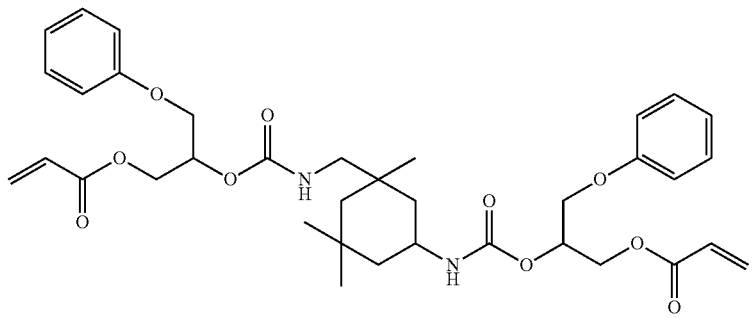 [SMILES: C=CC(=O)OCC(COc1ccccc1)OC(=O)NCC1(C)CC(NC(=O)OC(COC(=O)C=C)COc2ccccc2)CC(C)(C)C1]

FT-IR Measurement of Products Containing the Urethane (Meth)Acrylic Compounds

The products containing the urethane(meth)acrylic compounds that were obtained in Production Examples 1 to 31 were analyzed by FT-IR using an infrared spectrophotometer (FTS-6000 manufactured by Bio-Rad).

The results are described in FIGS. 1 to 31.

Examples 1 to 31

Measurement of Polymerization Shrinkage

70 Parts by weight of the product containing the urethane (meth)acrylic compound that was obtained in any of Production Examples 1 to 31 was mixed together with 30 parts by weight of triethylene glycol dimethacrylate (NK Ester 3G manufactured by Shin-Nakamura Chemical Co., Ltd.) serving as a diluent monomer for adjusting the viscosity, thereby preparing a monomer composition. Further, 0.3 part by weight of camphorquinone (manufactured by Wako Pure Chemical Industries, Ltd.) and 0.3 part by weight of ethyl N,N-dimethylaminobenzoate (manufactured by Wako Pure Chemical Industries, Ltd.) were dissolved in 100 parts by weight of the monomer composition. Thus, a photocurable monomer composition (a urethane(meth)acrylic compound composition) was prepared.

The photopolymerizable monomer composition was applied so as to fill an aluminum mold 10 mm in diameter and 2 mm in depth. The composition was sandwiched between cover glass sheets and light was applied to each surface for 3 minutes, i.e., a total time of 6 minutes using a dental visible light irradiator (a twin polymerizer manufactured by SHOFU INC.), thereby curing the photocurable monomer composition.

The density of the photocurable monomer composition was measured before and after curing with a dry density meter (Accupyc 1330 manufactured by Shimadzu Corporation). The polymerization shrinkage was determined using the following equation (1).

Polymerization shrinkage (%)=((density after polymerization−density before polymerization)/density after polymerization)×100   Equation (1)

Next, the polymerization shrinkage of triethylene glycol dimethacrylate alone was measured in the same manner as described above. As a result, the polymerization shrinkage was determined to be 13.0%.

Then, the polymerization shrinkage (S3) of the product containing the urethane(meth)acrylic compound was determined from the following equation (2) using the polymerization shrinkage (S1) of the monomer composition that was a mixture of the product containing the urethane(meth) acrylic compound and triethylene glycol dimethacrylate, and the polymerization shrinkage (S2, 13.0%) of triethylene glycol dimethacrylate alone.

(S3)=((S1)−((S2)×0.3))/0.7   Equation (2)

The results are described in Tables 14 to 16.

Examples 1 to 24 and 26 to 31

Measurement of Viscosity

60 Parts by weight of the product containing the urethane (meth)acrylic compound that was obtained in any of Production Examples 1 to 23, 28 and 29 was mixed together with 40 parts by weight of triethylene glycol dimethacrylate (NK Ester 3G) serving as a diluent monomer for adjusting the viscosity, thereby preparing a monomer composition.

Further, 40 parts by weight of the product containing the urethane(meth)acrylic compound that was obtained in any of Production Examples 24, 26, 27, 30 and 31 was mixed together with 60 parts by weight of triethylene glycol dimethacrylate, thereby preparing a monomer composition.

Then, the viscosity at 30° C. of these monomer compositions was measured with an E-type viscometer (TV-22 manufactured by TOKI SANGYO CO., LTD.). As a cone rotor, No 4 was used. Triethylene glycol dimethacrylate had a viscosity of 10 (mPa·s, 30° C.).

The results are described in Tables 14 to 16.

Comparative Examples 1 and 2

Bis-GMA (D-GMA manufactured by Shin-Nakamura Chemical Co., Ltd.) or UDMA (SH500S manufactured by Negami Chemical Industrial Co., Ltd.) was used as a methacrylate monomer in place of the products containing the urethane(meth)acrylic compounds from the above Examples. 60 parts by weight of Bis-GMA or UDMA was mixed together with 40 parts by weight of triethylene glycol dimethacrylate (NK Ester 3G), thereby preparing a monomer composition.

Then, in Comparative Example 1, similarly to the above Examples, the viscosity at 30° C. of the composition was measured with an E-type viscometer (TV-22).

Then, similarly to the above Examples, 0.3 part by weight of camphorquinone (manufactured by Wako Pure Chemical Industries, Ltd.) and 0.3 part by weight of ethyl N,N-dimethylaminobenzoate (manufactured by Wako Pure Chemical Industries, Ltd.) were dissolved in 100 parts by weight of the monomer composition. Thus, a photocurable monomer composition (urethane(meth)acrylic compound composition) was prepared. Then, by the same method as described above, the polymerization shrinkage (S4) of the monomer composition was determined.

Further, the polymerization shrinkage (S5) of Bis-GMA or UDMA alone was determined from the following equation (3) using the polymerization shrinkage (S4) of the monomer composition and the polymerization shrinkage (S2, 13.0%) of triethylene glycol dimethacrylate alone.

$$(S5) = ((S4) - ((S2) \times 0.4))/0.6 \qquad \text{Equation (3)}$$

The results are described in Table 16.

TABLE 14

| Ex. | Corr. Prod. Ex. | Structural formula |
|---|---|---|
| 1 | 1 | |
| 2 | 2 | |
| 3 | 3 | |
| 4 | 15 | |
| 5 | 16 | |

TABLE 14-continued
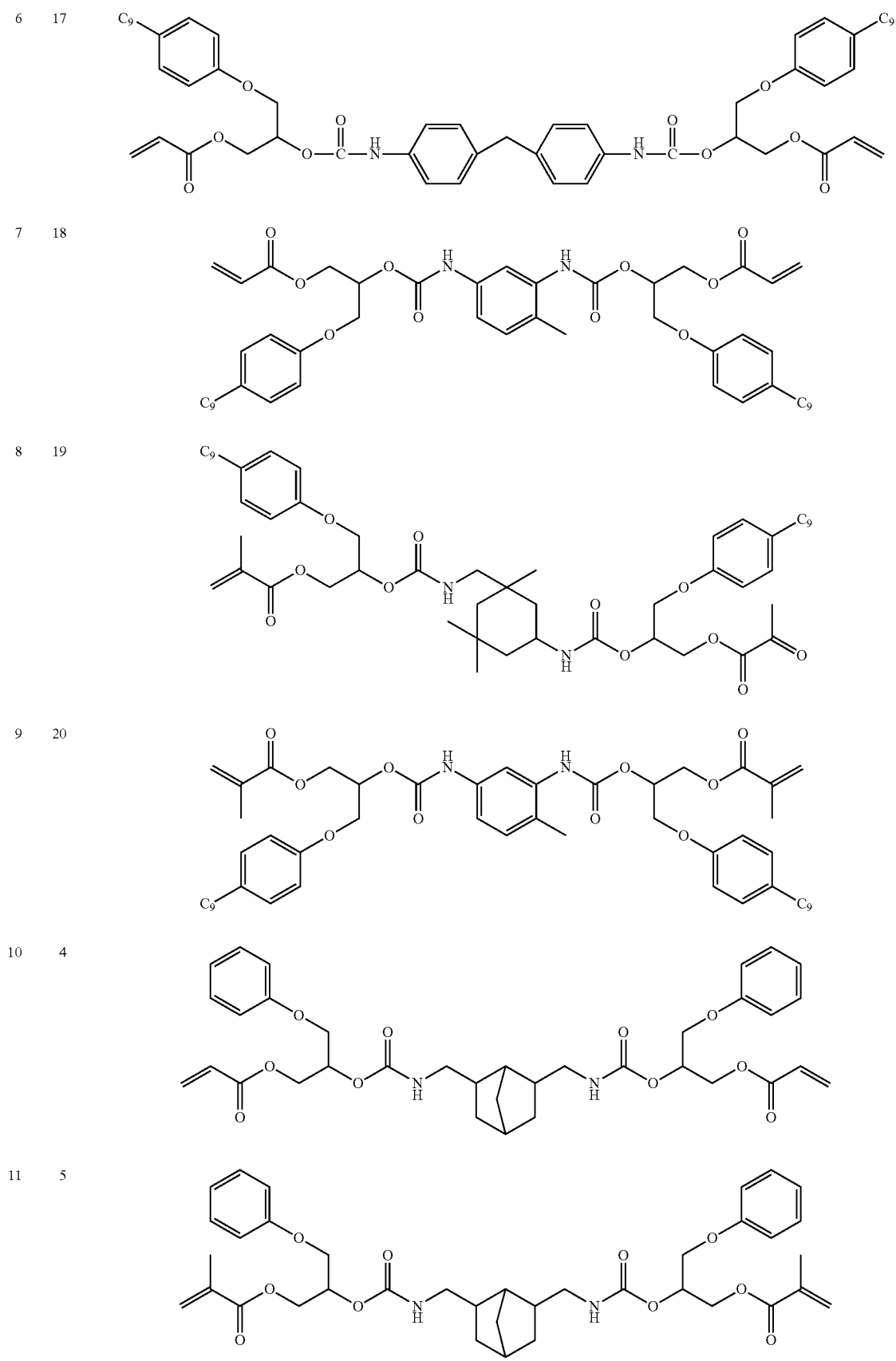

TABLE 14-continued
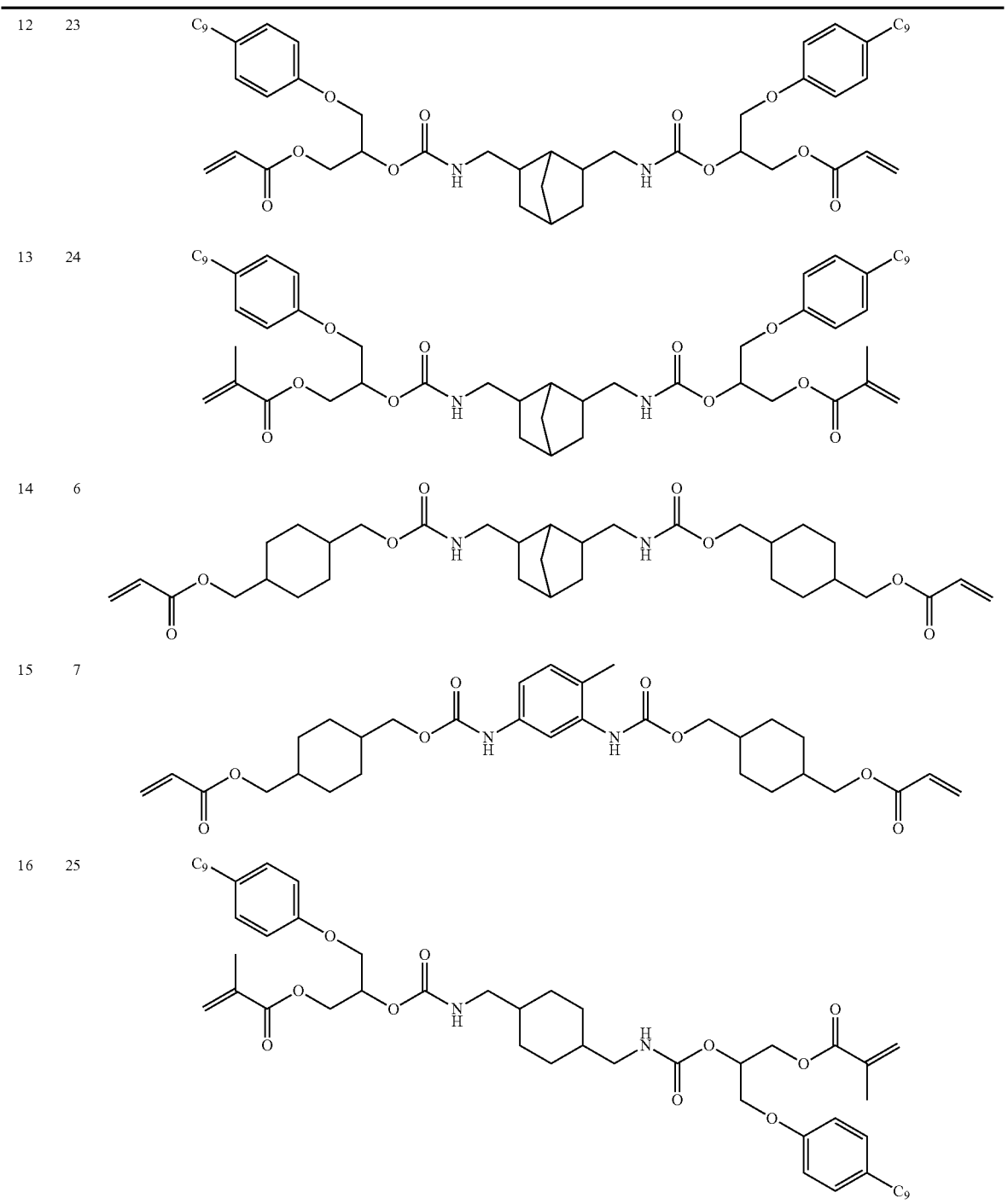
| Ex. | Polymerization shirinkage (%) | Viscosity (mPa · s 30° C.) |
|---|---|---|
| 1 | 3.0 | 888 |
| 2 | 3.6 | 714 |
| 3 | 2.5 | 684 |
| 4 | 1.6 | 1864 |
| 5 | 1.9 | 1121 |
| 6 | 1.3 | 2147 |
| 7 | 1.8 | 1915 |
| 8 | 2.5 | 707 |
| 9 | 1.5 | 1067 |
| 10 | 3.6 | 837 |

TABLE 14-continued
| | | |
|---|---|---|
| 11 | 4.0 | 696 |
| 12 | 2.4 | 1060 |
| 13 | 2.9 | 881 |
| 14 | 3.3 | 835 |
| 15 | 2.7 | 1272 |
| 16 | 2.9 | 1393 |
TABLE 15
| Ex. | Corr. Prod. Ex. | Structural formula |
|---|---|---|
| 17 | 26 | 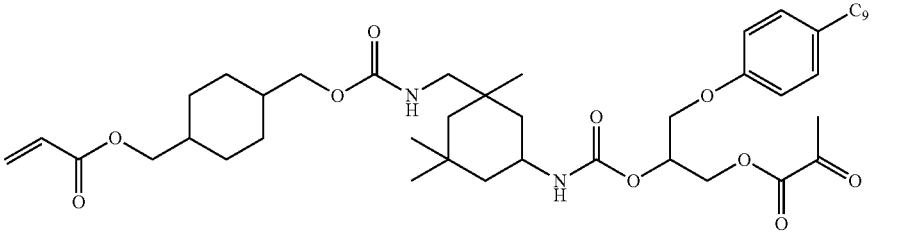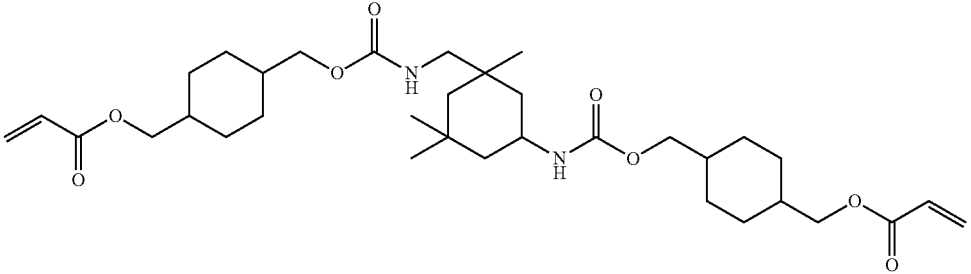 [SMILES: C=CC(=O)OCC1CCC(COC(=O)NCC2(C)CC(NC(=O)OCC3CCC(COC(=O)C=C)CC3)CC(C)(C)C2)CC1]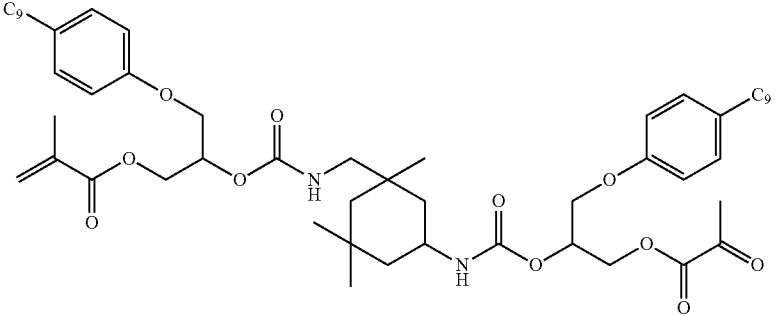 |
| 18 | 27 | 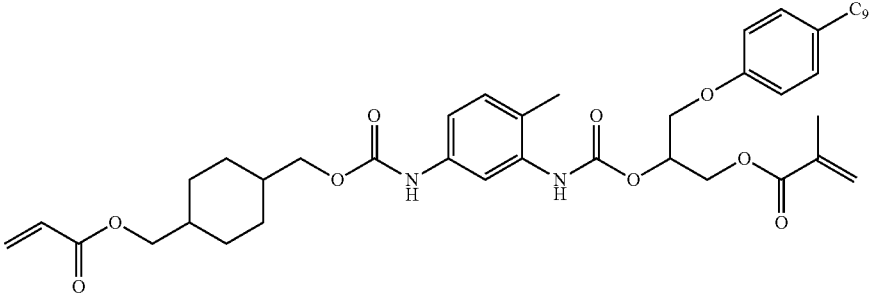 |

TABLE 15-continued
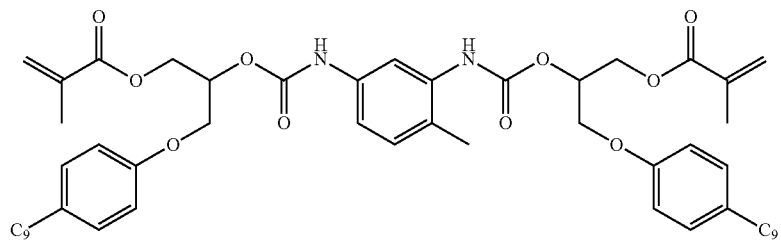
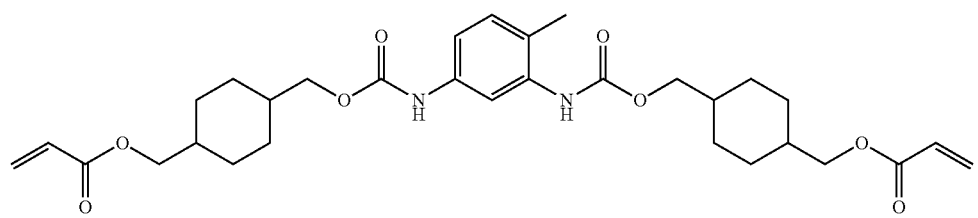 [SMILES: C=CC(=O)OCC1CCC(COC(=O)Nc2ccc(C)c(NC(=O)OCC3CCC(COC(=O)C=C)CC3)c2)CC1]
| 19 | 28 |
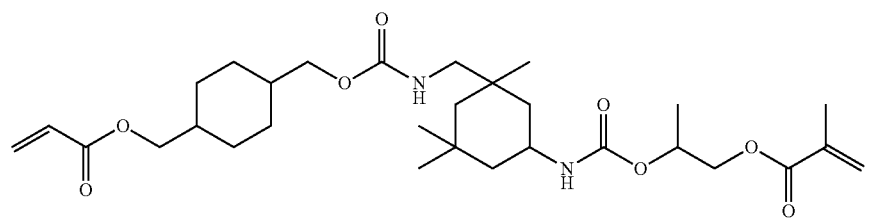 [SMILES: C=CC(=O)OCC1CCC(COC(=O)NCC2(C)CC(NC(=O)OC(C)COC(=O)C(=C)C)CC(C)(C)C2)CC1]
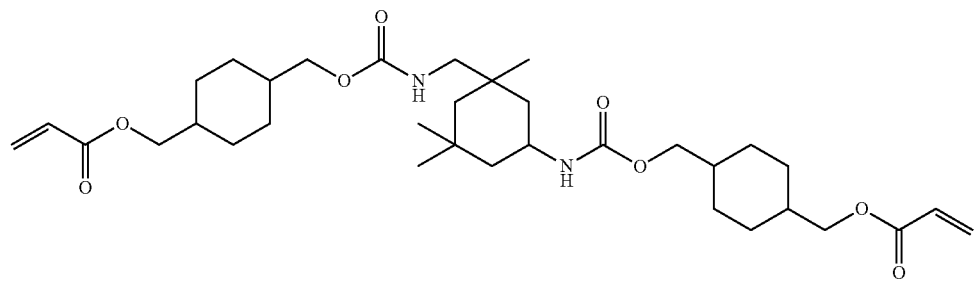 [SMILES: C=CC(=O)OCC1CCC(COC(=O)NCC2(C)CC(NC(=O)OCC3CCC(COC(=O)C=C)CC3)CC(C)(C)C2)CC1]
| 20 | 29 |
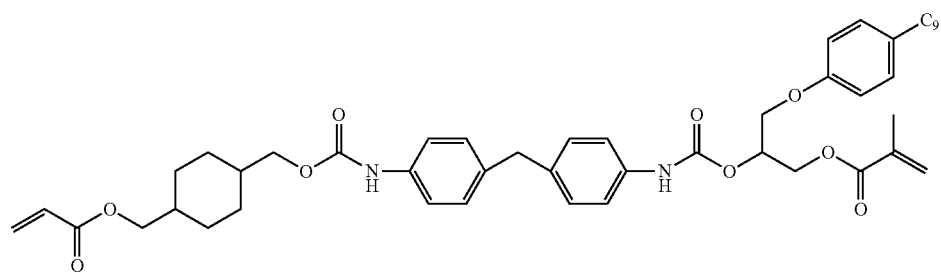

TABLE 15-continued
| | |
|---|---|
| 21 | 30 |
| 22 | 31 |
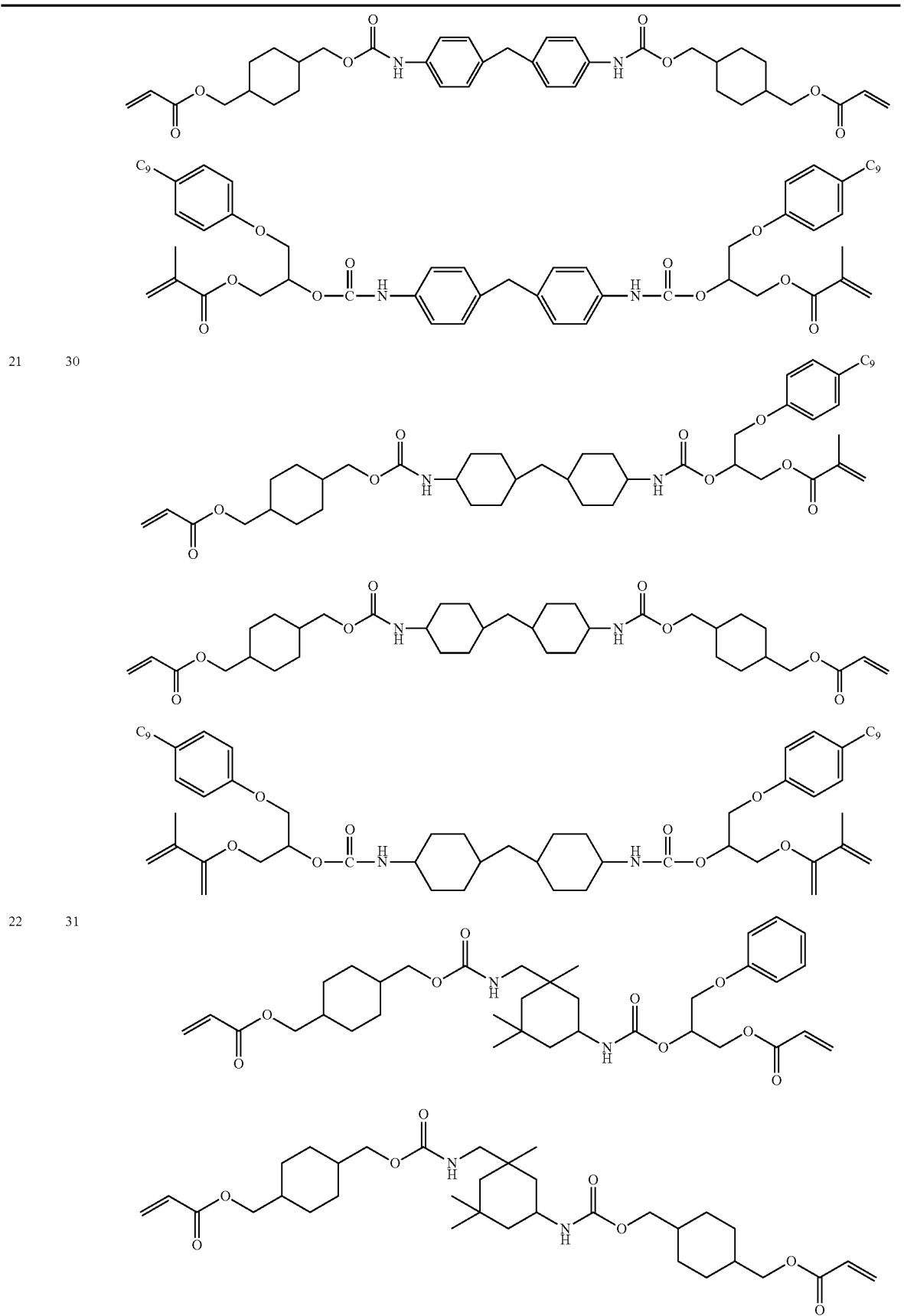

TABLE 15-continued
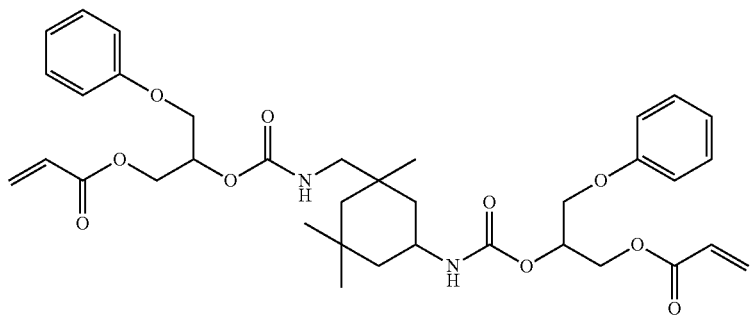 [SMILES: C=CC(=O)OCC(COc1ccccc1)OC(=O)NCC1(C)CC(NC(=O)OC(COC(=O)C=C)COc2ccccc2)CC(C)(C)C1]
| Ex. | Polymerization shrinkage (%) | Viscosity (mPs · s 30° C.) |
|---|---|---|
| 17 | 2.5 | 988 |
| 18 | 2.6 | 1228 |
| 19 | 3.4 | 624 |
| 20 | 1.5 | 3763 |
| 21 | 2.8 | 1472 |
| 22 | 3.2 | 921 |
| 23 | 2.8 | 1653 |
TABLE 16
| Ex. | Corr. Prod. Ex. | Structural formula |
|---|---|---|
| 24 | 8 | 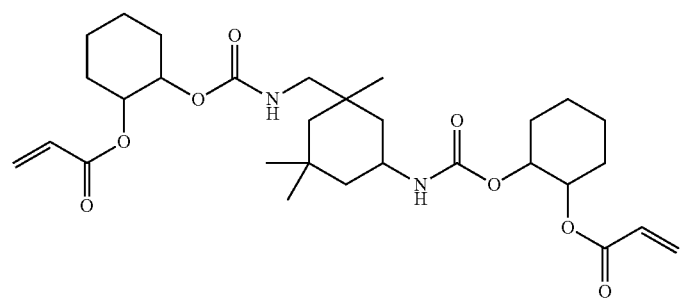 [SMILES: C=CC(=O)OC1CCCCC1OC(=O)NCC1(C)CC(NC(=O)OC2CCCCC2OC(=O)C=C)CC(C)(C)C1] |
| 25 | 9 | 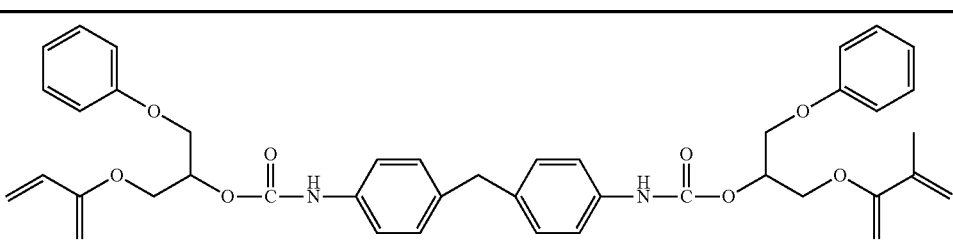 |

TABLE 16-continued
| 26 | 10 | 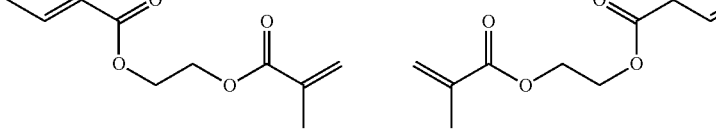 |
| 27 | 11 | 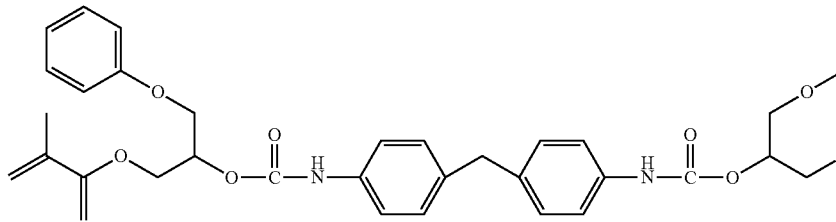 |
| 28 | 22 | 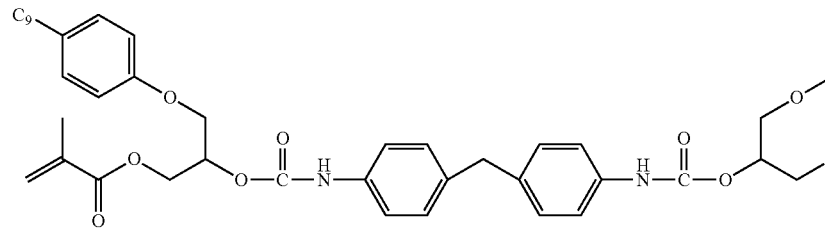 |
| 29 | 12 | 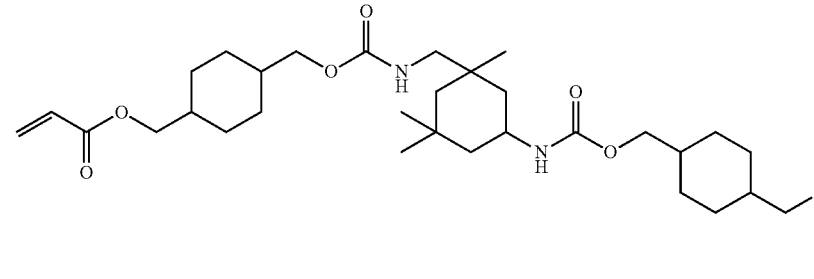 |
| 30 | 13 | 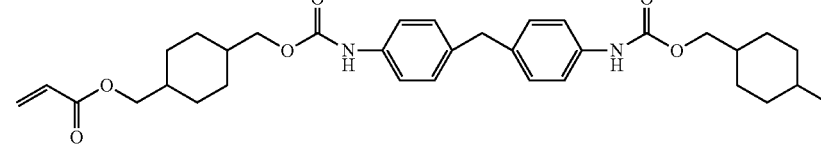 |
| 31 | 14 | 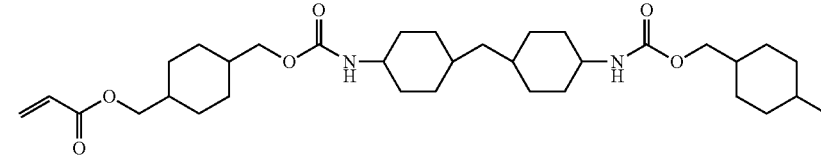 |
| Comp. Ex. 1 | Bis-GMA | 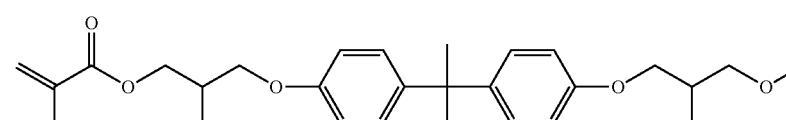 |

TABLE 16-continued

| | | Comp. Ex. 2 | UDMA structure |

| Ex. | Polymerization shrinkage (%) | Viscosity (mPa · s 30° C.) |
|---|---|---|
| 24 | 0.8 | 445 (3G 60%) |
| 25 | 1.9 | no data |
| 26 | 3.9 | 108 (3G 60%) |
| 27 | 2.2 | 133 (3G 60%) |
| 28 | 1.5 | 2918 |
| 29 | 2.9 | 806 |
| 30 | 2.2 | 209 (3G 60%) |
| 31 | 3.1 | 315 (3G 60%) |
| Comp. Ex. 1 | 5.2 | 527 |
| Comp. Ex. 2 | 7.2 | no data |

Examples 32 to 37

Measurement of Polymerization Shrinkage and Viscosity

40 Parts by weight of the product containing the urethane (meth)acrylic compound that was obtained in any of Production Examples 3, 12 and 16 was mixed together with 60 parts by weight of DCP-4EO-A (compound represented by Formula (6) wherein R is a hydrogen atom and m+n=4) or DCP-A (compound represented by Formula (6) wherein R is a hydrogen atom and m+n=0), serving as a diluent monomer for adjusting the viscosity, thereby preparing a monomer composition. Similarly to the above Examples, the viscosity at 30° C. of the composition was measured with an E-type viscometer (TV-22).

Then, similarly to the above Examples, 0.3 part by weight of camphorquinone (manufactured by Wako Pure Chemical Industries, Ltd.) and 0.3 part by weight of ethyl N, N-dimethylaminobenzoate (manufactured by Wako Pure Chemical Industries, Ltd.) were dissolved in 100 parts by weight of the monomer composition. Thus, a photocurable monomer composition (a urethane(meth)acrylic compound composition) was prepared. Then, in the same manner as described above, using the equation (1), from the density of the photocurable monomer composition measured before and after curing, the polymerization shrinkage of the photocurable monomer composition was determined.

Further, in the same manner as described above, the polymerization shrinkage and the viscosity of DCP-4EO-A and DCP-A alone were measured. It was found that DCP-4EO-A had a polymerization shrinkage of 8.0% and a viscosity of 130 (mPa·s, 30° C.), and DCP-A had a polymerization shrinkage of 8.3% and a viscosity of 110 (mPa·s, 30° C.).

The results are described in Table 17.

Comparative Example 3

The viscosity and the polymerization shrinkage were determined by the same procedures as those in Examples 32 to 37, except for using a monomer composition obtained by mixing 40 parts by weight of Bis-GMA (D-GMA) together with 60 parts by weight of DCP-4EO-A.

The results are described in Table 17.

TABLE 17

| Ex. | Corr. Prod. Ex. | Diluent monomer | Structural formula |
|---|---|---|---|
| 32 | 3 | DCP-4EO-A | |

TABLE 17-continued
| | | | |
|---|---|---|---|
| 33 | 16 | DCP-4EO-A | 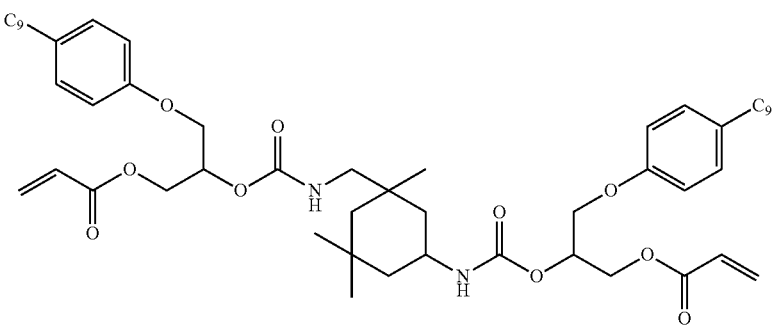 |
| 34 | 12 | DCP-4EO-A | 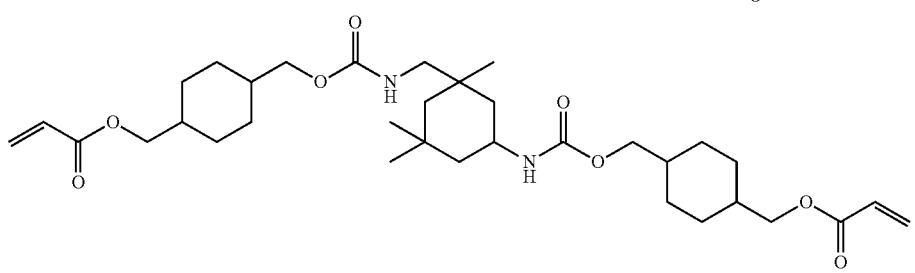 |
| 35 | 3 | DCP-A | 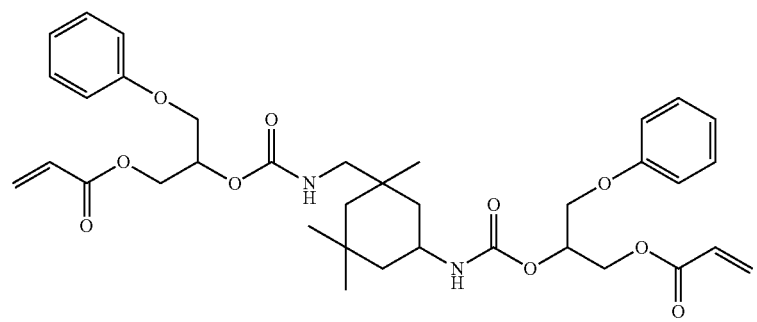 [SMILES: C=CC(=O)OCC(COc1ccccc1)OC(=O)NCC1(C)CC(NC(=O)OC(COC(=O)C=C)COc2ccccc2)CC(C)(C)C1] |
| 36 | 16 | DCP-A | 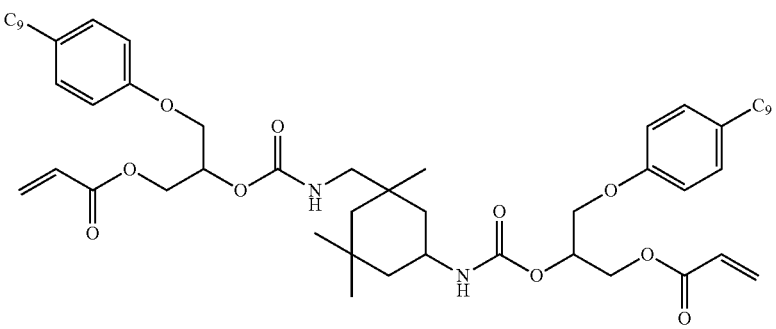 |
| 37 | 12 | DCP-A | 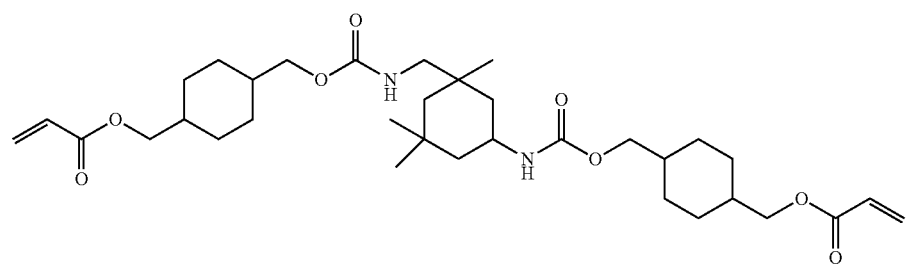 [SMILES: C=CC(=O)OCC1CCC(COC(=O)NCC2(C)CC(NC(=O)OCC3CCC(COC(=O)C=C)CC3)CC(C)(C)C2)CC1] |

TABLE 17-continued

| Comp. Ex. 3 | Bis-GMA | DCP-4EO-A | (structure) |

| Ex. | Polymerization shrinkage (%) | Viscosity (mPa · s 30° C.) |
|---|---|---|
| 32 | 5.4 | 1850 |
| 33 | 5.2 | 2143 |
| 34 | 5.6 | 1673 |
| 35 | 5.7 | 2281 |
| 36 | 5.4 | 3039 |
| 37 | 5.8 | 2433 |
| Comp. Ex. 3 | 6.6 | 1250 |

Examples 100 to 112

Measurement of Polymerization Shrinkage of Photocurable Pastes

Parts by weight of the photocurable monomer composition obtained in any of Examples 1 to 31 was mixed together with 60 parts by weight of barium glass (GM8235 manufactured by NEC SCHOTT Components Corporation) which had been surface treated with 10 parts by weight of γ-methacryloxypropyl trimethoxysilane (KBM503 manufactured by Shin-Etsu Chemical Co., Ltd.) and had an average particle diameter of 1 μm. Thus, a uniform photocurable paste (a urethane(meth)acrylic compound composition) was prepared.

With respect to the photocurable pastes, the polymerization shrinkage was measured in the same manner as described for the photocurable monomer composition in Example 1.

The results are described in Tables 18 to 20.

Comparative Examples 10 and 11

Photocurable pastes were prepared in the same manner as described in Example 100, except that the product containing the urethane(meth)acrylic compound from the above Examples was replaced by Bis-GMA (D-GMA manufactured by Shin-Nakamura Chemical Co., Ltd.) or UDMA (SH500S manufactured by Negami Chemical Industrial Co., Ltd.), which was a methacrylate monomer.

With respect to the photocurable pastes, the polymerization shrinkage was measured in the same manner as described for the photocurable monomer composition in Example 1.

The results are described in Table 20.

TABLE 18

| Ex. | Corr. Prod. Ex. | Structural formula | Polymerization shrinkage (%) |
|---|---|---|---|
| 100 | 3 | (structure) | 2.3 |
| 101 | 15 | (structure) | 2.0 |

TABLE 18-continued

| Ex. | Corr. Prod. Ex. | Structural formula | Polymerization shrinkage (%) |
|---|---|---|---|
| 102 | 16 | | 2.1 |
| 103 | 17 | | 1.9 |
| 104 | 4 | | 2.6 |
| 105 | 24 | | 2.4 |
| 106 | 7 | | 2.3 |

TABLE 19
| Ex. | Corr. Prod. Ex. | Structural formula | Polymerization shrinkage (%) |
|---|---|---|---|
| 107 | 26 | 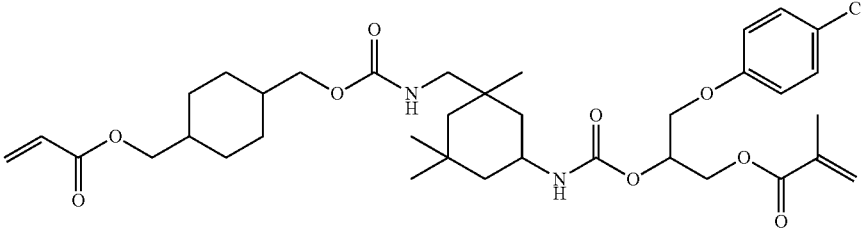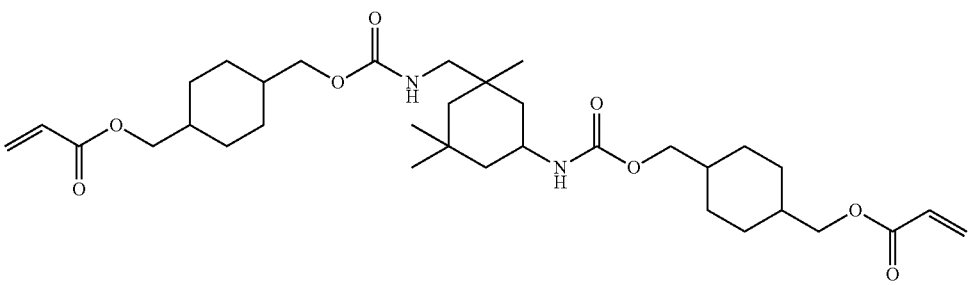 [SMILES: C=CC(=O)OCC1CCC(COC(=O)NCC2(C)CC(NC(=O)OCC3CCC(COC(=O)C=C)CC3)CC(C)(C)C2)CC1]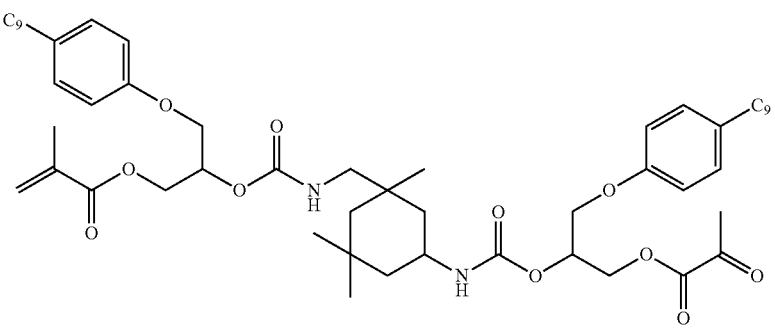 | 2.3 |
| 108 | 27 | 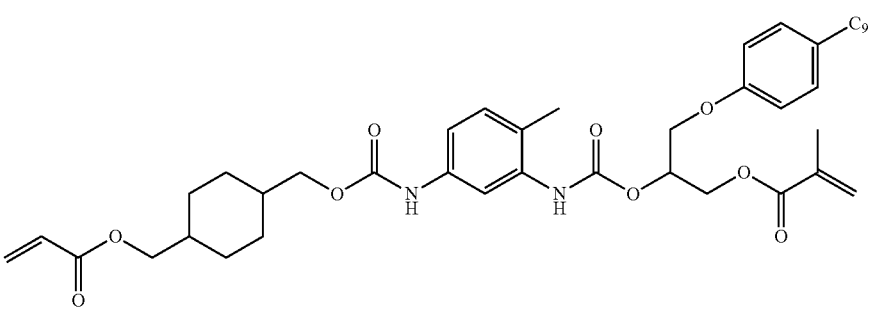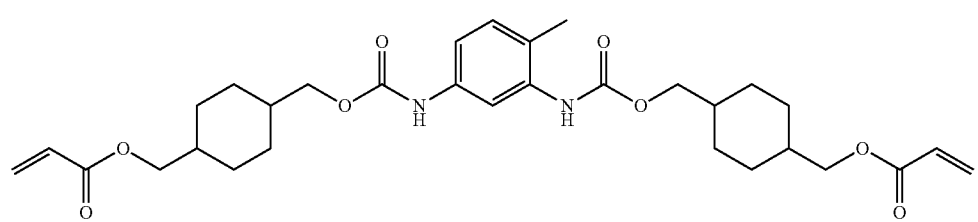 [SMILES: C=CC(=O)OCC1CCC(COC(=O)Nc2ccc(C)c(NC(=O)OCC3CCC(COC(=O)C=C)CC3)c2)CC1] | 2.3 |

TABLE 19-continued
| Ex. | Corr. Prod. Ex. | Structural formula | Polymerization shrinkage (%) |
|---|---|---|---|
| | | 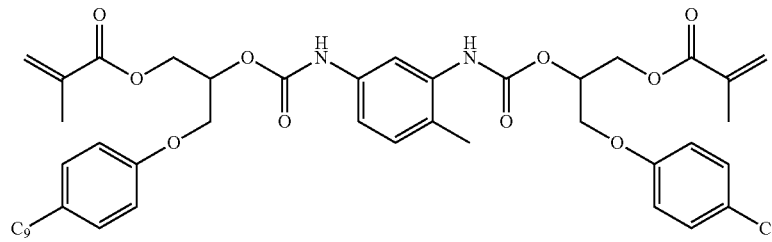 | |
| 109 | 28 | 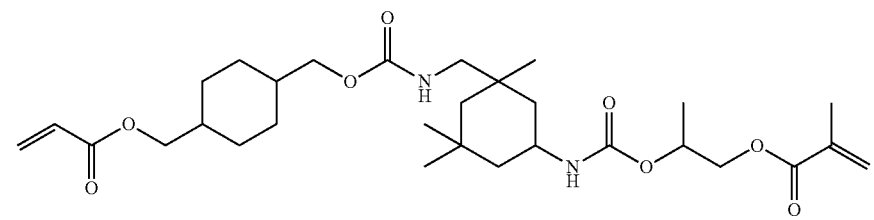 [SMILES: C=CC(=O)OCC1CCC(COC(=O)NCC2(C)CC(NC(=O)OC(C)COC(=O)C(=C)C)CC(C)(C)C2)CC1]<br>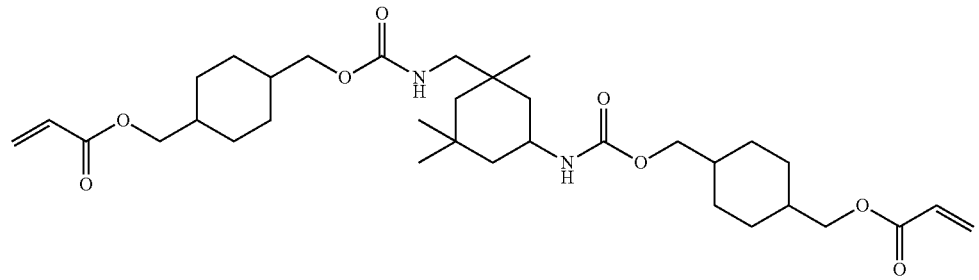 [SMILES: C=CC(=O)OCC1CCC(COC(=O)NCC2(C)CC(NC(=O)OCC3CCC(COC(=O)C=C)CC3)CC(C)(C)C2)CC1]<br>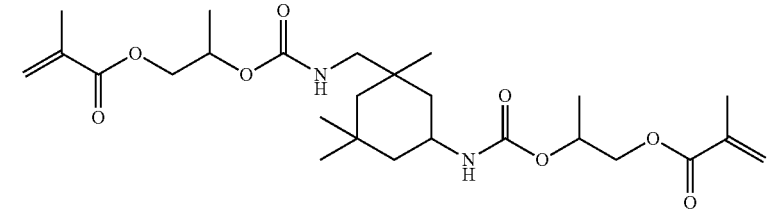 [SMILES: C=C(C)C(=O)OCC(C)OC(=O)NCC1(C)CC(NC(=O)OC(C)COC(=O)C(=C)C)CC(C)(C)C1] | 2.5 |
TABLE 20
| Ex. | Corr. Prod. Ex. | Structural formula |
|---|---|---|
| 110 | 21 | 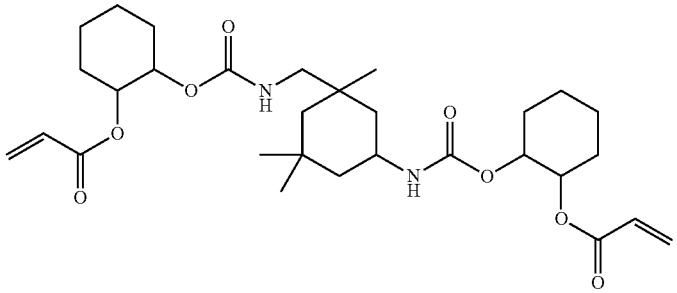 [SMILES: C=CC(=O)OC1CCCCC1OC(=O)NCC1(C)CC(NC(=O)OC2CCCCC2OC(=O)C=C)CC(C)(C)C1] |

TABLE 20-continued

| | | Ex. | Polymerization shrinkage (%) |
|---|---|---|---|
| | | 110 | 2.3 |
| | | 111 | 2.1 |
| | | 112 | 2.2 |
| | | Comp. 10 | 3.0 |
| | | Comp. 11 | 3.6 |

What is claimed is:

1. A compound having the structure of Formula (1):

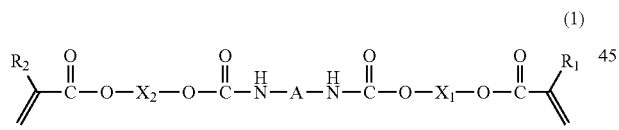

wherein in Formula (1), $R_1$ and $R_2$ both indicate hydrogen atoms, A is a divalent organic group selected from the group consisting of structures (a) to (h) described below, $X_1$ and $X_2$ each indicate a divalent organic group, at least one of $X_1$ and $X_2$ is a divalent organic group selected from the group consisting of structures (i) to (m) described below, and the groups A, $X_1$ and $X_2$ have three or more ring structures in total (with the proviso that the compound is not a compound in which A is the structure (c) or (d) and $X_1$ and $X_2$ are both the structures (i) in which $R_3$ is a phenyl group, a compound in which A is the structure (a), $R_1$ and $R_2$ are both methyl groups and $X_1$ and $X_2$ are both the structures (i) in which $R_3$ is a phenyl group, a compound having the structure of Formula (2-7) or a compound having the structure of Formula (4)):

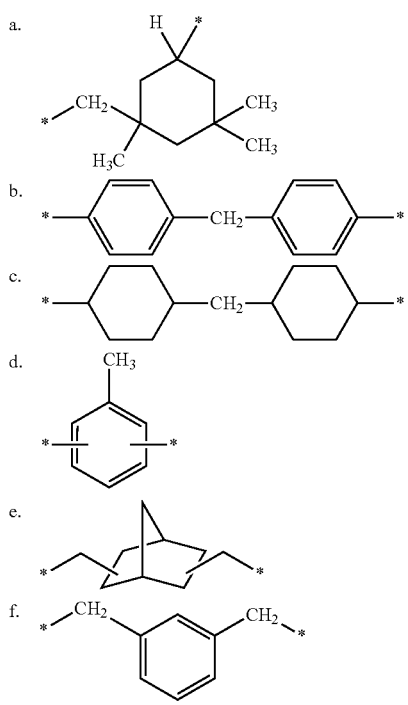

-continued

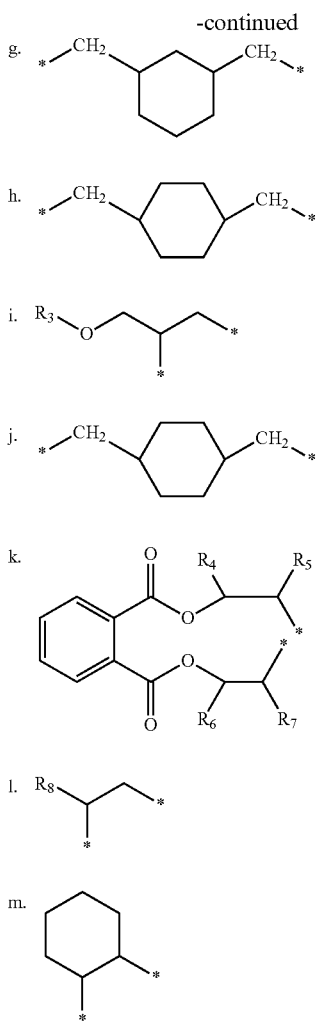

wherein with respect to the organic groups (a) to (m), R₃ is an aryl group or a cycloalkyl group which may have a substituent, R₄, R₅, R₆ and R₇ each independently indicate a hydrogen atom or a methyl group, and R₈ is an alkyl group having 4 to 20 carbon atoms,

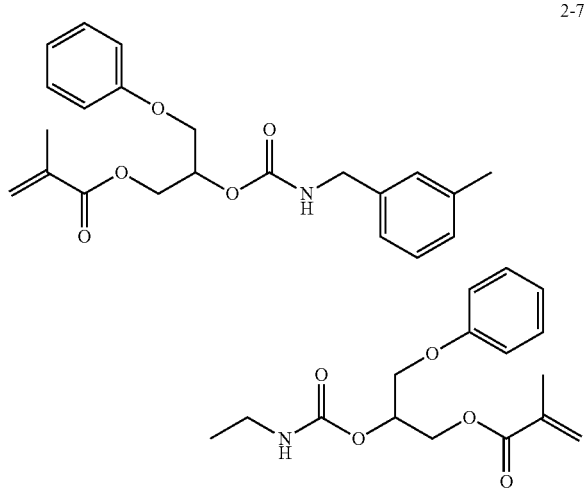

(2-7)

-continued

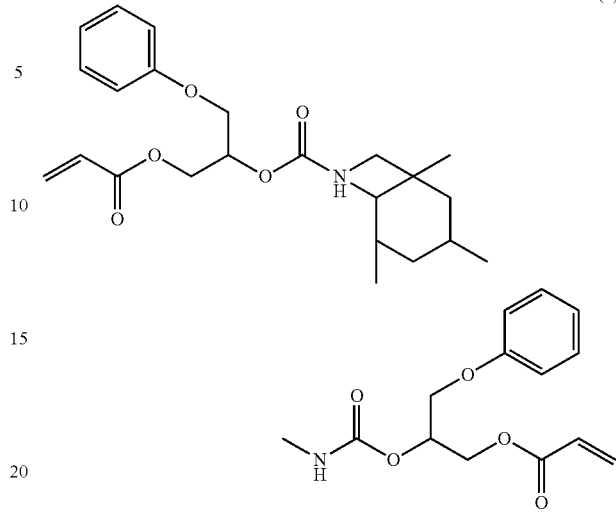

(4)

2. The compound according to claim 1, which has the structure of Formula (1) in which the group A is a divalent organic group selected from the group consisting of the structures (a), (b), (c), (d), (e) and (h).

3. The compound according to claim 1, which has the structure of Formula (1) in which the group A is a divalent organic group selected from the group consisting of the structures (a), (c), (e) and (h).

4. The compound according to claim 1, which has the structure of Formula (1) in which the group A is a divalent organic group selected from the group consisting of the structures (a), (e) and (h).

5. The compound according to claim 1, which has the structure of Formula (1) in which the divalent organic group A is the structure (a).

6. The compound according to claim 1, which has the structure of Formula (1) in which at least one of $X_1$ and $X_2$ is a divalent organic group selected from the group consisting of the structures (i), (j), (l) and (m).

7. The compound according to claim 1, which has the structure of Formula (1) in which one of $X_1$ and $X_2$ is a divalent organic group selected from the group consisting of the structures (i), (j) and (m).

8. The compound according to claim 1, which has the structure of Formula (1) in which the group A is any of the structures (a), (b), (c) and (e) and $X_1$ and $X_2$ are both the structures (i).

9. The compound according to claim 1, which has the structure of Formula (1) with the proviso that the compound is not:
  a compound in which A is the structure (a), (b), (c) or (d) and $X_1$ and $X_2$ are both the structures (i) in which $R_3$ is a phenyl group,
  a compound in which A is the structure (a), (b), (c) or (d) and $X_1$ and $X_2$ are both the structures (1) in which $R_3$ is an alkyl group having 4 to 20 carbon atoms,
  a compound in which A is the structure (a), $R_1$ and $R_2$ are both methyl groups and $X_1$ and $X_2$ are both the structures (i) in which $R_3$ is a phenyl group,
  a compound having the structure of Formula (2-7) or
  a compound having the structure of Formula (4).

10. The compound according to claim 1, which is a compound selected from compounds having the structures of Formulas (2), (3) and (5) below:

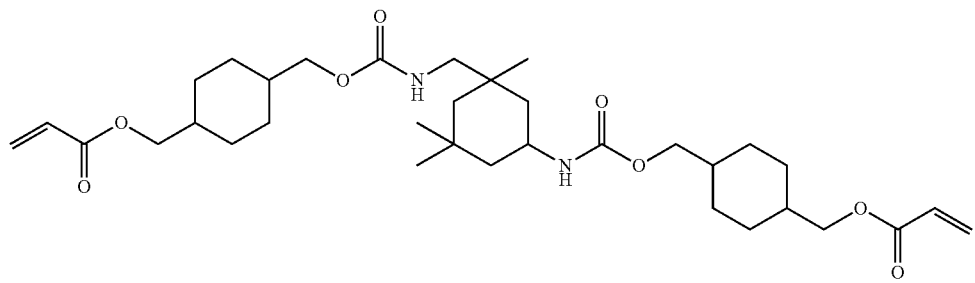

(2)

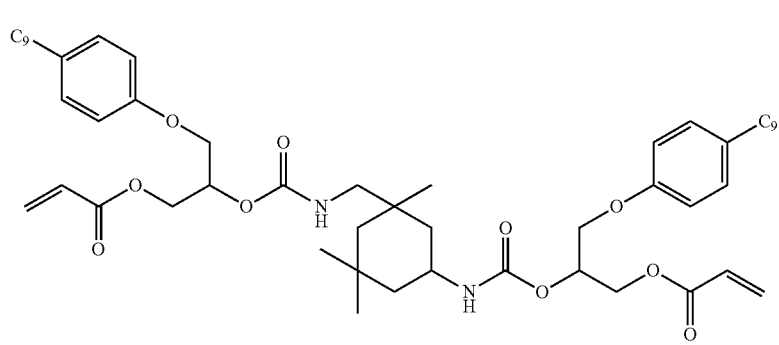

(3)

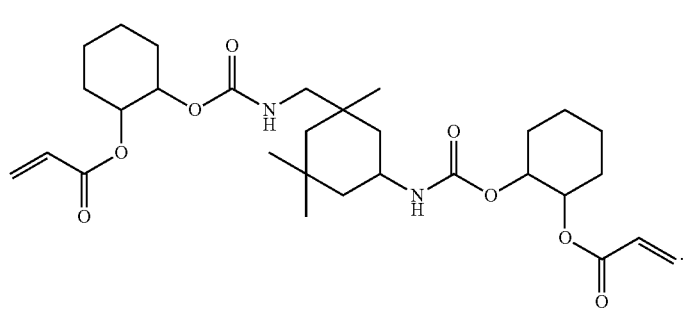

(5)

11. A composition which comprises the compound according to claim 1.

12. The composition according to claim 11, further comprising a polymerization initiator (B) and a filler (C).

13. The composition according to claim 11, further comprising a polymerizable monomer (D).

14. The composition according to claim 13, wherein the polymerizable monomer (D) has the structure of Formula 6:

wherein in Formula (6), R each independently indicate a hydrogen atom or a methyl group, m and n each indicate an integer of 0 to 10, and m+n=0 to 10.

15. The composition according to claim 14, wherein in Formula (6), R each indicate a hydrogen atom, m and n each indicate an integer of 0 to 6, and m+n=2 to 6.

16. A cured product obtained by curing the compound according to claim 1.

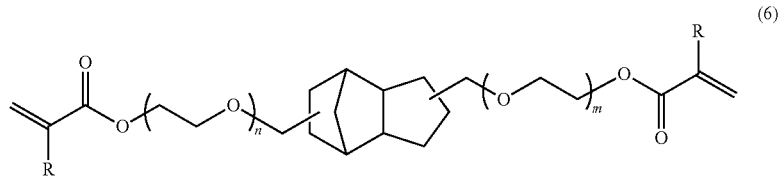

(6)

17. A cured product obtained by curing the composition according claim 11.

18. The compound according to claim 1, wherein $R_3$ in structure (i) is a phenyl group or a nonyl phenyl group.

* * * * *